(12) United States Patent
Bechtel et al.

(10) Patent No.: US 10,820,863 B2
(45) Date of Patent: Nov. 3, 2020

(54) DETERMINING TISSUE OXYGEN SATURATION WITH MELANIN CORRECTION

(71) Applicant: ViOptix, Inc., Newark, CA (US)

(72) Inventors: Kate LeeAnn Bechtel, Pleasant Hill, CA (US); Kimberly Merritt Shultz, Mountain View, CA (US); Alex Michael Margiott, Fremont, CA (US); George Edward Kechter, Peoria, IL (US)

(73) Assignee: ViOptix, Inc., Newark, CA (US)

( * ) Notice: Subject to any disclaimer, the term of this patent is extended or adjusted under 35 U.S.C. 154(b) by 522 days.

(21) Appl. No.: 15/494,444

(22) Filed: Apr. 21, 2017

(65) Prior Publication Data

US 2017/0303861 A1    Oct. 26, 2017

Related U.S. Application Data

(60) Provisional application No. 62/326,673, filed on Apr. 22, 2016, provisional application No. 62/326,644, (Continued)

(51) Int. Cl.
*A61B 5/1455* (2006.01)
*A61B 5/00* (2006.01)
(Continued)

(52) U.S. Cl.
CPC .......... *A61B 5/7271* (2013.01); *A61B 5/1032* (2013.01); *A61B 5/1495* (2013.01);
(Continued)

(58) Field of Classification Search
CPC . A61B 5/1032; A61B 5/1455; A61B 5/14551; A61B 5/14552; A61B 5/1495;
(Continued)

(56) References Cited

U.S. PATENT DOCUMENTS 5,353,790 A * 10/1994 Jacques .............. G01N 21/4738
                                                        250/574
6,385,821 B1   5/2002 Modgil et al.
(Continued)

FOREIGN PATENT DOCUMENTS

EP     0102816 A2    3/1984
EP     1889569 B1    6/2014
(Continued)

OTHER PUBLICATIONS

International Search Report, PCT Application PCT/US2017/029014, dated Aug. 2, 2017, 3 pages.

*Primary Examiner* — Eric F Winakur
*Assistant Examiner* — Chu Chuan Liu
(74) *Attorney, Agent, or Firm* — Aka Chan LLP

(57) ABSTRACT

An oximeter probe that takes into account tissue color (e.g., skin color or melanin content) to improve accuracy when determining oxygen saturation of tissue. Light is transmitted from a light source into tissue having melanin (e.g., eumelanin or pheomelanin). Light reflected from the tissue is received by a detector. A compensation factor is determined to account for absorption due to the melanin. The oximeter uses this compensation factor and determines a melanin-corrected oxygen saturation value.

20 Claims, 31 Drawing Sheets

Related U.S. Application Data filed on Apr. 22, 2016, provisional application No. 62/326,630, filed on Apr. 22, 2016, provisional application No. 62/325,919, filed on Apr. 21, 2016.

(51) Int. Cl.
*A61B 5/1495* (2006.01)
*A61B 5/103* (2006.01)

(52) U.S. Cl.
CPC ...... *A61B 5/14551* (2013.01); *A61B 5/14552* (2013.01); *A61B 5/4312* (2013.01); *A61B 5/7239* (2013.01); *A61B 5/742* (2013.01); *A61B 5/0002* (2013.01); *A61B 5/4869* (2013.01); *A61B 2560/0209* (2013.01); *A61B 2560/0223* (2013.01); *A61B 2562/046* (2013.01)

(58) Field of Classification Search
CPC ... A61B 5/0002; A61B 5/7239; A61B 5/7271; A61B 5/742; A61B 5/4312
See application file for complete search history.

(56) References Cited

U.S. PATENT DOCUMENTS

| | | | |
|---|---|---|---|
| 7,236,813 B2 | 6/2007 | Parker | |
| 8,100,834 B2* | 1/2012 | Shuler | A61B 5/7275 600/483 |
| 8,233,955 B2 | 7/2012 | Al-ali et al. | |
| 8,938,279 B1 | 1/2015 | Heaton, II et al. | |
| 2003/0009092 A1 | 1/2003 | Parker | |
| 2004/0034294 A1 | 2/2004 | Kimball et al. | |
| 2006/0053522 A1 | 3/2006 | Kimbell | |
| 2007/0244377 A1 | 10/2007 | Cozad et al. | |
| 2008/0221410 A1* | 9/2008 | Campbell | A61B 5/0059 600/310 |
| 2008/0319290 A1 | 12/2008 | Mao et al. | |
| 2009/0253968 A1 | 10/2009 | Cho et al. | |
| 2010/0005630 A1 | 1/2010 | Gitman et al. | |
| 2010/0292549 A1 | 11/2010 | Shuler | |
| 2010/0298728 A1 | 11/2010 | Addison et al. | |
| 2011/0205535 A1 | 8/2011 | Soller et al. | |
| 2011/0224518 A1 | 9/2011 | Tindi et al. | |
| 2011/0276276 A1 | 11/2011 | Kashyap et al. | |
| 2012/0289801 A1 | 11/2012 | Yamaguchi | |
| 2013/0023743 A1 | 1/2013 | Al-ali et al. | |
| 2013/0317331 A1 | 11/2013 | Bechtel et al. | |
| 2014/0046152 A1 | 2/2014 | Bechtel et al. | |
| 2014/0180043 A1 | 6/2014 | Addison et al. | |
| 2014/0288386 A1 | 9/2014 | Zand et al. | |
| 2014/0377200 A1* | 12/2014 | Kulesza | A61K 31/192 424/62 |

FOREIGN PATENT DOCUMENTS

| | | |
|---|---|---|
| WO | 2009090665 A1 | 7/2009 |
| WO | 2010011763 | 1/2010 |
| WO | 2010042264 A1 | 4/2010 |
| WO | 2014026200 | 2/2014 |

\* cited by examiner

| R1 S1 D1 | R2 S1 D2 | R3 S1 D3 | R4 S1 D4 | R5 S1 D5 | R6 S1 D6 | R7 S1 D7 | R8 S1 D8 | R1 S2 D1 | R2 S2 D2 | R3 S2 D3 | R4 S2 D4 | R5 S2 D5 | R6 S2 D6 | R7 S2 D7 | R8 S2 D8 | μ_a | μ_s' |
|---|---|---|---|---|---|---|---|---|---|---|---|---|---|---|---|---|---|
| 0000 | 0001 | 0010 | 0011 | 0100 | 0101 | 0110 | 0111 | 1000 | 1001 | 1010 | 1011 | 1100 | 1101 | 1110 | 1111 | 0000 | 0000 |
| 0001 | 0001 | 0010 | 0011 | 0100 | 0101 | 0110 | 0111 | 1000 | 1001 | 1010 | 1011 | 1100 | 1101 | 1110 | 1111 | 0000 | 0000 |
| ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ | ∘ ∘ ∘ |
| 1111 | 1111 | 1111 | 1111 | 1111 | 1111 | 1111 | 1111 | 1111 | 1111 | 1111 | 1111 | 1111 | 1111 | 1111 | 1111 | 1111 | 1111 |

| R1 S1 D1 | R2 S1 D2 | R3 S1 D3 | R4 S1 D4 | R5 S1 D5 | R6 S1 D6 | R7 S1 D7 | R8 S1 D8 | R1 S2 D1 | R2 S2 D2 | R3 S2 D3 | R4 S2 D4 | R5 S2 D5 | R6 S2 D6 | R7 S2 D7 | R8 S2 D8 | $\mu_q$ | $\mu_s'$ |
|---|---|---|---|---|---|---|---|---|---|---|---|---|---|---|---|---|---|
| 0000 | 0001 | 0010 | 0011 | 0100 | 0101 | 0110 | 0111 | 1000 | 1001 | 1010 | 1011 | 1100 | 1101 | 1110 | 1111 | 0000 | 0000 |
| 0001 | 0001 | 0010 | 0011 | 0100 | 0101 | 0110 | 0111 | 1000 | 1001 | 1010 | 1011 | 1100 | 1101 | 1110 | 1111 | 0000 | 0000 |
| ⋯ | ⋯ | ⋯ | ⋯ | ⋯ | ⋯ | ⋯ | ⋯ | ⋯ | ⋯ | ⋯ | ⋯ | ⋯ | ⋯ | ⋯ | ⋯ | ⋯ | ⋯ |
| 1111 | 1111 | 1111 | 1111 | 1111 | 1111 | 1111 | 1111 | 1111 | 1111 | 1111 | 1111 | 1111 | 1111 | 1111 | 1111 | 1111 | 1111 |

| λ3 | R1 S1 D1 | R2 S1 D2 | R3 S1 D3 | R4 S1 D4 | R5 S1 D5 | R6 S1 D6 | R7 S1 D7 | R8 S1 D8 | R1 S2 D1 | R2 S2 D2 | R3 S2 D3 | R4 S2 D4 | R5 S2 D5 | R6 S2 D6 | R7 S2 D7 | R8 S2 D8 |
|---|---|---|---|---|---|---|---|---|---|---|---|---|---|---|---|---|
| 10 | 0000 | 0001 | 0010 | 0011 | 0100 | 0101 | 0110 | 0111 | 1000 | 1001 | 1010 | 1011 | 1100 | 1101 | 1110 | 1111 |
| 10 | 0001 | 0001 | 0010 | 0011 | 0100 | 0101 | 0110 | 0111 | 1000 | 1001 | 1010 | 1011 | 1100 | 1101 | 1110 | 1111 |
| ... | ... | ... | ... | ... | ... | ... | ... | ... | ... | ... | ... | ... | ... | ... | ... | ... |
| 10 | 1111 | 1111 | 1111 | 1111 | 1111 | 1111 | 1111 | 1111 | 1111 | 1111 | 1111 | 1111 | 1111 | 1111 | 1111 | 1111 |

| λ4 | R1 S1 D1 | R2 S1 D2 | R3 S1 D3 | R4 S1 D4 | R5 S1 D5 | R6 S1 D6 | R7 S1 D7 | R8 S1 D8 | R1 S2 D1 | R2 S2 D2 | R3 S2 D3 | R4 S2 D4 | R5 S2 D5 | R6 S2 D6 | R7 S2 D7 | R8 S2 D8 |
|---|---|---|---|---|---|---|---|---|---|---|---|---|---|---|---|---|
| 11 | 0000 | 0001 | 0010 | 0011 | 0100 | 0101 | 0110 | 0111 | 1000 | 1001 | 1010 | 1011 | 1100 | 1101 | 1110 | 1111 |
| 11 | 0001 | 0001 | 0010 | 0011 | 0100 | 0101 | 0110 | 0111 | 1000 | 1001 | 1010 | 1011 | 1100 | 1101 | 1110 | 1111 |
| ... | ... | ... | ... | ... | ... | ... | ... | ... | ... | ... | ... | ... | ... | ... | ... | ... |
| 11 | 1111 | 1111 | 1111 | 1111 | 1111 | 1111 | 1111 | 1111 | 1111 | 1111 | 1111 | 1111 | 1111 | 1111 | 1111 | 1111 |

| MELANIN CONCENTRATION | OXYGEN SATURATION | BLOOD VOLUME | SCATTERING |
|---|---|---|---|
| 0000 | 0000 | 0000 | 0000 |
| 0001 | 0000 | 0000 | 0000 |
| ... | ... | ... | ... |
| 1111 | 1111 | 1111 | 1111 |

1100

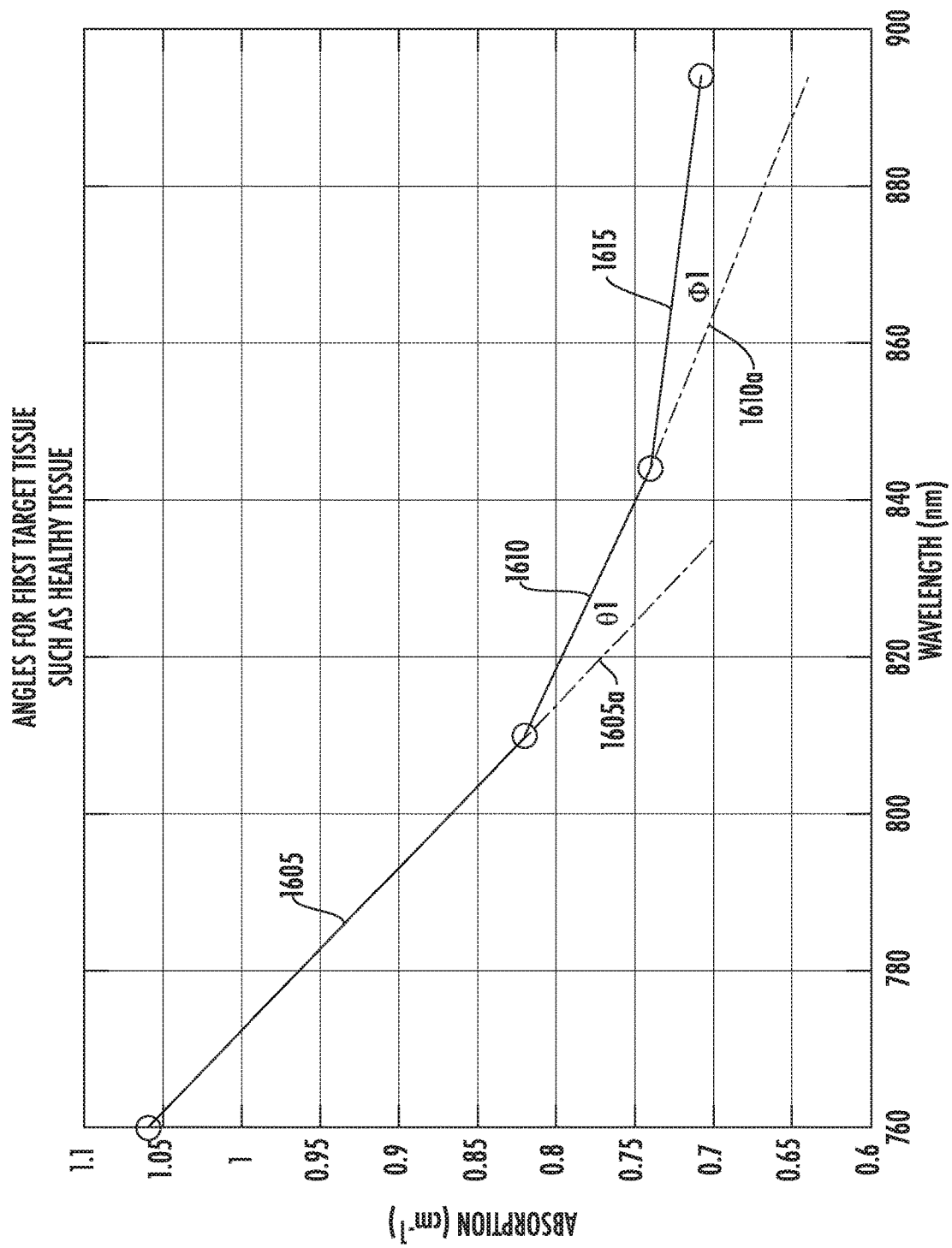

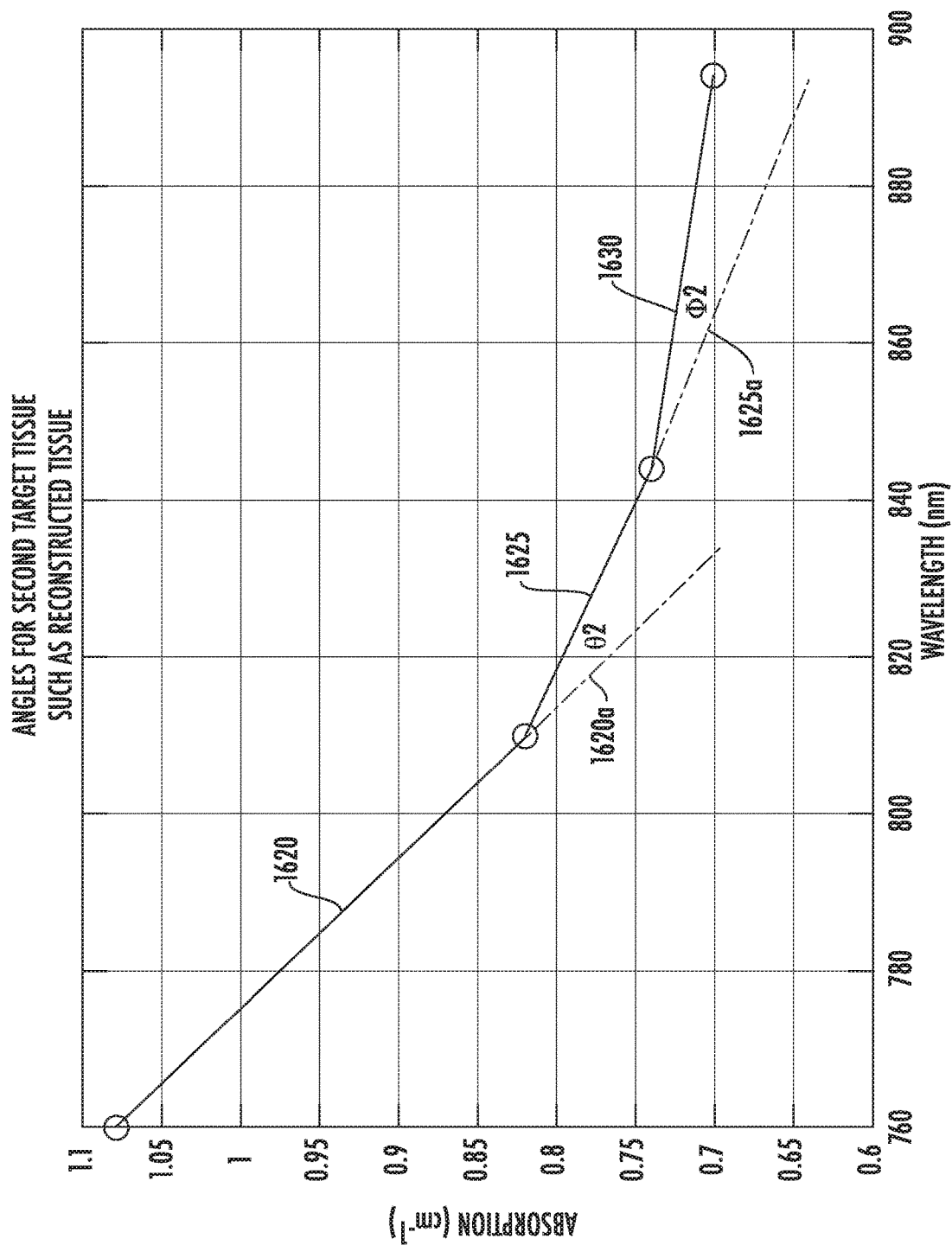

DETERMINING TISSUE OXYGEN SATURATION WITH MELANIN CORRECTION

CROSS-REFERENCE TO RELATED APPLICATIONS

This application claims the benefit of the following U.S. patent applications 62/325,919, filed Apr. 21, 2016, 62/326,630, 62/326,644, and 62/326,673, filed Apr. 22, 2016. These applications and U.S. patent application 62/363,562, filed Jul. 18, 2016, are incorporated by reference along with all other references cited in these applications.

BACKGROUND OF THE INVENTION

The present invention relates generally to optical systems that monitor oxygen levels in tissue. More specifically, the present invention relates to optical probes, such as oximeters, that include sources and detectors on sensor heads of the optical probes and that use locally stored simulated reflectance curves for determining oxygen saturation of tissue.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or person training for a marathon); and veterinary purposes (e.g., animal monitoring).

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated hemoglobin, deoxygenated hemoglobin, and melanin are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these measurements.

In particular, assessing a patient's oxygenation state, at both the regional and local level, is important as it is an indicator of the state of the patient's local tissue health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of nonideal conditions. While existing oximeters have been sufficient for post-operative tissue monitoring where absolute accuracy is not critical and trending data alone is sufficient, accuracy is, however, required during surgery in which spot-checking can be used to determine whether tissue might remain viable or needs to be removed.

Therefore, there is a need for improved tissue oximeter probes and methods of making measurements using these probes.

BRIEF SUMMARY OF THE INVENTION

An oximeter probe that takes into account tissue color (e.g., skin color or melanin content) to improve accuracy when determining oxygen saturation of tissue. Light is transmitted from a light source into tissue having melanin (e.g., eumelanin or pheomelanin). Light reflected from the tissue is received by a detector. A compensation factor is determined to account for absorption due to the melanin. The oximeter uses this compensation factor and determines a melanin-corrected oxygen saturation value.

In an implementation, to calculate oxygen saturation, an oximeter probe utilizes a relatively large number of simulated reflectance curves to quickly determine the optical properties of tissue under investigation. The optical properties of the tissue allow for the further determination of the oxygenated hemoglobin and deoxygenated hemoglobin concentrations of the tissue as well as the oxygen saturation of the tissue.

In one implementation, the oximeter probe can measure oxygen saturation without requiring a pulse or heart beat. An oximeter probe of the invention is applicable to many areas of medicine and surgery including plastic surgery. The oximeter probe can make oxygen saturation measurements of tissue where there is no pulse. Such tissue may have been separated from the body (e.g., a flap) and will be transplanted to another place in the body. Aspects of the invention may also be applicable to a pulse oximeter. In contrast to an oximeter probe, a pulse oximeter requires a pulse in order to function. A pulse oximeter typically measures the absorption of light due to the pulsing arterial blood.

Tissue oximeters can generate skewed oximetry measurements for tissues having different melanin content. In an implementation, the oximeter probe can make oximetry measurements of tissue where concentrations from melanin tend not to effect calculated relative oxygen saturation measurements. The oximeter probe exploits the relatively constant slope of the absorption coefficients of melanin where the slope tends not to change regardless of whether melanin content is tissue is relatively high or relatively low. The oximeter probe uses a mathematical determinative approach so that the melanin concentration contributions to the determined relative oxygen saturation go to zero. Thereby, actual melanin concentrations do not need to be determined to further determine relative oxygen saturation of target tissue.

In an implementation, a method includes transmitting light from a light source of an oximeter probe into a first tissue at a first location to be measured, where the first tissue comprises a first melanin component, and the first melanin component comprises at least one of eumelanin or pheomelanin; receiving light at a detector of the oximeter probe that is reflected by the first tissue in response to the transmitted light, where the received light comprises a first melanin absorption component due to the first melanin component; determining a melanin compensation component for a melanin absorption component due to a melanin component of tissue, where the melanin absorption component comprises the first melanin component and the melanin component comprises the first melanin component; and using the melanin compensation component, obtaining a melanin-corrected oxygen saturation value for the first tissue, where melanin-corrected oxygen saturation value accounts for the melanin absorption component.

In an implementation, a method includes providing an oximeter device comprising a probe tip comprising source structures and detector structures, where the oximeter device will measure oxygen saturation of a tissue comprising eumelanin and pheomelanin; providing to the oximeter device an indication of a skin color of the tissue to be measured; using the indication of a skin color to calculate the oxygen saturation of the tissue comprising eumelanin and pheomelanin to obtain a melanin-corrected oxygen saturation value; and displaying the melanin-corrected oxygen saturation value on a display.

In an implementation, a system includes an oximeter device that includes a probe tip that includes source structures and detector structures on a distal end of the device and includes a display proximal to the probe tip. The oximeter device calculates a melanin-corrected oxygen saturation value, and displays the melanin-corrected oxygen saturation value on the display. The oximeter device is specially configured to use the probe tip to make a first measurement and a second measurement to determine the melanin-corrected oxygen saturation value and receive first information based on the first measurement of a first tissue at a first location. The melanin-corrected oxygen saturation value is unavailable for display after the first measurement is made and before the second measurement is made. The oximeter device is specially configured to receive second information based on the second measurement of a second tissue at a second location where the second location is different from the first location; use the first information and second information to determine the melanin-corrected oxygen saturation value. The melanin-corrected oxygen saturation value takes into account melanin components of the first tissue and second tissue, and the melanin components comprise eumelanin and pheomelanin. And the oximeter device is configured to display the melanin-corrected oxygen saturation on the display.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 9 shows a table for a database for a homogeneous model of tissue of simulated reflectance curves that is stored in the memory of the oximeter probe in an implementation.

FIG. 10 shows a table for a database for a layered model of tissue of simulated reflectance curves that is stored in the memory of the oximeter probe in an implementation.

FIGS. 11A-11B show a table for a database for a layered model of tissue where each row in the database is for four simulated reflectance curves for the four wavelengths of light emitted from the simulated source structures and detected by the simulated detector structures.

FIGS. 16A and 16B show example graphs of absorption coefficients for the first target tissue and the second target tissue illuminated by a number of light wavelengths, such as the 760 nanometers, 810 nanometers, 845 nanometers, and 895 nanometers. Other wavelengths can be used by the oximeter probe including more or fewer wavelengths of light.

DETAILED DESCRIPTION OF THE INVENTION

Figure 1:
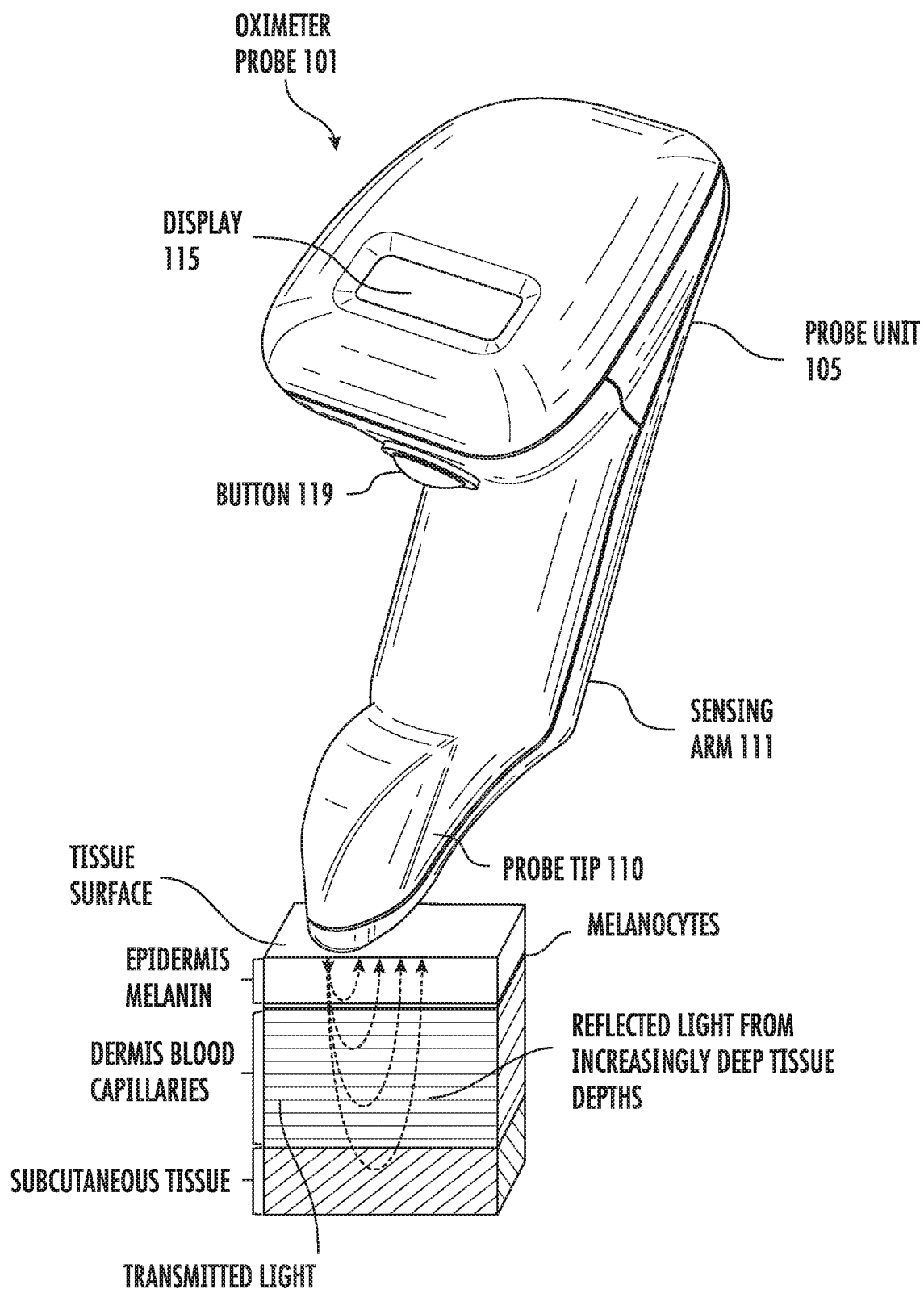
FIG. 1 shows an oximeter probe in an implementation.

FIG. 1 shows an image of an oximeter probe 101 in an implementation. Oximeter probe 101 is configured to make tissue oximetry measurements, such as intraoperatively and postoperatively. Oximeter probe 101 may be a handheld device that includes a probe unit 105, probe tip 110 (also referred to as a sensor head), which may be positioned at an end of a sensing arm 111. Oximeter probe 101 is configured to measure the oxygen saturation of tissue by emitting light, such as near-infrared light, from probe tip 110 into tissue, and collecting light reflected from the tissue at the probe tip.

Oximeter probe 101 includes a display 115 or other notification device that notifies a user of oxygen saturation measurements made by the oximeter probe. While probe tip 110 is described as being configured for use with oximeter probe 101, which is a handheld device, probe tip 110 may be used with other oximeter probes, such as a modular oximeter probe where the probe tip is at the end of a cable device that couples to a base unit. The cable device might be a disposable device that is configured for use with one patient and the base unit might be a device that is configured for repeated use. Such modular oximeter probes are well understood by those of skill in the art and are not described further.

Figure 2:
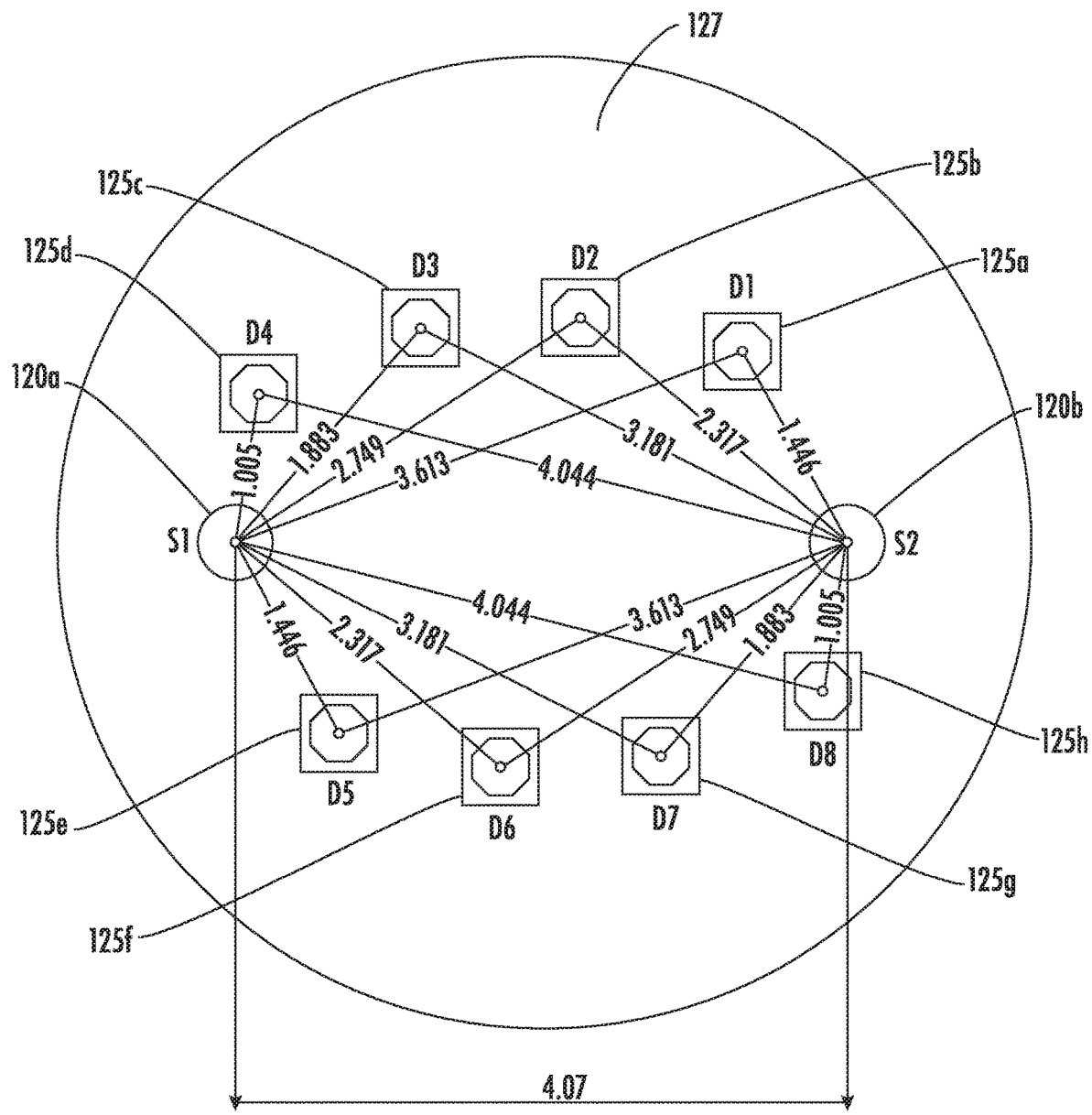
FIG. 2 shows an end view of the probe tip in an implementation.

FIG. 2 shows an end view of probe tip 110 in an implementation. Probe tip 110 is configured to contact tissue (e.g., a patient's skin) for which a tissue oximetry measurement is to be made. Probe tip 110 includes first and second source structures 120a and 120b (generally source structures 120) and includes first, second, third, fourth, fifth, sixth, seventh, and eighth detector structures 125a-125h (generally detector structures 125). In alternative implementations, the oximeter probe includes more or fewer source structures, includes more or fewer detector structures, or both.

Each source structure 120 is adapted to emit light (such as infrared light) and includes one or more light sources, such as four light sources that generate the emitted light. Each light source can emit one or more wavelengths of light. Each light source can include a light emitting diode (LED), a laser diode, an organic light emitting diode (OLED), a quantum dot LED (QMLED), or other types of light sources.

Each source structure can include one or more optical fibers that optically link the light sources to a face 127 of the probe tip. In an implementation, each source structure includes four LEDs and includes a single optical fiber that optically couples the four LEDs to the face of the probe tip. In alternative implementations, each source structure includes more than one optical fiber (e.g., four optical fibers) that optically couples the LEDs to the face of the probe tip.

Each detector structure includes one or more detectors. In an implementation, each detector structure includes a single detector adapted to detect light emitted from the source structures and reflected from tissue. The detectors can be photodetectors, photoresistors, or other types of detectors. The detector structures are positioned with respect to the source structures such that two or more (e.g., eight) unique source-to-detector distances are created.

In an implementation, the shortest source-to-detector distances are approximately equal. For example, the shortest source-to-detector distances are approximately equal between source structure 120a and detector structure 125d (S1-D4) and between source structure 120b and detector structure 125a (S2-D8) are approximately equal. The next longer source-to-detector distances (e.g., longer than each of S1-D4 and S2-D8) between source structure 120a and detector structure 125e (S1-D5) and between source structure 120b and detector structure 125a (S2-D1) are approximately equal. The next longer source-to-detector distances (e.g., longer than each of S1-D5 and S2-D1) between source structure 120a and detector structure 125c (S1-D3) and between source structure 120b and detector structure 125g (S2-D7) are approximately equal. The next longer source-to-detector distances (e.g., longer than each of S1-D3 and S2-D7) between source structure 120a and detector structure 125f (S1-D6) and between source structure 120b and detector structure 125b (S2-D2) are approximately equal. The next longer source-to-detector distances (e.g., longer than each of S1-D6 and S2-D2) between source structure 120a and detector structure 125c (S1-D2) and between source structure 120b and detector structure 125f (S2-D6) are approximately equal. The next longer source-to-detector distances (e.g., longer than each of S1-D2 and S2-D6) between source structure 120a and detector structure 125g (S1-D7) and between source structure 120b and detector structure 125c (S2-D3) are approximately equal. The next longer source-to-detector distances (e.g., longer than each of S1-D7 and S2-D3) between source structure 120a and detector structure 125a (S1-D1) and between source structure 120b and detector structure 125e (S2-D5) are approximately equal. The next longer source-to-detector distances (e.g., longest source-to-detector distance, longer than each of S1-D1 and S2-D5) between source structure 120a and detector structure 125h (S1-D8) and between source structure 120b and detector structure 125d (S2-D4) are approximately equal. In other implementations, the source-to-detector distance can all be unique or have fewer then eight distances that are approximately equal.

Table 1 below shows the eight unique source-to-detector distances according to an implementation. The increase between nearest source-to-detector distances is approximately 0.4 millimeters.

TABLE 1

| Source-to-Detector Pairs | Source-to-Detector Distances Millimeters |
|---|---|
| (S1-D4) | 1.005 |
| (S2-D8) | 1.005 |
| (S1-D5) | 1.446 |
| (S2-D1) | 1.446 |
| (S1-D3) | 1.883 |

TABLE 1-continued

| Source-to-Detector Pairs | Source-to-Detector Distances Millimeters |
|---|---|
| (S2-D7) | 1.883 |
| (S1-D6) | 2.317 |
| (S2-D2) | 2.317 |
| (S1-S2) | 2.749 |
| (S1-S2) | 2.749 |
| (S1-D7) | 3.181 |
| (S2-D3) | 3.181 |
| (S1-D1) | 3.613 |
| (S2-D5) | 3.613 |
| (S1-D8) | 4.004 |
| (S2-D4) | 4.004 |

In an implementation, detector structures 125a and 125e are symmetrically positioned about a point that is on a straight line connecting sources 120a and 120b. Detector structures 125b and 125f are symmetrically positioned about the point. Detector structures 125c and 125g are symmetrically positioned about the point. Detector structures 125d and 125h are symmetrically positioned about the point. The point can be centered between source structures 120a and 120b on the connecting line.

A plot of source-to-detector distance verses reflectance detected by detector structures 125 can provide a reflectance curve where the data points are well spaced along the x-axis. These spacings of the distances between source structures 120a and 120b, and detector structures 125 reduces data redundancy and can lead to the generation of relatively accurate reflectance curves.

In an implementation, the source structures and detector structures can be arranged at various positions on the probe surface to give the distances desired (such as indicated above). For example, the two sources form a line, and there will be equal number of detectors above and below this line. And the position of a detector (above the line) will have point symmetry with another detector (below the line) about a selected point on the line of the two sources. As an example, the selected point may be the middle between the two sources, but not necessarily. In other implements, the positioning can be arranged based on a shape, such as a circle, an ellipse, an ovoid, randomly, triangular, rectangular, square, or other shape.

The following patent applications describe various oximeter devices and oximetry operation, and discussion in the following applications can be combined with aspects of the invention described in this application, in any combination. The following patent application are incorporated by reference along with all references cited in these application Ser. No. 14/944,139, filed Nov. 17, 2015, Ser. No. 13/887,130 filed May 3, 2013, Ser. No. 15/163,565, filed May 24, 2016, Ser. No. 13/887,220, filed May 3, 2013, Ser. No. 15/214,355, filed Jul. 19, 2016, Ser. No. 13/887,213, filed May 3, 2013, Ser. No. 14/977,578, filed Dec. 21, 2015, Ser. No. 13/887,178, filed Jun. 7, 2013, Ser. No. 15/220,354, filed Jul. 26, 2016, Ser. No. 13/965,156, filed Aug. 12, 2013, Ser. No. 15/359,570, filed Nov. 22, 2016, Ser. No. 13/887,152, filed May 3, 2013, Ser. No. 29/561,749, filed Apr. 16, 2016, 61/642,389, 61/642,393, 61/642,395, 61/642,399 filed May 3, 2012, and 61/682,146, filed Aug. 10, 2012.

Figure 3:
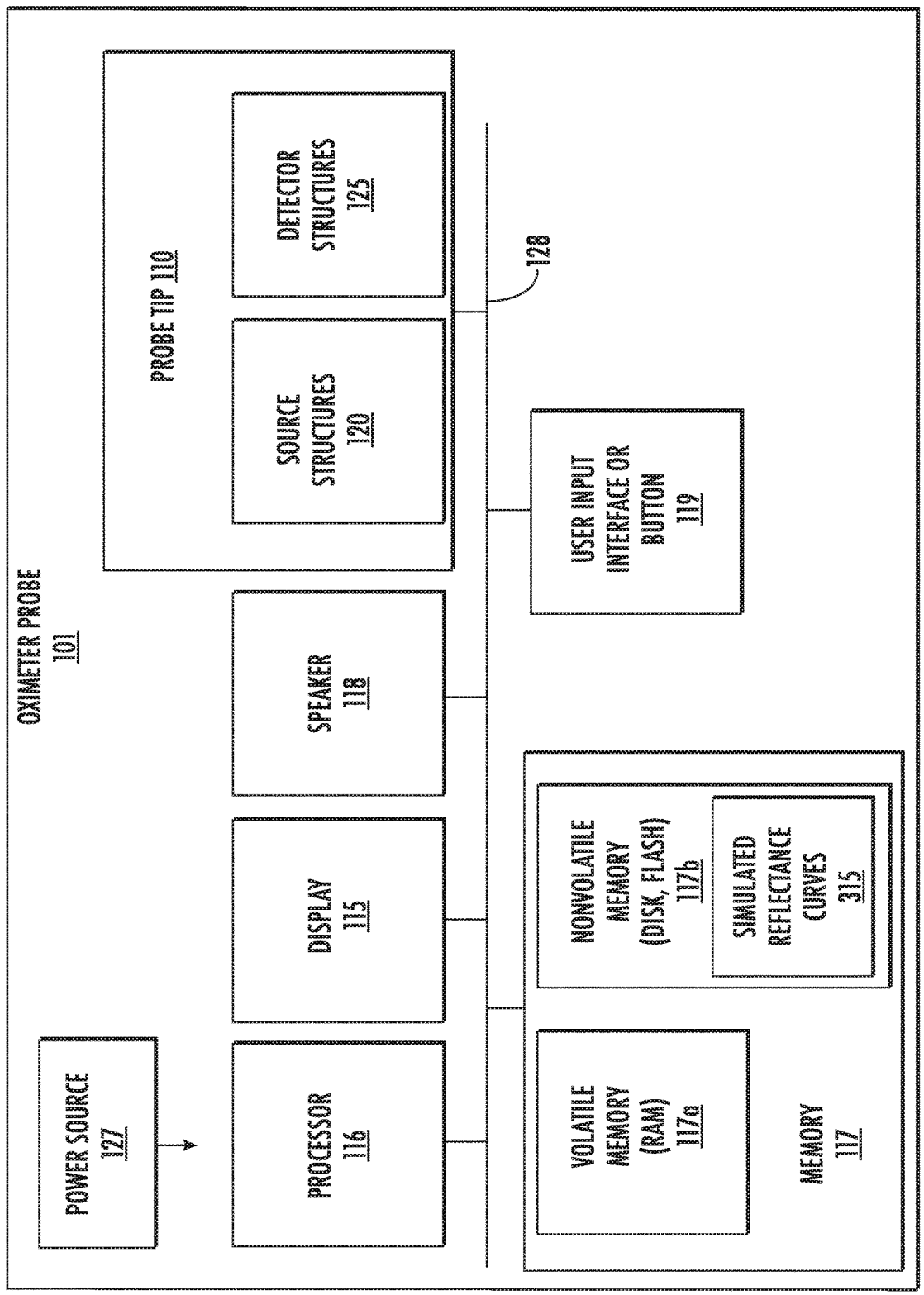
FIG. 3 shows a block diagram of an oximeter probe in an implementation.

FIG. 3 shows a block diagram of oximeter probe 101 in an implementation. Oximeter probe 101 includes display 115, a processor 116, a memory 117, a speaker 118, one or more user-selection devices 119 (e.g., one or more buttons, switches, touch input device associated with display 115), a set of source structures 120, a set of detector structures 125, and a power source (e.g., a battery) 127. The foregoing listed components may be linked together via a bus 128, which may be the system bus architecture of oximeter probe 101. Although this figure shows one bus that connects to each component, the busing is illustrative of any interconnection scheme serving to link these components or other components included in oximeter probe 101. For example, speaker 118 could be connected to a subsystem through a port or have an internal direct connection to processor 116. Further, the components described are housed in a mobile housing (see FIG. 1) of oximeter probe 101 in an implementation.

Processor 116 may include a microprocessor, a microcontroller, a multi-core processor, or other processor type. Memory 117 may include a variety of memories, such as a volatile memory 117a (e.g., a RAM), a nonvolatile memory 117b (e.g., a disk or FLASH). Different implementations of oximeter probe 101 may include any number of the listed components, in any combination or configuration, and may also include other components not shown.

Power source 127 can be a battery, such as a disposable battery. Disposable batteries are discarded after their stored charge is expended. Some disposable battery chemistry technologies include alkaline, zinc carbon, or silver oxide. The battery has sufficient stored charged to allow use of the handheld device for several hours. In an implementation, the oximeter probe is a disposable.

In other implementations, the battery is rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the handheld unit can include a recharger circuit (not shown). Batteries with rechargeable battery chemistry may be sometimes used as disposable batteries, where the batteries are not recharged but disposed of after use.

Figure 4:
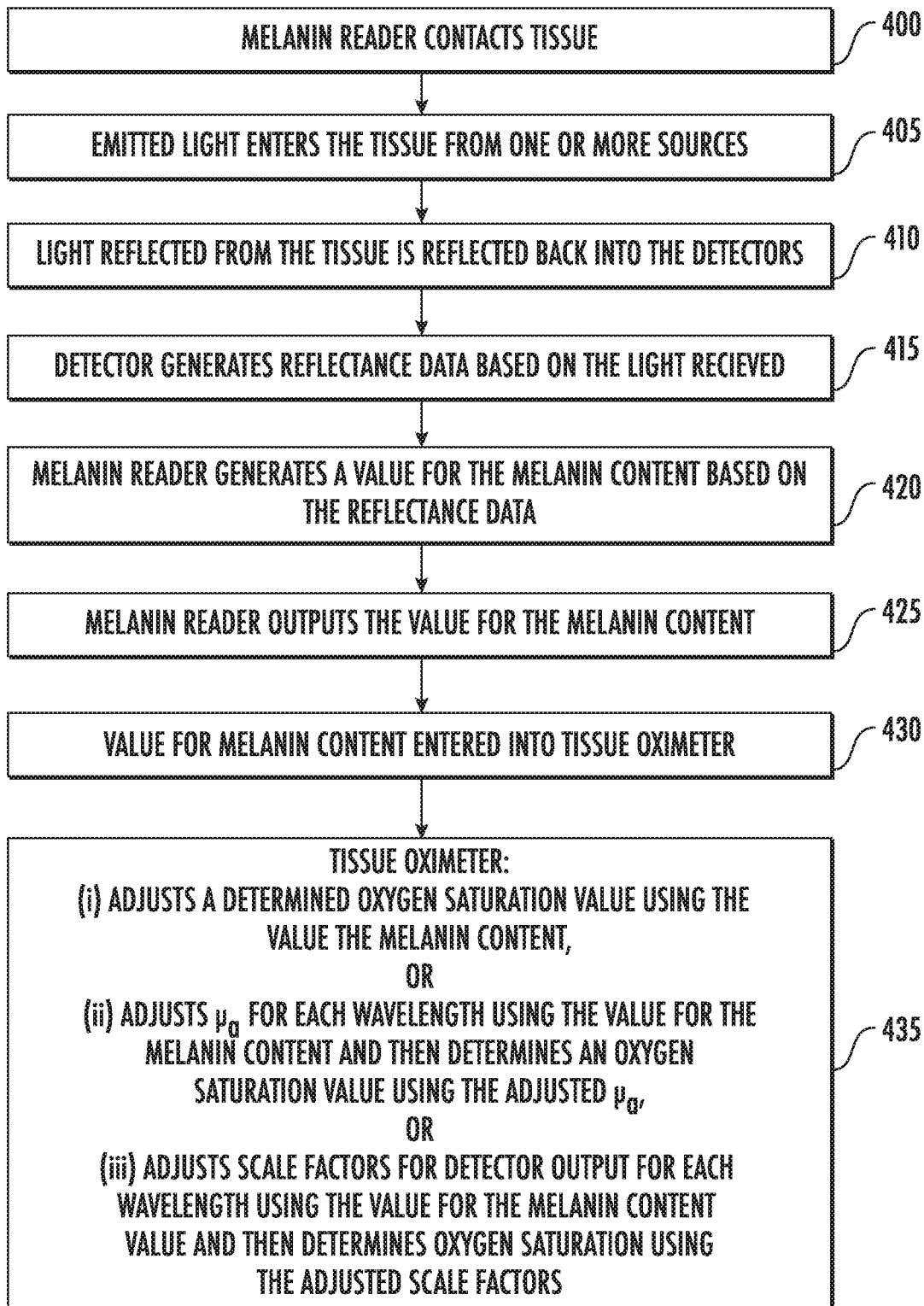
FIG. 4 shows a flow diagram of a method for determining optical properties of tissue (e.g., real tissue) by the oximeter probe in an implementation.

Tissue Analysis. FIG. 4 shows a flow diagram of a method for determining optical properties of tissue (e.g., real tissue) by oximeter probe 101 in an implementation. Oximeters are used to measure tissue with melanin, such as skin. Melanin affects oxygen saturation measurements because melanin absorbs light. Skin colors vary widely from person to person, from very dark skin to very light skin. Depending on the amount of melanin present, which will vary depending, for example, on the skin color, the amount of absorption can have a substantial effect on the measurement, making the measured value inaccurate.

Therefore, there is a need for an oximeter that takes into account a melanin component of the tissue being measured, so that the measured oxygen saturation value is accurate regardless of the skin color. The measured oxygen saturation value which accounts and compensates for the melanin component of the tissue can be referred to as a melanin-corrected oxygen saturation value.

The melanin in skin is eumelanin and pheomelanin (e.g., two melanin components), which are naturally occurring melanins in various relative percentages. In contrast, most internal organs and tissue in the human body do not have melanin. Thus, there is no need to account for melanin when using an oximeter to make oxygen saturation measurements for such internal tissue. However, the human brain has neuromelanin, which is not present elsewhere in the body, especially the skin.

In an implementation, the oximeter determines and corrects for melanin absorption in skin tissue (and any other tissue) that have eumelanin and pheomelanin pigments. This oximeter does not account and correct for neuromelanin or synthetic melanins since these are not found in the skin. In other implementations, the oximeter determines and corrects for melanin absorption due to a variety of melanins, including eumelanin, pheomelanin, or neuromelanin or synthetic melanins, or any combination of these.

The oximeter probe uses determined melanin content (e.g., eumelanin content, pheomelanin content, or both eumelanin and pheomelanin contents) for the tissue to correct various tissue parameters that are measured by the oximeter probe. The flow diagram represents one example implementation. Steps may be added to, removed from, or combined in the flow diagram without deviating from the scope of the implementation.

At 400, a melanin reader optically couples (e.g., contacts) to the tissue. Melanin readers are optoelectronic devices that are adapted for emitting light, step 405, into tissue, and detecting the light, step 410, after having been transmitted through the tissue or reflected from the tissue. The light detected by the melanin reader is converted to electrical signals, step 415, that are used by the device to determine melanin content of the tissue, step 420. The melanin reader can output a value for the melanin content, step 425, on a display of the reader or via a wired or wireless output. The value for melanin content represents values for eumelanin content, pheomelanin content, or both eumelanin and pheomelanin contents In an implementation, at 430, information (e.g., a numerical value) about the melanin content is entered into oximeter probe 101. The information can be entered into the oximeter probe via a user (e.g., a human user) or via a wired or wireless communication between the melanin reader and the oximeter probe.

In a first implementation, at 435, the oximeter probe uses the information for the melanin content to adjust one or more measured values generated by the probe. In an implementation, the oximeter probe determines a value for the oxygen saturation of the tissue. The oximeter probe thereafter adjusts the value for the oxygen saturation using the information for the melanin content (e.g., information for eumelanin content, pheomelanin content, or both eumelanin and pheomelanin contents). The oximeter probe can adjust the value for the oxygen saturation via one or more arithmetic operations, mathematical functions, or both. For example, the information for the melanin content can be used as an offset (e.g., additive offset), a scale factor, or both for adjusting the value for the oxygen saturation.

In an alternative implementation, at 435, the oximeter probe determines the absorption coefficient $\mu_a$ (mua), the reduced scattering coefficient $\mu_s'$ (mus prime), or both for the tissue for a number of wavelengths of light (e.g., four wavelengths of light) emitted and detected by the oximeter probe. Thereafter, the oximeter probe adjusts the determined absorption ($\mu_a$) values for each wavelength of light using the information about melanin content (e.g., eumelanin content, pheomelanin content, or both eumelanin and pheomelanin contents). The oximeter probe can adjust the absorption ($\mu_a$) values via one or more arithmetic operations, mathematical functions, or both. For example, the information for the melanin content can be used as an offset (e.g., additive offset), a scale factor, or both for adjusting the absorption ($\mu_a$) values. Thereafter, the oximeter probe uses the absorption ($\mu_a$) values to determine a value for the oxygen saturation for the tissue. Determination of absorption ($\mu_a$) and reduced scattering ($\mu_s$) are described below.

In another implementation, at 435, the oximeter probe applies one or more melanin correction functions to reflectance data generated by the detector structures. The melanin correction functions are based on the information for the melanin content (e.g., eumelanin content, pheomelanin content, or both eumelanin and pheomelanin contents). The reflectance data can be analog reflectance data generated by the detector structures prior to being digitized by one or more electronic components of the oximeter probe or the reflectance data can be digitized reflectance data. The melanin correction functions can be applied to the analog reflectance data or the digitized reflectance data. The melanin correction function includes one or more mathematical operations that are applied to the reflectance data. The scale factors are determined by the oximeter probe based on information for the melanin content that is entered into the oximeter probe. The reflectance data can be adjusted for melanin content for each wavelength of light emitted by the oximeter probe.

In an implementation, the melanin correction function can be a combined function (e.g., having scale factors) that is combined with one or more calibration functions (e.g., having scale factors). The calibration function can include scale factors for correcting the detector responses based on a variety of factors, such as differences that occur as a result of manufacturing, that occur as a result of temperature drift of the detector structures, or other considerations. After the reflectance data are adjusted by the oximeter probe, the probe can then determine the oxygen saturation of blood in the tissue to be measured.

Figure 5:
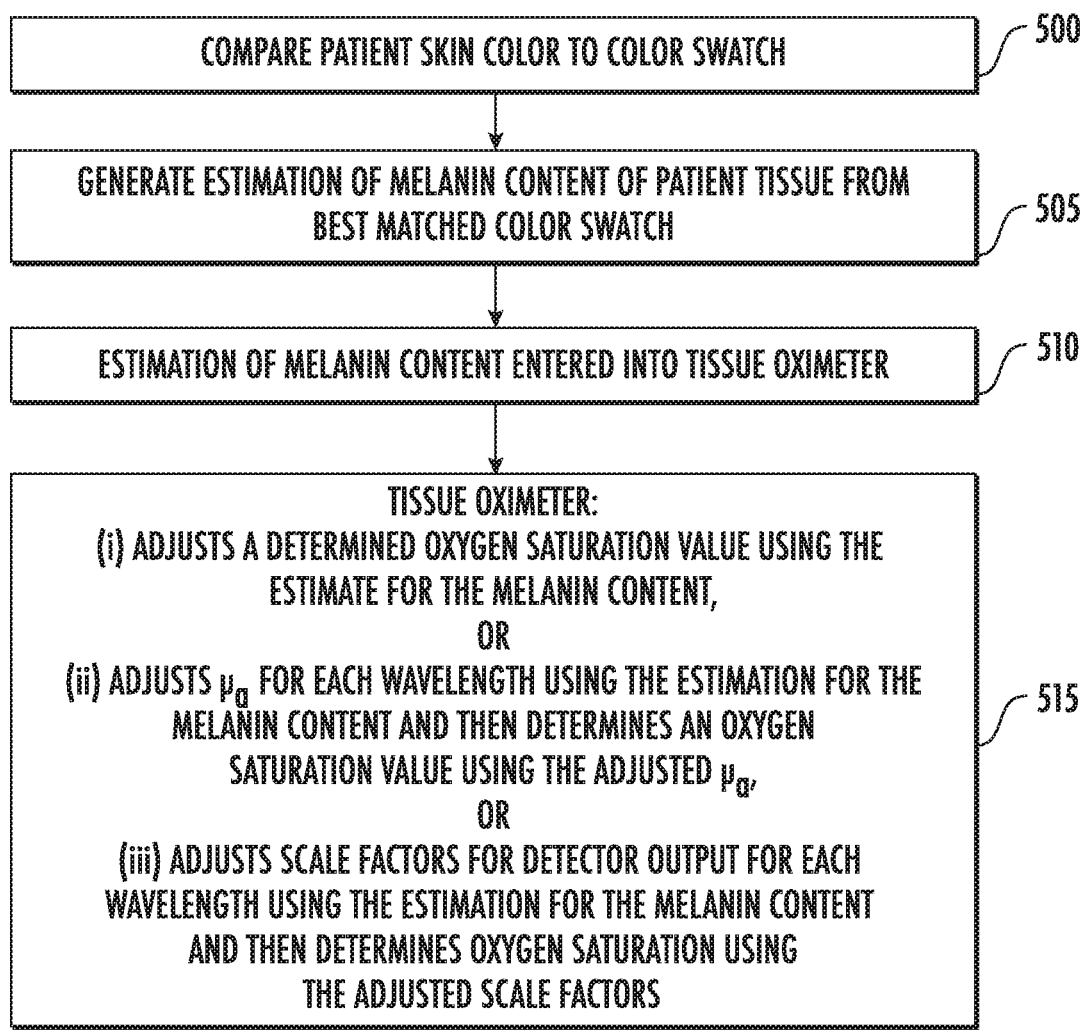
FIG. 5 shows a flow diagram of a method for determining optical properties of tissue by the oximeter probe in an implementation.

FIG. 5 shows a flow diagram of a method for determining optical properties of tissue by oximeter probe 101 in an implementation. The oximeter probe uses information about the melanin content (e.g., information for eumelanin content, pheomelanin content, or both eumelanin and pheomelanin contents) for the tissue to correct various tissue parameters measured by the oximeter probe. The flow diagram represents one example implementation. Steps may be added to, removed from, or combined in the flow diagram without deviating from the scope of the implementation.

At 500, the color of the tissue is compared to two or more color samples of a number of color samples (sometimes referred to as color swatches) to determine whether the color of one of the color samples approximately matches the color of the tissue. Each color sample used for the color comparison is associated with a value of melanin content. Information (e.g., a numerical value) that identifies the melanin content for the color sample can be located on the color sample. In an implementation, the colors are the Pantone® colors of Pantone LLC of Carlstadt, N.J.

The comparison between the color of the tissue and the color of the color samples can be performed by a color comparison tool, such as one or more of the color comparison tools of X-Rite, Incorporated of Grand Rapids Mich. In an implementation, the comparison can be performed visually by a human, such as the patient or a medical provider. In an implementation, the oximeter probe is adapted to determine a value for the melanin content of the tissue, which can displayed on the display of the probe.

At 505, subsequent to the comparison, the value for the melanin content of the tissue is determined based on the comparison.

In an alternative implementation, the value for the melanin content is determined from an estimate of the content based on a finite range of melanin content values. The number of values in a range for melanin content can include two or more values.

For example, the number of values in a range for melanin contents can be 2 (e.g., binary levels), such as 1 for light colored tissue (e.g., first skin level for first level of melanin content) and 2 for dark tissue (e.g., second skin level for second level of melanin content), can be 3 (e.g., 1 for light tissue color, 2 for medium color tissue, darker than 1, and 3 for dark color tissue, darker than 1 and 2), or 4, 5, 6, 7, 8, 9, 10 or more values for different skin colors. An estimation of the value for melanin content can be provided by the patient or a medical provider.

At 510, the information about the melanin content can be entered into the oximeter probe. Step 510 can be skipped in a method where the oximeter probe determines the value for the melanin content. Button 119 can be activated a predetermined number of times to place the oximeter probe into a data entry mode in which the information for the melanin content can be entered. The information for the melanin content can thereafter be entered into the probe by further activation of the button, via a wired communication with the probe, via a wireless communication with the probe, via the display if the display is a touch interface display, via an audible interface (e.g., a microphone and voice recognition software in the probe), or by other input techniques. Alternatively, the button interface can provide (e.g., via interaction with the processor) on screen selectable options (or options otherwise provided, such as lighted LEDs) for melanin content (e.g., 1 and 2 for light and dark skin, 1, 2, and 3 for light, medium, and dark colored skin, or more user selectable levels). Where the display is a touch interface display, the user selectable options for melanin level can be displayed on the display where a user can touch there selection. In implementation of the oximeter device the operate with other user input device (e.g., mouse, external keyboard, or others) the user can select the user selectable melanin options using one or more of these devices.

At 515, the oximeter probe is adapted to use information about the melanin content to adjust one or more measurements or calculations performed by the oximeter probe. For example, the oximeter probe can use the information to adjust oxygen saturation value for the tissue, adjust absorption ($\mu_a$), adjust reduced scattering ($\mu_s'$), adjust values generated by the detector or detectors, or one or more of a combination of these adjustments. Each of these adjustments is described further above with respect to step 435.

Figure 6:
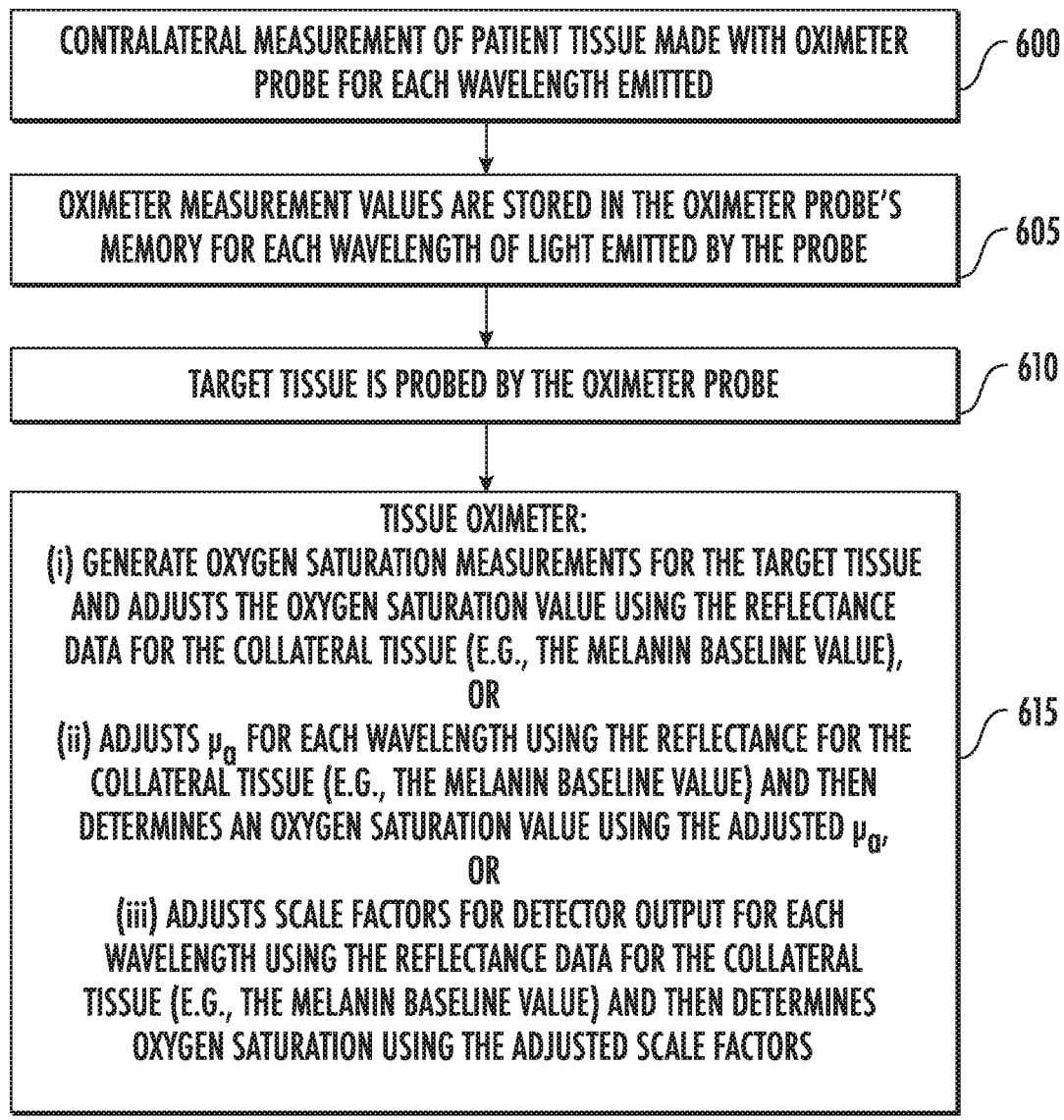
FIG. 6 shows a flow diagram of a method for determining optical properties of tissue by the oximeter probe in an implementation.

FIG. 6 shows a flow diagram of a method for determining optical properties of tissue by oximeter probe 101 in an implementation. The oximeter probe uses the determined melanin content of the tissue to correct various tissue parameters that are measured by the probe. The flow diagram represents one example implementation. Steps may be added to, removed from, or combined in the flow diagram without deviating from the scope of the implementation.

At 600, one or more contralateral measurements of the tissue are made with the oximeter probe. The contralateral measurements are made using the oximeter probe on a portion of tissue (e.g., healthy breast tissue, left breast, left side of a breast) before a measurement is made using the oximeter probe on target tissue that is to be measured (e.g., breast tissue for which tissue health is to be determined, e.g., right breast, right side of a breast where the first target tissue is the left side of the breast). The contralateral measurements of the tissue can be made for each wavelength of light emitted by the oximeter probe.

At 605, reflectance data generated by the detector structures are digitized by the electronic elements of the oximeter probe and are stored in memory. The reflectance data provide a basis of comparison for subsequent tissue measurement. For example, the contralateral measurements provide baseline measurements of the melanin content of the contralateral tissue where the baseline measurements can be used by the processor to correct for various measurements made the oximeter probe.

At 610, oximetry measurements of the target tissue to be measured are made by the oximeter probe.

At 615, in an implementation, the processor generates oxygen saturation values for target tissue using the oximetry measurements. Thereafter, the processor retrieves the stored reflectance data stored at 605 for the contralateral tissue and uses the retrieved values to adjust the oxygen saturation values. That is, the processor uses the baseline measurement for melanin content for the healthy contralateral tissues tissue to adjust the oxygen saturation values of the target tissue.

At 615, in an alternative implementation, the processor determines absorption $\mu_a$, reduced scattering coefficient or both from the oximetry measurements of the target tissue. Thereafter, the processor retrieves the reflectance data stored at 605 for the contralateral tissue and uses the retrieved values to adjust $\mu_a$, $\mu_s$, or both. The processor then uses the adjusted $\mu_a$ value to calculate values for oxygenated hemoglobin, deoxygenated hemoglobin, or other values for the target tissue. That is, the processor uses the baseline measurement for melanin content of the healthy contralateral tissue to adjust $\mu_a$ for the target tissue.

At 615, in an another alternative implementation, the processor retrieves the stored reflectance data stored at 605 for the contralateral tissue and uses the retrieved values to adjust the reflectance data generated by the detector structures for the target tissue. The adjustments applied by the processor to the reflectance data can be simple offsets (e.g., addition offsets), scale factors (e.g., multiplication offsets), functional corrections, other corrections, or any one or these adjustments in any combination. That is, the processor adjusts the values generated by the detector structures using the baseline measurement for melanin content for the healthy tissue to adjust the reflectance data for the target tissue.

Stored Simulated Reflectance Curves. According to an implementation, memory 117 stores a number of Monte-Carlo-simulated reflectance curves 315 ("simulated reflectance curves"), which may be generated by a computer for subsequent storage in the memory. Each of the simulated reflectance curves 315 represents a simulation of light (e.g., near infrared light) emitted from one or more simulated source structures into simulated tissue and reflected from the simulated tissue into one or more simulated detector structures. Simulated reflectance curves 315 are for a specific configuration of simulated source structures and simulated detector structures, such as the configuration of source structures 120a-120b and detector structures 125a-125h of probe tip 110 having the source-to-detector spacing described above with respect to FIG. 2.

Therefore, simulated reflectance curves 315 model light emitted from the source structures and collected by the detector structures of oximeter probe 101. Further, each of the simulated reflectance curves 315 represents a unique real tissue condition, such as specific tissue absorption and tissue scattering values that relate to particular concentrations of tissue chromophores and particular concentrations of tissue scatterers. For example, the simulated reflectance curves can be generated for simulated tissue having various melanin contents, various oxygenated hemoglobin concentrations, various deoxygenated hemoglobin concentrations, various concentrations of water, a static value for the concentrations of water, various concentration of fat, a static value for the concentration of fat, or various absorption ($\mu_a$) and reduced scattering ($\mu_s'$) values.

The number of simulated reflectance curves stored in memory 117 may be relatively large and can represent nearly all, if not all, practical combinations of optical properties and tissue properties that may be present in real tissue that is analyzed for viability by oximeter probe 101. While memory 117 is described as storing Monte-Carlo-simulated reflectance curves, memory 117 may store simulated reflectance curves generated by methods other than Monte-Carlo methods, such as using a diffusion approximation.

Figure 7:
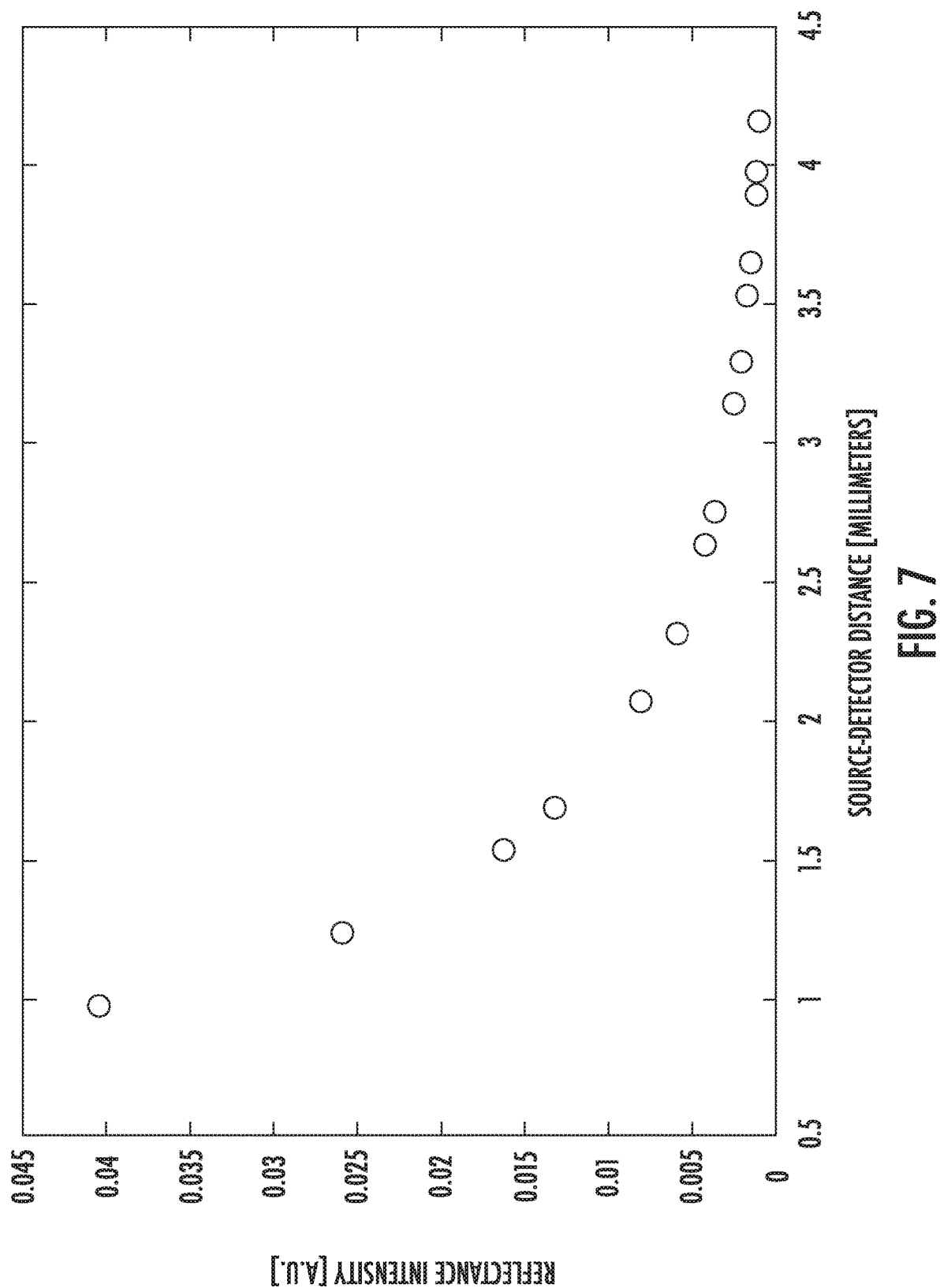
FIG. 7 shows an example graph of a reflectance curve, which may be for a specific configuration of source structures and detector structures, such as the configuration source structures and detector structures of the probe tip.

FIG. 7 shows an example graph of a reflectance curve, which may be for a specific configuration of source structures 120 and detector structures 125, such as the configuration source structures and detector structures of probe tip 110. The horizontal axis of the graph represents the distances between source structures 120 and detector structures 125 (i.e., source-to-detector distances). If the distances between source structures 120 and detector structures 125 are appropriately chosen, and the simulated reflectance curve is a simulation for source structures 120 and detector structures 125, then the lateral spacings between the data points in the simulated reflectance curve will be relatively uniform. Such uniform spacings can be seen in the simulated reflectance curve in FIG. 7. The vertical axis of the graph represents the simulated reflectance of light that reflects from tissue and is detected by detector structures 125. As shown by the simulated reflectance curve, the reflected light that reaches detector structures 125 varies with the distance between source structures and detectors structures, with the reflected light detected at smaller source-to-detectors distances greater than the reflected light detected a larger source-to-detector distances.

Figure 8:
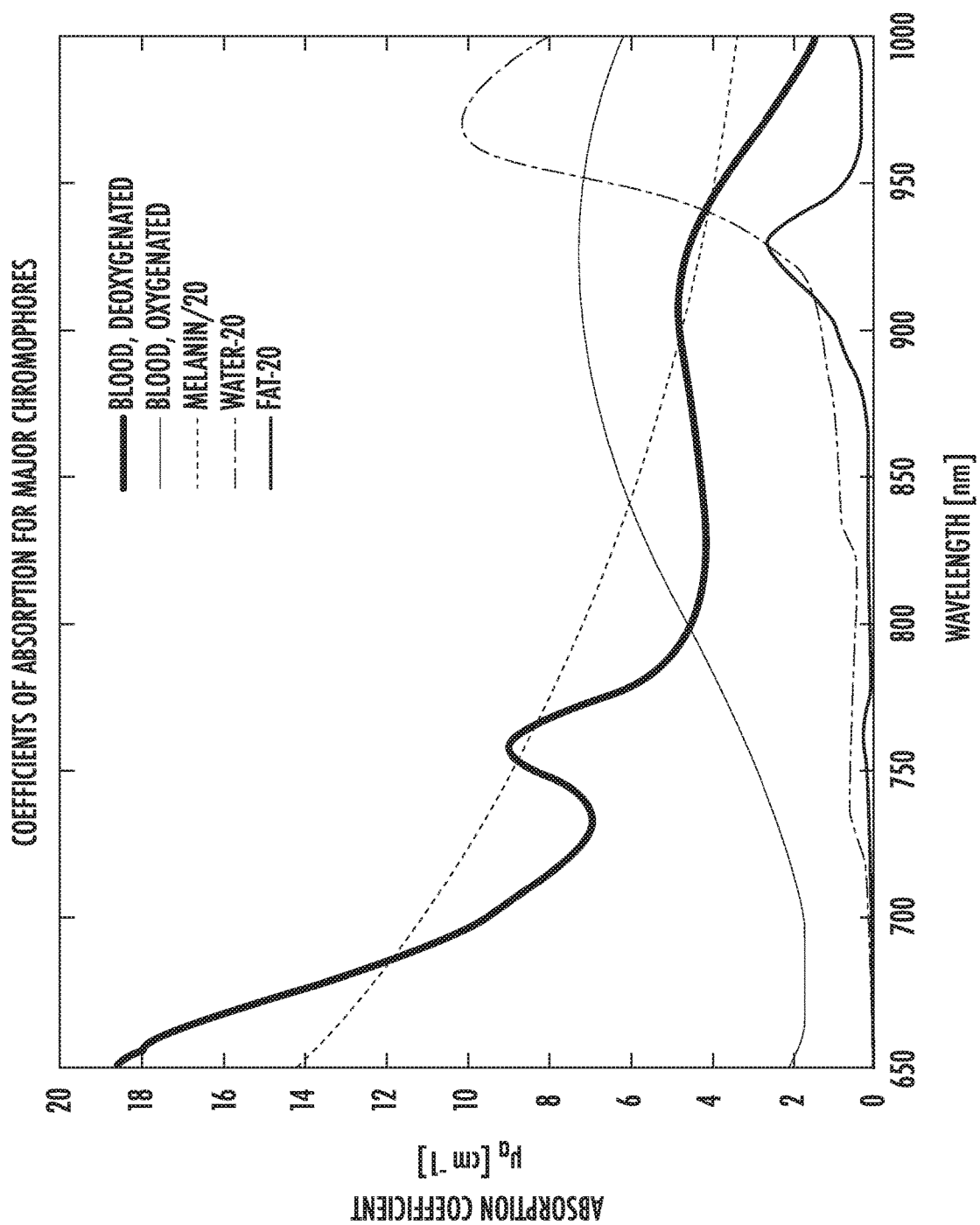
FIG. 8 shows a graph of the absorption coefficient $\mu_a$ in arbitrary units versus wavelength of light for oxygenated hemoglobins, deoxygenated hemoglobins, melanin, and water in tissue.

FIG. 8 shows a graph of the absorption coefficient $\mu_a$ versus wavelength of light for some significant tissue chromophores: blood containing oxygenated hemoglobin, blood containing deoxygenated hemoglobin, melanin, and water. In an implementation, the Monte-Carlo simulations used for generating the simulated reflectance curve are functions of one or more select chromophores that may be present in tissue. The chromophores can include melanin, oxygenated hemoglobin, deoxygenated hemoglobin, water, lipid, cytochrome, or other chromophores, in any combination. Oxygenated hemoglobins, deoxygenated hemoglobins, and melanin are the most dominant chromophores in tissue for much of the visible and near-infrared spectral range.

In an implementation, memory 117 stores a select number of data points for each of the simulated reflectance curves 315 and might not store the entirety of the simulated reflectance curves. The number of data points stored for each of the simulated reflectance curves 315 may match the number of source-detector pairs. For example, if probe tip 110 includes two source structures 120a-120b and includes eight detector structures 125a-125h, then oximeter probe 101 includes sixteen source-detector pairs, and memory 117 may thus store sixteen select data points for each of the simulated reflectance curves for each wavelength of light emitted by source structure 120a or source structure 120b. In an implementation, the stored data points are for the specific source-to-detectors distances of probe tip 110, such as those shown in Table 1.

Thus, the simulated reflectance curve database stored in memory 117 might be sized 16×5850 where sixteen points are stored per curve that may be generated and emitted by each source structure 120 and measured by each detector structure 125, where there are a total of 5850 curves spanning the optical property ranges. Alternatively, the simulated reflectance curve database stored in memory 117 might be sized 16×4×5850 where sixteen points are stored per curve for four different wavelengths that may be generated and emitted by each source structure and where there are a total of 5850 curves spanning the optical property ranges. The 5850 curves originate, for example, from a matrix of 39 scattering coefficients $\mu_s'$ values and 150 absorption coefficient $\mu_a$ values. In other implementations, more or fewer simulated reflectance curves are stored in the memory. For example, the number of simulated reflectance curves stored in memory can range from about 5000 curves, to about 250,000 curves, to about 400,000 curves, or more.

The reduced scattering coefficient $\mu_s'$ values might range from 5:5:24 per centimeter. The $\mu_a$ values might range from 0.01:0.01:1.5 per centimeter. It will be understood that the foregoing described ranges are example ranges and the number source-detectors pairs, the number of wavelengths generated and emitted by each source structure, and the number of simulated reflectance curves may be smaller or larger.

FIG. 9 shows a database 900 of simulated reflectance curves 315 that is stored in the memory of the oximeter probe in an implementation. The database is for a homogeneous model of tissue. Each row in the database represents one simulated reflectance curve generated from a Monte-Carlo simulation for simulated light emitted into simulated tissue from two simulated source structures (e.g., source structures 120a-120b) and detected by eight simulated detector structures (e.g., detector structures 125a-125h) subsequent to reflection from the simulated tissue. The Monte-Carlo simulations used for generating the simulated reflectance curves for the databases are for a homogeneous tissue model. The simulated tissue for the homogeneous tissue model has homogeneous optical properties from the tissue surface through the epidermis, the dermis, and the subcutaneous tissue. That is, the optical properties of the epidermis, dermis, and subcutataneous are the same for the Monte-Carlo simulations. In the database, each of the simulated reflectance curves is associated with a value for absorption ($\mu_a$) and a value for reduced scattering ($\mu_s'$). Each of the simulated reflectance curves in the database can be associated with values for other chromophores.

The database of simulated reflectance curves can include actual values (e.g., floating point values) for simulated reflectances or can include indexed values (e.g., binary values) for the actual values for the simulated reflectances. As shown in FIG. 9, the database includes indexed values (e.g., binary values) for the actual values for the simulated reflectances. The database can include binary words of a variety of lengths dependent, for example, on the accuracy of the entries. The binary words can be 2 bits long, 4 bits long, 8 bits long, 16 bits long, 32 bits long, or other lengths.

In an implementation, one or more mathematical transforms are applied to the simulated reflectance curves prior to entry of the values for the curves into the database. The mathematical transforms can improve the fit of the reflectance data generated by the detector structures to the simulated reflectance curves. For example, a log function can be applied to the simulated reflectance curves to improve the fit of the measured data generated by the detector structures to the simulated reflectance curves.

When an oximetry measurement is made, the reflectance data for each wavelength of emitted light is detected by the detector structures and fitted to the simulated reflectance curves of database 900 individually. For the reflectance data for each wavelength of emitted light fitted to the simulated reflectance curves, the oximeter probe determines absorption $\mu_a$, reduced scattering $\mu_s'$ or both of these values. For example, a first set of reflectance data for a first wavelength of light is fitted to the simulated reflectance curves to determine one or more of absorption $\mu_a$, and reduced scattering $\mu_s'$ (e.g., a first set of tissue parameters). Fitting the reflectance data to the simulated reflectance curves is described further below.

Thereafter, a second set of reflectance data for a second wavelength of light is fitted to the simulated reflectance curves in database 900 to determine one or more of absorption $\mu_a$, and reduced scattering $\mu_s'$ (e.g., a second set of tissue parameters) for the second wavelength. Thereafter, a third set of reflectance data for a third wavelength of light is fitted to the simulated reflectance curves in database 900 to determine one or more of absorption $\mu_a$, and reduced scattering $\mu_s'$ (e.g., a third set of tissue parameters). Thereafter, a fourth set of reflectance data for a fourth wavelength of light is fitted to the simulated reflectance curves in database 900 to determine one or more of absorption $\mu_a$, and reduced scattering $\mu_s'$ (e.g., a fourth set of tissue parameters) for the fourth wavelength.

The four sets of tissue parameters can then be used by the oximeter probe together to determine various values for the tissue, such as oxygenated hemoglobin concentration, deoxygenated hemoglobin concentration, melanin content, or other parameters.

FIG. 10 shows a database 1000 of simulated reflectance curves that is stored in the memory of the oximeter probe in an implementation. The database is for a layered model of tissue (e.g. layered skin). The Monte-Carlo simulations that generated the simulated reflectance curves use the layered tissue model for the simulations. The layered tissue can include two or more layers. In an implementation, the layered tissue includes two layers of tissue. The two layers of tissue have different optical properties, such as different absorption $\mu_a$, reduced scattering $\mu_s'$, or both of these properties.

In one implementation, a first simulated tissue layer is for the epidermis and a second simulated tissue layer is for the dermis. The thickness of the epidermis used in the Monte-Carlo simulations can range from about 40 microns to about 140 microns. For example, the thickness for the epidermis can be 40 microns, 50 microns, 60 microns, 70 microns, 80 microns, 90 microns, 100 microns, 110 microns, 120 microns, 130 microns, 140 microns, or other thickness. The thickness of the dermis used in the Monte-Carlo simulations can range from less than 1 millimeter to an effectively infinite thickness, such as 12 millimeters or greater.

One or more optical properties of the epidermis can be varied when the simulated reflectance curves are generated for the dermis. For example, melanin content can be varied for the epidermis when the simulation reflectance curves are generated for the dermis. Alternatively, $\mu_a$ can be varied for the epidermis when the simulation reflectance curves are generated for the dermis.

In an implementation, database 1000 includes the simulated reflectance curves for the light that is reflected by the combination of the epidermis and the dermis.

The reflectance data for each wavelength of light emitted by the source structures and detected by the detector structures for real tissue measured by the oximeter probe is fit to the simulated reflectance curves one at a time by the processor. Based on the fit to one or more the simulated reflectance curves in the database, the oximeter probe determines one or both of the absorption $\mu_a$ and reduced scattering $\mu_s'$ for the real tissue for one or both layers. From the absorption ($\mu_a$) values determined for one layer, the oximeter probe determines the oxygenated and deoxygenated hemoglobin concentrations for the tissue.

Figure 11A:
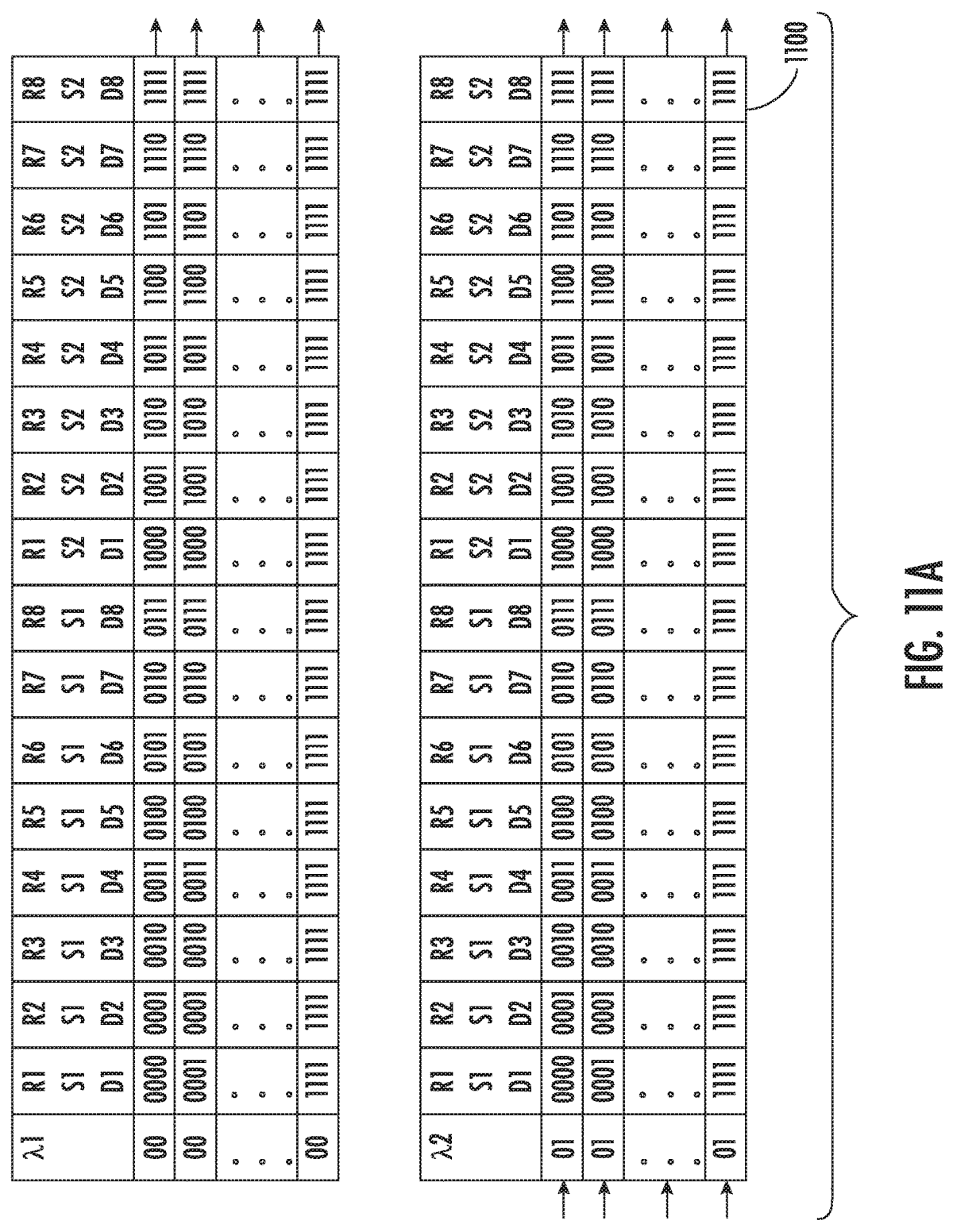

FIGS. 11A-11B show a database 1110 of simulated reflectance curves stored in the memory of the oximeter probe in an implementation. The database is for a layered model of tissue. Each row in the database includes simulated reflectance curves for each of four wavelengths of light emitted from the simulated source structures and detected by simulated detector structures. Each row of four simulated reflectance curves includes 16 values for each simulated reflectance curve. More specifically, each row includes 16 values for the 16 source-to-detector distances for source structures 120a-120b and detector structures 125a-125h. In total, each row includes 64 values for the four simulated reflectance curves for four wavelengths of light emitted from the two simulated source structures and detected by the eight simulated detector structures.

The layered model of tissue for database 1110 can include more or fewer simulated reflectance curves per row if more or fewer wavelengths are emitted from the source structures. Database 1110 can include more or fewer then 16 values for each of simulated reflectance curves if, for example, one or more than two source structure is included in the probe tip, more or fewer detector structures are included in the probe tip, or both.

Each of the four simulated reflectance curves for each row of database 1110 is associated with four tissue parameters, including melanin content, blood volume, scattering, and oxygen saturation (the fraction of oxygenated hemoglobin relative to total hemoglobin for tissue). More of fewer tissue parameters can be included in database 1110.

When a set of detector values that are generated by detector structures 125a-125h for tissue to be measured by the oximeter probe are fit by the processor to one or more of the rows, the oximeter probe thereby determines, in any combination, one or more of the tissue parameters such as melanin content, blood volume, scattering, and oxygen saturation. In an implementation, the oximeter probe is adapted to determine the oxygen saturation for the tissue and display a value for the oxygen saturation on the display.

As described briefly above, database 1110 includes simulated reflectance curves 315 for a layered tissue model. The layers of the simulated tissue can include the epidermis, the dermis, subcutaneous tissue, or any combination of one or more of these layers. The layers can include greater resolution of skin morphology such as the reticular dermis and superficial plexus. The Monte-Carlo simulations that generate the simulated reflectance curve can simulate the tissue for various chromophores included in the tissue layers. For example, the Monte-Carlo simulations can use a tissue model for the epidermis having various melanin contents, but might not use a tissue model for epidermis that includes blood. The Monte-Carlo simulations can use a tissue model for the dermis layer having various blood volumes and various oxygen saturations. In an implementation, the Monte-Carlo simulations do not use a tissue model for dermis that includes melanin. Similarly, the Monte-Carlo simulations can use a tissue model of adipose tissue having various blood volumes and various oxygen saturations. In an implementation, the Monte-Carlo simulations do not use a tissue model for adipose tissue that has melanin. The tissue models for the tissue layers can include concentrations for other tissue chromophores, such as water and fat where the concentrations for these chromophores are relatively typical physiological values.

In an implementation, the various chromophore concentrations that the Monte-Carlo simulations use for generating the simulated reflectance curves span a relatively large and relatively accurate range of actual physiological values present in real tissue. The number of values included in the ranges of actual physiological values can by varied to balance various parameters of tissue oximeter measurements. For example, the number of values used for the range of concentrations of the chromophores in simulated tissue can be relatively high or low and affect the accuracy of measurements made by the oximeter probe. In an implementation, 355 values are used in the Monte-Carlo simulations for the range of melanin content for light absorption in simulated epidermal tissue. In an implementation, 86 values are used in the Monte-Carlo simulations for the range of melanin content for light absorption in simulated dermal tissue. For scattering in both simulated epidermal tissue and simulated dermal tissue, 65 values are used in the Monte-Carlo simulations. In other implementations, the number of these values is different.

Figure 12A:
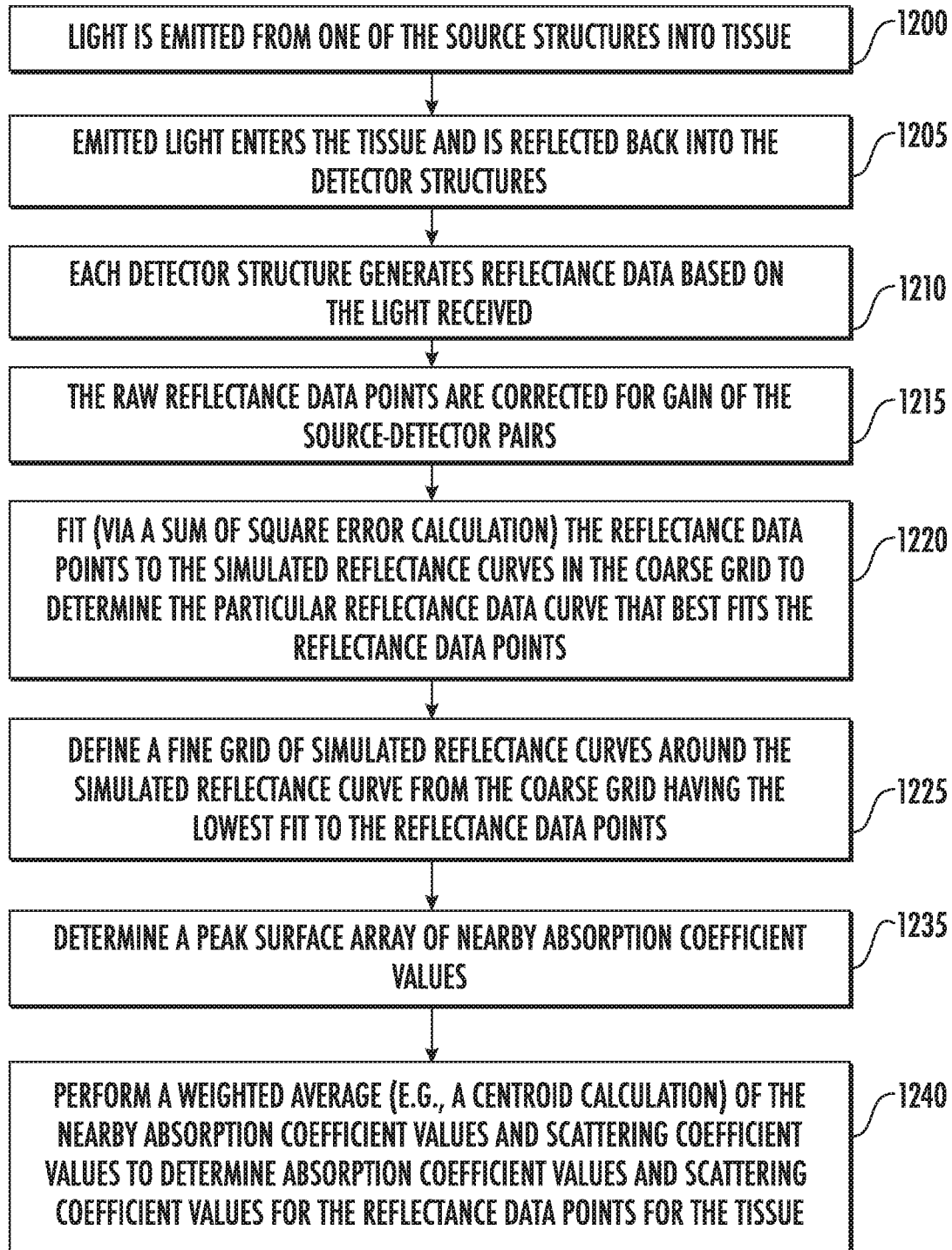
FIGS. 12A-12B show a flow diagram of a method for determining the optical properties of tissue (e.g., real tissue) by the oximeter probe where the oximeter probe uses reflectance data and the simulated reflectance curves to determine the optical properties.
Figure 12B:
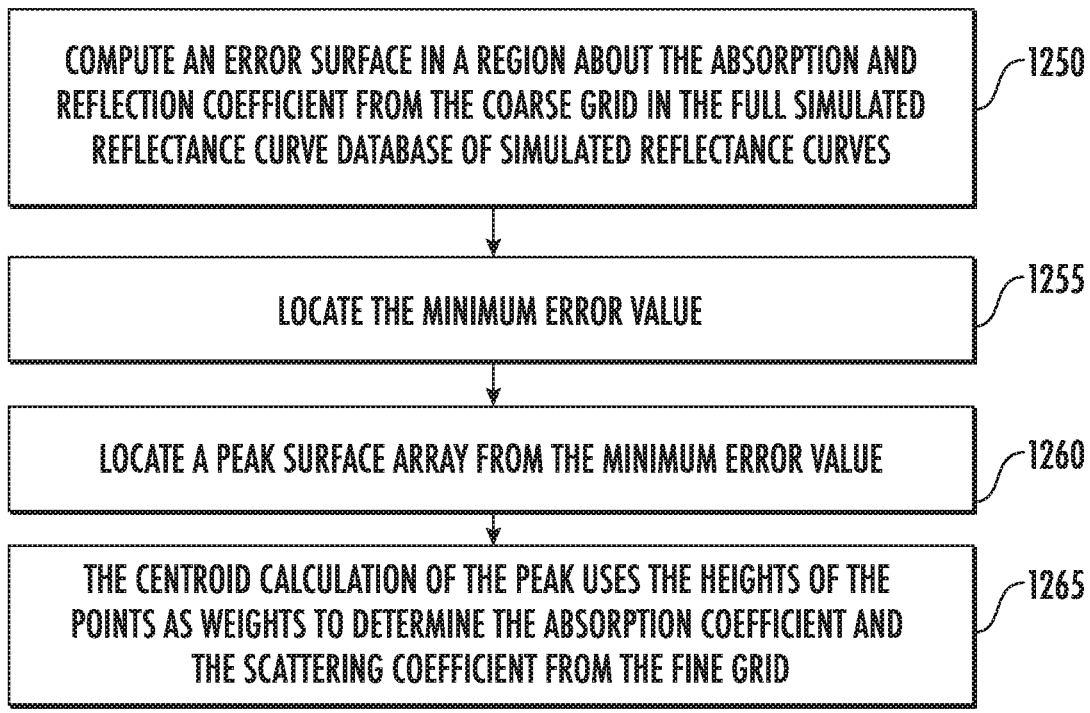

Tissue Analysis. FIGS. 12A-12B show a flow diagram of a method for determining the optical properties of tissue (e.g., skin) by oximeter probe 101 where the oximeter probe uses reflectance data and simulated reflectance curves 315 to determine the optical properties. The optical properties may include the absorption coefficient $\mu_a$ and the reduced scattering coefficient $\mu_s'$ of the tissue. A further method for conversion of the absorption coefficient $\mu_a$ of the tissue to oxygen saturation values for tissue is described in further detail below. The flow diagram represents one example implementation. Steps may be added to, removed from, or combined in the flow diagram without deviating from the scope of the implementation.

At 1200, oximeter probe 101 emits light (e.g., near infrared light) from one of the source structures 120, such as source structure 120a into tissue. The oximeter probe is generally in contact with the tissue when the light is emitted from the source structure. After the emitted light reflects from the tissue, detector structures 125 detect a portion this light, step 1205, and generate reflectance data points for the tissue, step 1210. Steps 1200, 1205, and 1210 may be repeated for multiple wavelengths of light (e.g., red, near infrared light, or both) and for one or more other source structures, such as source structure 120b. The reflectance data points for a single wavelength might include sixteen reflectance data points if, for example, tissue oximeter probe 115 has sixteen source-to-detector distances. The reflectance data points are sometimes referred to as an N-vector of the reflectance data points.

At 1215, the reflectance data points (e.g., raw reflectance data points) are corrected for gain of the source-detector pairs. During calibration of the source-detector pairs, gain corrections are generated for the source-detector pairs and are stored in memory 117. Generation of the gain corrections is described in further detail below.

At 1220, processor 116 fits (e.g., via a sum of squares error calculation) the reflectance data points to the simulated reflectance curves 315 to determine the particular reflectance data curve that best fits (i.e., has the lowest fit error) the reflectance data points. The database stored in the memory and fit to the reflectance data can be database 900, database 1000, or database 1100. In a specific implementation, a relatively small set of simulated reflectance curves that are a "coarse" grid of the database of the simulated reflectance curves is selected and utilized for fitting step 1220. For example, for database 900 given 39 scattering coefficient $\mu_s'$ values and 150 absorption coefficient $\mu_a$ values, a coarse grid of simulated reflectance curves might be determined by processor 116 by taking every 5th scattering coefficient $\mu_s'$ value and every 8th absorption coefficients $\mu_a$ for a total of 40 simulated reflectance curves in the coarse grid. It will be understood that the foregoing specific values are for an example implementation and that coarse grids of other sizes might be utilized by processor 116. The result of fitting the reflectance data points to the coarse grid is a coordinate in the coarse grid $(\mu_a, \mu_s')_{coarse}$ of the best fitting simulated reflectance curve. For database 1000, the coarse grid will cover absorption in each layer and reduced scattering. Each of the following steps for the method for database 1000 will be adjusted for $\mu_a$ of each layer and $\mu_s'$. For database 1100, the coarse grid will cover melanin content, oxygen saturation, blood volume, and scattering. Each of the following steps for the method for database 1100 will be adjusted for melanin content, oxygen saturation, blood volume, and scattering instead of $\mu_a$ and $\mu_s'$.

At 1225, the particular simulated reflectance curve from the coarse grid having the lowest fit error is utilized by processor 116 to define a "fine" grid of simulated reflectance curves where the simulated reflectance curves in the fine grid are around the simulated reflectance curve from the coarse grid having the lowest fit error.

That is, the fine grid is a defined size, with the lowest error simulated reflectance curve from the coarse grid defining the center of the fine grid. The fine grid may have the same number of simulated reflectance curves as the coarse grid or it may have more or fewer simulated reflectance curves. The fine grid has a fineness so as to provide a sufficient number of points to determine a peak surface array of nearby absorption coefficient $\mu_a$ values and scattering coefficient $\mu_s'$ values, step 1235, in the fine grid. Specifically, a threshold may be set by processor 116 utilizing the lowest error value from the coarse grid plus a specified offset. The positions of the scattering coefficient $\mu_s'$ and the absorption coefficient $\mu_a$ on the fine grid that have errors below the threshold may all be identified for use in determining the peak surface array for further determining the scattering coefficient $\mu_s'$ and the absorption coefficient $\mu_a$ for the reflectance data. Specifically, an error fit is made for the peak to determine the absorption coefficient $\mu_a$ and the scattering coefficient $\mu_s'$ values at the peak. A weighted average (e.g., a centroid calculation) of the absorption coefficient $\mu_a$ and the scattering coefficient $\mu_s'$ values at the peak may be utilized by the oximeter probe for the determination of the absorption coefficient $\mu_a$ and the scattering coefficient $\mu_s'$ values for the reflectance data points for the tissue, step 1240.

Weights for the absorption coefficient $\mu_a$ and the scattering coefficient $\mu_s'$ values for the weighted average may be determined by processor 116 as the threshold minus the fine grid error. Because points on the fine grid are selected with errors below the threshold, this gives positive weights. The weighted calculation of the weighted average (e.g., centroid calculation) renders the predicted scattering coefficient $\mu_s'$ and absorption coefficient $\mu_a$ (i.e., $(\mu_a, \mu_s')_{fine}$) for the reflectance data points for the tissue. Other methods may be utilized by the oximeter probe, such as fitting with one or more of a variety of non-linear least squares to determine the true minimum error peak for the absorption coefficient $\mu_a$.

In an implementation, processor 116 calculates the log of the reflectance data points and the simulated reflectance curves, and divides each log by the square root of the source-to-detector distances (e.g., in centimeters). These log values divided by the square root of the of the source-to-detector distances may be utilized by processor 116 for the reflectance data points and the simulated reflectance curves in the foregoing described steps (e.g., steps 1215, 1220, 1225, and 1230) to improve the fit of the reflectance data points to the simulated reflectance curves.

According to another implementation, the offset is set essentially to zero, which effectively gives an offset of the difference between the coarse grid minimum and the fine grid minimum. The method described above with respect to FIGS. 12A-12B relies on minimum fit error from the coarse grid, so the true minimum error on the fine grid is typically lower. Ideally, the threshold is determined from the lowest error on the fine grid, which would typically require additional computation by the processor.

The following is a further detailed description for finding the particular simulated reflectance curve that best fits the reflectance data points in the fine grid in an implementation. FIG. 12B shows a flow diagram of a method for finding the particular simulated reflectance curve that best fits the reflectance data points in the fine grid in an implementation. The flow diagram represents one example implementation. Steps may be added to, removed from, or combined in the flow diagram without deviating from the scope of the implementation.

Subsequent to determining the particular simulated reflectance curve $(\mu_a,\mu_s')_{coarse}$ from the coarse grid that best fits the reflectance data points at step 1225, processor 116 computes an error surface in a region about $(\mu_a,\mu_s')_{coarse}$ in the full simulated reflectance curve database (i.e., 16×5850 $(\mu_a,\mu_s')$ database) of simulated reflectance curves, step 1250. The error surface is denoted as: $\text{err}(\mu_a,\mu_s')$. Thereafter, processor 116 locates the minimum error value in $\text{err}(\mu_a,\mu_s')$, which is referred to as $\text{err}_{min}$, step 1255. Processor 116 then generates a peak surface array from $\text{err}(\mu_a,\mu_s')$ that is denoted by $\text{pksurf}(\mu_a,\mu_s')=k+\text{err}_{min}-\text{err}(\mu_a,\mu_s')$ if the peak surface is greater than zero, or $\text{pksurf}(\mu_a,\mu_s')=k+\text{err}_{min}-\text{err}(\mu_a,\mu_s')=0$ if the peak surface is less than or equal to zero, step 1260. In the expression k is chosen from a peak at the minimum point of $\text{err}(\mu_a,\mu_s')$ with a width above zero of approximately ten elements. The center-of-mass (i.e., the centroid calculation) of the peak in pksurf $(\mu_a,\mu_s')$ uses the heights of the points as weights, step 1265. The position of the center-of-mass is the interpolated result for the absorption coefficient $\mu_a$ and the scattering coefficient $\mu_s'$ for the reflectance data points for the tissue The method described above with respect to FIGS. 12A and 12B for determining the absorption coefficient $\mu_a$ and the scattering coefficient $\mu_s'$ for reflectance data points for tissue may be repeated for each of the wavelengths (e.g., 3 or 4 wavelengths) generated by each of source structures 120.

Oxygen Saturation Determination. According to a first implementation, processor 116 determines the oxygen saturation for tissue that is probed by oximeter probe 101 by utilizing the absorption coefficients $\mu_a$ (e.g., 3 or 4 absorption coefficients $\mu_a$) that are determined (as described above) for the 3 or 4 wavelengths of light that are generated by each source structure 120. According to a first implementation, a look-up table of oxygen saturation values is generated for finding the best fit of the absorption coefficients $\mu_a$ to the oxygen saturation. The look-up table may be generated by assuming a range of likely total hemoglobin, melanin, and oxygen saturation values and calculating $\mu_a$ for each of these scenarios. Then, the absorption coefficient $\mu_a$ points are converted to a unit vector by dividing by a norm of the unit vector to reduce systematic error and only depend on relative shape of curve. Then the unit vector is compared to the look-up table to find the best fit, which gives the oxygen saturation.

According to a second implementation, processor 116 determines the oxygen saturation for the tissue by calculating the net analyte signal (NAS) of deoxygenated hemoglobin and oxygenated hemoglobin. The NAS is defined as the portion of the spectrum that is orthogonal to the other spectral components in the system. For example, the NAS of deoxygenated hemoglobin in a system that also contains oxygenated hemoglobin and deoxygenated hemoglobin is the portion of the spectrum that is orthogonal to the oxygenated hemoglobin spectrum and the melanin spectrum. The concentrations of deoxygenated and oxygenated hemoglobin can be calculated by vector multiplying the respective NAS by the previously determined absorption coefficients at each wavelength. Oxygen saturation is then readily calculated as the concentration of oxygenated hemoglobin divided by the sum of oxygenated hemoglobin and deoxygenated hemoglobin. Anal. Chem. 58:1167-1172 (1986) by Lorber is incorporated by reference and provides a framework for a further detailed understanding of the second implementation for determining the oxygen saturation for the tissue.

In an implementation of oximeter probe 101, the reflectance data is generated by detector structures 125 at 30 Hertz, and oxygen saturation values are calculated at approximately 3 Hertz. A running average of determined oxygen saturation values (e.g., at least three oxygen saturation values) may be displayed on display 115, which might have an update rate of 1 Hertz.

Optical Properties. As described briefly above, each simulated reflectance curve 315 that is stored in memory 117 represents unique optical properties of tissue. More specifically, the unique shapes of the simulated reflectance curves, for a given wavelength, represent unique values of the optical properties of tissue, namely the scattering coefficient $(\mu_s)$, the absorption coefficient $(\mu_a)$, the anisotropy of the tissue (g), and index of refraction of the tissue from which the tissue properties may be determined.

The reflectance detected by detector structures 125 for relatively small source-to-detector distances is primarily dependent on the reduced scattering coefficient, $\mu_s'$. The reduced scattering coefficient is a "lumped" property that incorporates the scattering coefficient $\mu_s$ and the anisotropy g of the tissue where $\mu_s'=\mu_s(1-g)$, and is used to describe the diffusion of photons in a random walk of many steps of size of $1/\mu_s'$ where each step involves isotropic scattering. Such a description is equivalent to a description of photon movement using many small steps $1/\mu_s$ which each involve only a partial deflection angle if there are many scattering events before an absorption event, i.e., $\mu_a \ll \mu_s'$.

In contrast, the reflectance that is detected by detector structures 125 for relatively large source-to-detector distances is primarily dependent on the effective absorption coefficient $\mu_{eff}$, which is defined as $\sqrt{3\mu_a(\mu_a+\mu_s')}$, which is a function of both $\mu_a$ and $\mu_s'$.

Thus, by measuring reflectance at relatively small source-to-detector distances (e.g., S1-D4 and S2-D8 of FIG. 2) and relatively large source-to-detector distances (e.g., S1-D8 and S2-D4 of FIG. 2), both $\mu_a$ and $\mu_s'$ can be independently determined from one another. The optical properties of the tissue can in turn provide sufficient information for the calculation of oxygenated hemoglobin and deoxygenated hemoglobin concentrations and hence the oxygen saturation of the tissue.

Figure 13:
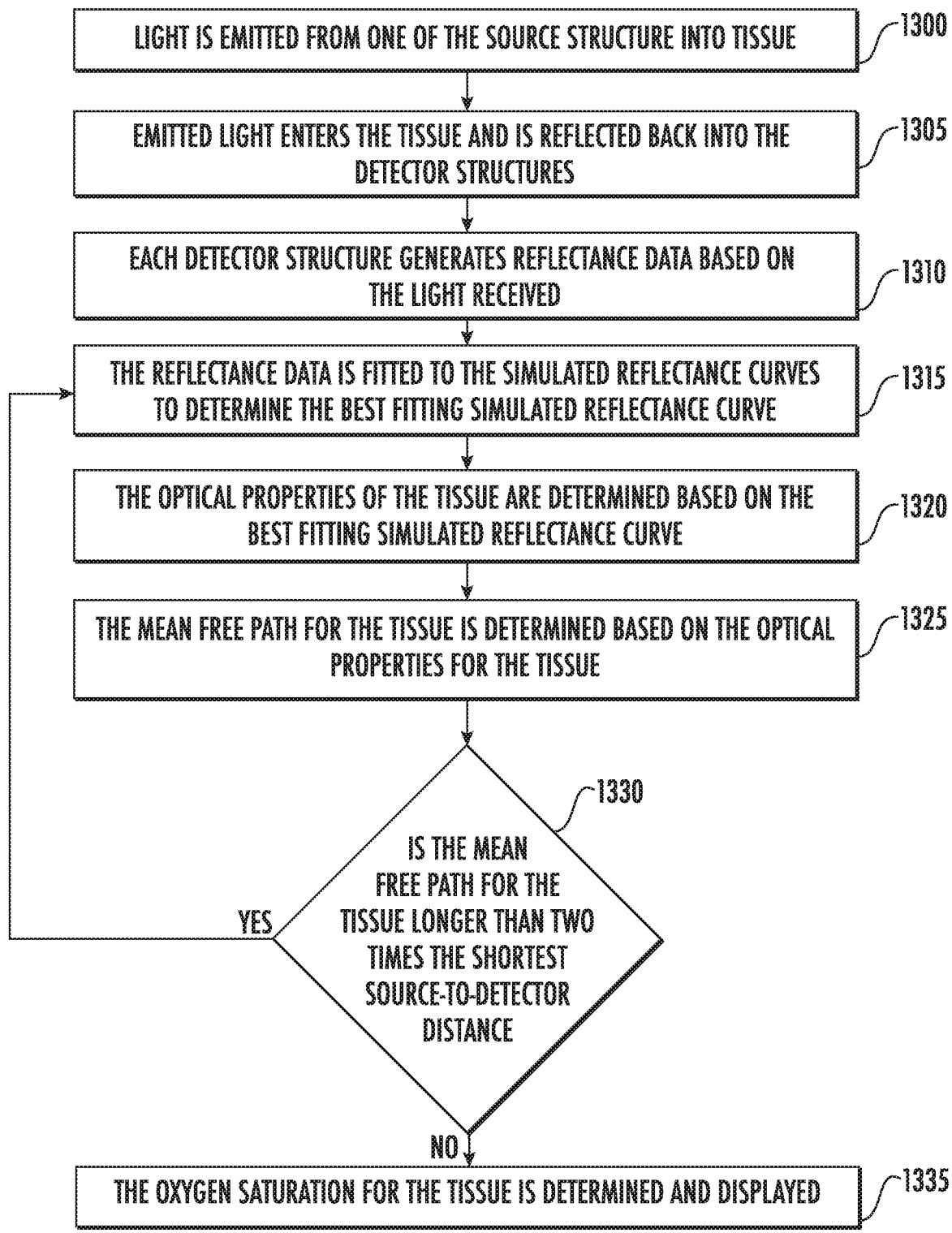
FIG. 13 shows a flow diagram of another method for determining the optical properties of tissue by the oximeter probe.

Iterative Fit for Data Collection Optimization. FIG. 13 shows a flow diagram of another method for determining the optical properties of tissue by oximeter probe 101. The flow diagram represents one example implementation. Steps may be added to, removed from, or combined in the flow diagram without deviating from the scope of the implementation.

At 1300, oximeter probe 101 emits light (e.g., near infrared light) from one of the source structures, such as source structure 120a into tissue. After the emitted light reflects from the tissue, detector structures 125 detect the light, step 1305, and generate reflectance data for the tissue, step 1310. Steps 1300, 1305, and 1310 may be repeated for multiple wavelengths of light and for one or more other source structures, such as source structure 120b. At 1315, oximeter probe 101 fits the reflectance data to simulated reflectance curves 315 and determines the simulated reflectance curve to which the reflectance data has the best fit. The database stored in the memory and fit to the reflectance data can be database 900, database 1000, or database 1100. Thereafter, oximeter probe 101 determines the optical properties (e.g., $\mu_a$, and $\mu_s'$ for database 900 or database 1000, or melanin content, oxygen saturation, blood volume, and scattering for database 1100) for the tissue based on the optical properties of the simulated reflectance curve that best fits the reflectance data, step 1320.

At 1325 oximeter probe 101 determines the mean free path of the light in the tissue from the optical properties (e.g., mfp=$1/(\mu_a,\mu_s')$) determined at step 1320. Specifically, the mean free path can be determined from the optical properties obtained from a cumulative reflectance curve that includes the reflectance data for all of the source-detector pairs (e.g., pair 1: source structure 120a and detector structure 125a; pair 2: source structure 120a and detector structure 125b; pair 3: source structure 120a and detector structure 125c; pair 4: source structure 120a and detector structure 125d; pair 5: source structure 120a and detector structure 125e; pair 6: source structure 120a and detector structure 125f; pair 7: source structure 120a and detector structure 125g; pair 8: source structure 120a and detector structure 125h; pair 9: source structure 120b and detector structure 125a, pair 10: source structure 120b and detector structure 125b . . . and others).

At 1330, oximeter probe 101 determines whether the mean free path calculated for a given region of the tissue is longer than two times the shortest source-to-detector distance (e.g., S1-D4 and S2-D8 of FIG. 2). If the mean free path is longer than two times the shortest source-to-detector distance, then the collected reflectance data is re-fitted to the simulated reflectance curves (i.e., reanalyzed) without utilizing the reflectance data collected from the detector structures for the source-to-detector pairs having the shortest source-to-detector distance. For example, steps 1315-1330 are repeated without use of the reflectance data from detector structure 125e with source structure 120a acting as the source for detector structure 125d, and without use of the reflectance data from detector structure 125h with source structure 120b acting as the source for detector structure 125h. The process of calculating the mean free path and discarding the reflectance data for one or more source-detector pairs may be repeated until no source-detector pairs that contribute reflectance data to the fit have a source-to-detector distance shorter than one half of the calculated mean free path. Thereafter, oxygen saturation is determined from the best fitting simulated reflectance curve and reported by oximeter probe 101, such as on display 115, step 1335.

Light that is emitted from one of the source structures 120 into tissue and that travels less than half of the mean free path is nondiffusely reflected. The re-emission distance for this light is strongly dependent on the tissue phase function and the local tissue composition. Therefore, using the reflectance data for this light tends to result in a less accurate determination of the optical properties and tissue properties as compared with the reflectance data for light that has undergone multiple scattering events.

Data Weighting Detector Structures. Detector structures 125 that are positioned at increasing distances from source structures 120 receive decreasing amounts of reflectance from tissue. Therefore, the reflectance data generated by detector structures 125 having relatively short source-to-detector distances (e.g., S1-D4 and S2-D8 of FIG. 2) tends to exhibit intrinsically higher signal compared to reflectance data generated by detector structures having relatively long source-to-detector distances (e.g., S1-D8 and S2-D4 of FIG. 2). Fit algorithms may therefore preferentially fit the simulated reflectance curves to the reflectance data that is generated by detector structures 125 having relatively short source-to-detectors distances (e.g., source-to-detector distances less than or equal to the average distance between the source structures and the detector structures) more tightly than reflectance data that is generated by detector structures having relatively long source-to-detector distances (e.g., source-to-detector distances greater than the average distance). For relatively accurate determination of the optical properties from the reflectance data, this distance-proportional skew may be undesirable and may be corrected by weighting the reflectance data as described immediately below.

Figure 14:
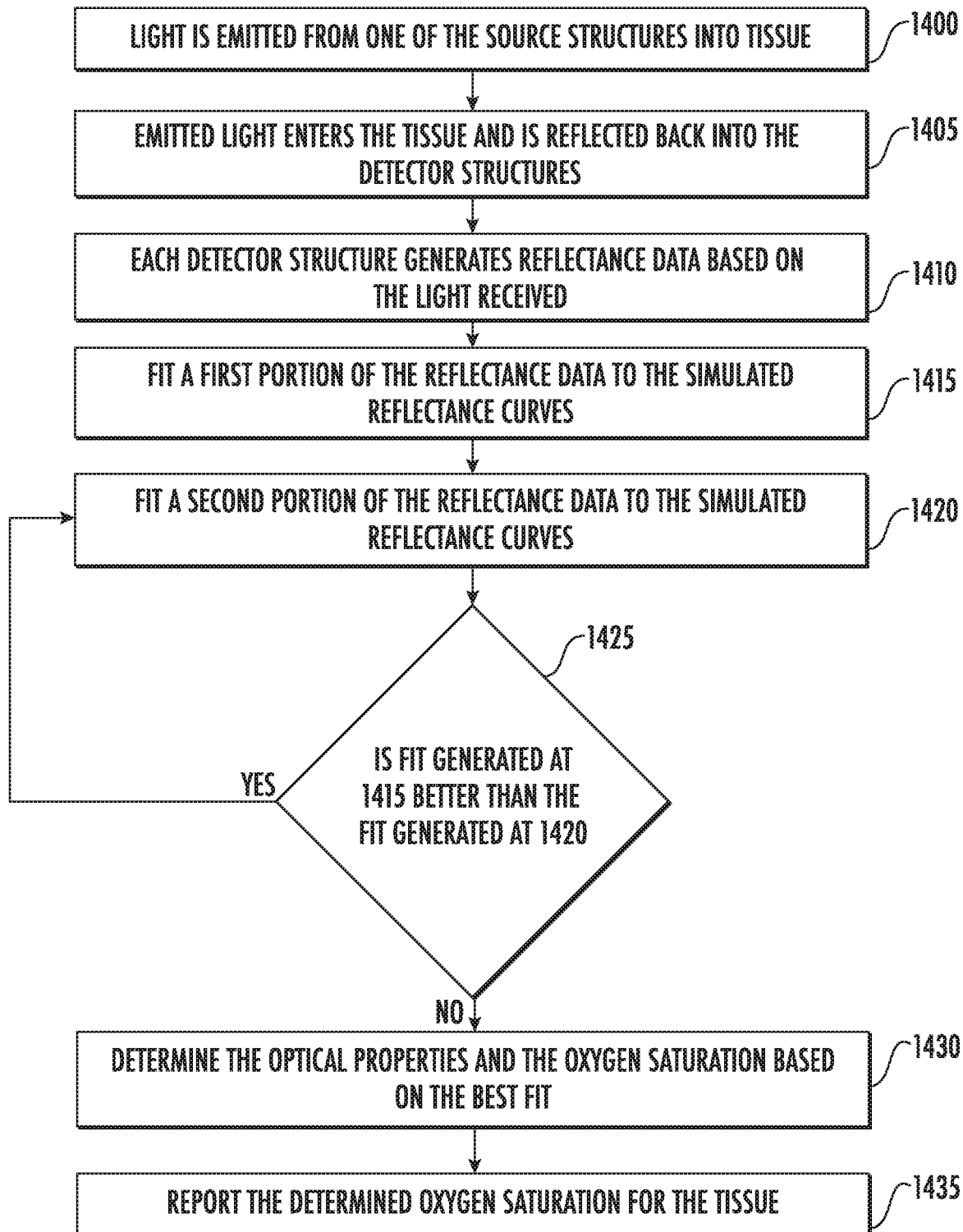
FIG. 14 shows a flow diagram of a method for weighting reflectance data generated by select detector structures.

FIG. 14 shows a flow diagram of a method for weighting reflectance data generated by select detector structures 125. The flow diagram represents one example implementation. Steps may be added to, removed from, or combined in the flow diagram without deviating from the scope of the implementation.

At 1400, oximeter probe 101 emits light from one of the source structures, such as source structure 120a into tissue. After the emitted light reflects from the tissue, detector structures 125 detect the light, step 1405, and generate reflectance data for the tissue, step 1410. Steps 1400, 1405, and 1410 may be repeated for multiple wavelengths of light and for one or more other source structures, such as source structure 120b. At 1415, oximeter probe 101 fits a first portion of the reflectance data to the simulated reflectance curves 315. The database stored in the memory and fit to the reflectance data can be database 900, database 1000, or database 1100. The first portion of the reflectance data is generated by a first portion of detector structures that are less than a threshold distance from the source structure. The threshold distance may be the average distances (e.g., approximate midrange distance) between the source structures and the detector structures. At 1420, reflectance data for a second portion of the reflectance data is fitted to the simulated reflectance curves. The second portion of reflectance data is generated by the first portion of the detector structures and another detector structure that is at the next largest source-to-detector distance from the source compared to the threshold distance. For example, if the first portion of detector structures includes detector structures 125c, 125d, 125e, and 125f, then the detector structure that is at the next largest source-to-detector distance is detector structure 125g (see table 1).

At 1425, the fit generated at step 1415 is compared to the fit generated at step 1420 to determine whether the fit generated at step 1420 is better than the fit generated at 1415. As will be understood by those of skill in the art, a "closeness" of a fit of data to a curve is quantifiable based on a variety of parameters, and the closeness of fits are directly comparable to determine the data having a closer fit (closer fit) to a curve. As will be further understood, a closer fit is sometimes also referred to as a better fit or a tighter fit. If the fit generated at step 1420 is better than the fit generated at step 1415, then steps 1420 and 1425 are repeated with reflectance data that is generated by detector structures that include an additional detector structure (according to the example being considered, detector structure 125c) that is positioned at a next increased source-to-detector distance from the source. Alternatively, if the fit generated at step 1420 is not better than the fit generated at step 1415, then the reflectance data for detector structures 125 that are positioned at source-to-detector distances that are greater than the threshold distance are not used in the fit. Thereafter, oximeter probe 101 uses the fit generated at 1415 or step 1420 (if better than the fit determined at step 1415) to determine the optical properties and the oxygen saturation of the tissue, step 1430. Thereafter, oxygen saturation is reported by oximeter probe 101, such as on display 115, step 1435.

According to an alternative implementation, if the fit generated at step 1420 is not better than the fit generated at step 1415, then the reflectance data are weighted by a weighting factor for detector structures that have source-to-detector distances that are greater than the threshold distance so that this weighted reflectance data has a decreased influence on the fit. Reflectance data that is not used in a fit may be considered as having a zero weight and may be associated with reflectance from tissue below the tissue layer of interest. Reflectance from tissue below the tissue layer of interest is said to exhibit a characteristic kink in the reflectance curve that indicates this particular reflectance.

It is noted that curve-fitting algorithms that fit the reflectance data to the simulated reflectance curves may take into account the amount of uncertainty of the reflectance data as well as the absolute location of the reflectance data. Uncertainty in the reflectance data corresponds to the amount of noise from the generation of the reflectance data by one of the detector structures, and the amount of noise can scale as the square root of the magnitude of the reflectance data.

According to a further implementation, oximeter probe 101 iteratively weights the reflectance data based on the amount of noise associated with the measurements of the reflectance data. Specifically, the reflectance data generated by detector structures having relatively large source-to-detector distances generally have lower signal-to-noise ratio compared to the reflectance data generated by detector structure having relatively short source-to-detector distances. Weighting the reflectance data generated by detector structures having relatively large source-to-detector distances allows for this data to contribute to the fit equally or approximately equally to other reflectance data.

Methods described for matching reflectance data to a number of Monte-Carlo-simulated reflectance curves provide for relatively fast and accurate determination of the optical properties of real tissue probed by the oximeter probe. Speed in determining optical properties of tissue is an important consideration in the design of intraoperative probes compared to postoperative probes. Further, the Monte-Carlo methods described allow for robust calibration methods that in-turn allow for the generation of absolute optical properties as compared with relative optical properties. Reporting absolute optical properties, as opposed to relative optical properties, is relatively important for intraoperative oximeter probes as compared with post-operative oximeter probes.

Figure 15:
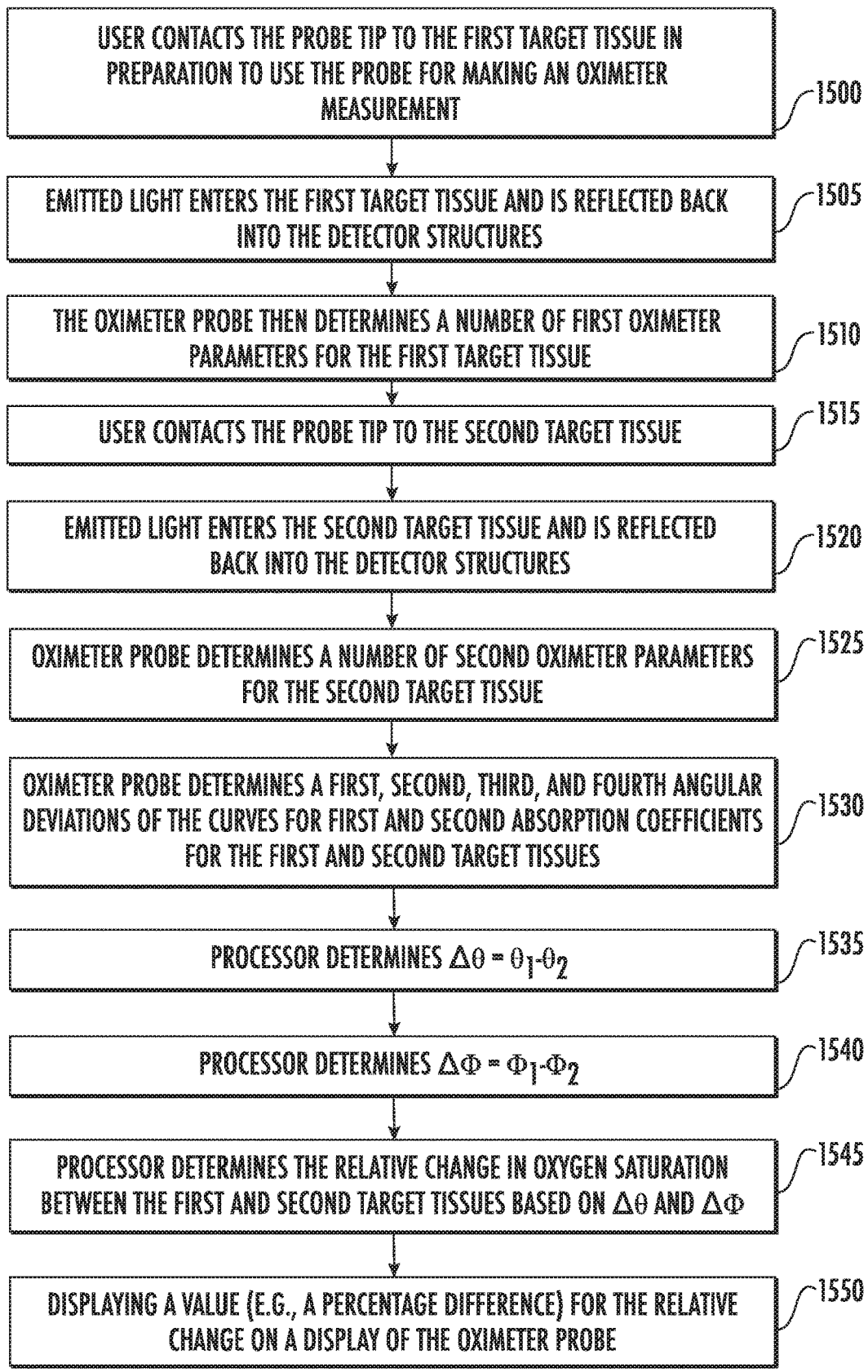
FIG. 15 shows a flow diagram of a method for determining relative tissue parameters for tissue measured by the oximeter probe where contributions from melanin in the tissue are removed from the relative tissue parameters.

FIG. 15 shows a flow diagram of a method for determining relative tissue parameters for tissue measured by the oximeter probe where contributions from melanin in the tissue are removed from the relative tissue parameters. The flow diagram represents one example implementation. Steps may be added to, removed from, or combined in the flow diagram without deviating from the scope of the implementation.

The method includes making oximeter measurements on different tissue locations (e.g., first and second target tissues) of a patient's body, and using the oximeter measurements to determine a relative tissue parameter for one of the target tissues (e.g., the second target tissue). The different target locations can be tissues that have the same or similar melanin concentrations, such as contralateral tissues. For example, during a breast reconstruction surgery (e.g., where a tissue flap is being used in the reconstruction), the first target tissue may be healthy breast tissue and the second target tissue may be tissue for which an oximeter reading is desired (e.g., the breast that is being reconstructed). The first breast tissue can be from the same breast or different breast or other tissue, such as other chest tissue. The two tissues should have the same or similar melanin content. The oximeter measurements for the first and second target tissue are then used to generate a relative tissue parameter (e.g., relative oxygen saturation value) that is the difference between a first tissue parameter (e.g., first oxygen saturation) of the first target tissue (e.g., healthy breast tissue) and second tissue parameter (e.g., second oxygen saturation) of the second target tissue (e.g., tissue flap being used for the reconstruction or the breast tissue being reconstructed) where contributions from the light absorption by melanin is removed from the measure for the relative oxygen saturation.

As described further below, the method exploits the approximately constant slope of the curve of the absorption coefficients of melanin in tissue for light having wavelengths from about 700 nanometers to about 900 nanometers (e.g., infrared wavelengths). The method uses a derivative approach of the absorption coefficients to remove the melanin contributions (e.g., from light absorption by melanin) from the oximetry measurements and determinations (e.g., final results, intermediary results, or both). See the slope for the absorption coefficients of melanin in FIG. 8. The method also exploits the differences in the slope of the curves for the absorption coefficients of melanin and oxygenated blood hemoglobin and the differences in the slope of the curves of the absorptions coefficients of melanin and deoxygenated blood hemoglobin. See the curves for the absorption coefficients of oxygenated and deoxygenated hemoglobin in FIG. 8. Also, as further explained below, the method exploits the changes in the slopes of curves for the absorptions coefficients for the first and second target tissues where these tissues may have different concentrations of oxygenated and deoxygenated hemoglobin.

In an implementation of the method, a user contacts the probe tip of the oximeter probe to the first target tissue at a first location (e.g., different location from the second target tissue) in preparation to use the probe for making an oximeter measurement. See 1500 in FIG. 15. Thereafter, the oximeter probe emits light (e.g., 2, 3, 4, or more wavelengths of IR) from one or more of the source structures (e.g., two source structures) on the probe face into the first target tissue. The detector structures on the probe face detect the light subsequent to reflection from or transmission through the first target tissue and generate first reflectance data based on the detected light. The first reflectance data includes a first melanin absorption component of reflectance data for melanin content (e.g., first melanin content for the first target tissue) of the first target tissue. See 1505 in FIG. 15.

The oximeter probe then determines a number of first oximeter parameters for the first target tissue using the first reflectance data for each wavelength of light transmitted from the source structures into the tissue. See 1510 in FIG. 15. The first oximeter parameters can be determined by the oximeter probe by fitting the reflectance data to the simulated reflectance curves as described above. The oximeter probe stores these first oximeter parameters in the memory of the probe. The first oximeter parameters can be values for the absorption coefficients for each of the transmitted wavelengths of light for the first target tissue. The first oximeter parameters for the first target tissue (e.g., healthy tissue) are baseline parameters. The first oximeter parameters (e.g., intermediary values, such as angular measure, absorptions coefficients, oxygen saturation values, other values) may be unavailable for display after the first measurement is made and before a second measurement is made (e.g., described below at 1515, 1520, and 1525 of FIG. 15).

FIGS. 16A and 16B show example graphs of absorption coefficients for the first target tissue and the second target tissue illuminated by a number of light wavelengths, such as the 760 nanometers, 810 nanometers, 845 nanometers, and 895 nanometers. Other wavelengths can be used by the oximeter probe including more or fewer wavelengths of light.

At 1515, the user moves the probe face of the oximeter probe to the second target tissue (e.g., breast tissue undergoing reconstructive surgery). Thereafter, the oximeter probe emits light (e.g., 2, 3, 4, or more wavelengths of IR) from the one or more source structures on the probe face into the second target tissue. The detector structures on the probe face detect the light subsequent to reflection from or transmission through the second target tissue and generate second reflectance data based on the detected light. The second reflectance data includes a second melanin absorption component of reflectance data for melanin content (e.g., second melanin content for the first target tissue) of the second target tissue. See 1520 in FIG. 15.

The oximeter probe then determines a number of second oximeter parameters for the second target tissue using the second reflectance data for each wavelength of light transmitted from the source structures into the tissue. See 1525 in FIG. 15. The second oximeter parameters can be determined by the oximeter probe by fitting the second reflectance data to the simulated reflectance curves as described above. The oximeter probe can store these second oximeter parameters in the memory of the probe. The second oximeter parameters can be values for the absorption coefficients for the transmitted wavelengths of light for the second target tissue.

At 1530, the oximeter probe, determines a first angular deviation $\theta_1$ (see FIG. 16A) of the first curve (e.g., lines forming the curves) for first absorption coefficients for line 1605 (e.g., the projection 1605a of line 1605 which is shown as a broken line in FIG. 16A) between 760 nanometers and 810 nanometers and 1410 between 810 nanometers and 845 nanometers.

The oximeter probe, determines a second angular deviation $\Phi_1$ of the first curve (e.g., lines forming the curves) for the second absorption coefficients for line 1610 (e.g., the projection 1610a of line 1610 which is shown as a broken line in FIG. 16A) between 810 nanometers and 845 nanometers and line 1615 between 845 nanometers and 890 nanometers.

The oximeter probe, determines a third angular deviation $\theta_2$ (see FIG. 16B) of the second curve (e.g., lines forming the curves) for the second absorption coefficients for line 1620 (e.g., the projection 1620a of line 1620 which is shown as a broken line in FIG. 16B) between 760 nanometers and 810 nanometers and line 1625 between 810 nanometers and 845 nanometers.

The oximeter probe, determines a fourth angular deviation $\Phi_2$ of the second curve (e.g., lines forming the curves) for the second absorption coefficients for line 1625 (e.g., the projection 1625a of line 1625 which is shown as a broken line in FIG. 16B) between 810 nanometers and 845 nanometers and line 1630 between 845 nanometers and 890 nanometers.

The first and second angular deviations $\theta_1$ and $\Phi_1$ shown in FIG. 16A are calculated by the oximeter probe by taking the second derivative of the first curve for the absorption coefficients with respect to wavelength for the first target tissue (e.g., healthy breast tissue). The third and fourth angular deviations $\theta_2$ and $\Phi_2$ shown in FIG. 16B are calculated by the oximeter probe by taking the second derivative of the first curve for the absorption coefficients with respect to wavelength for the second target tissue (e.g., reconstructed breast tissue).

Figure 17A:
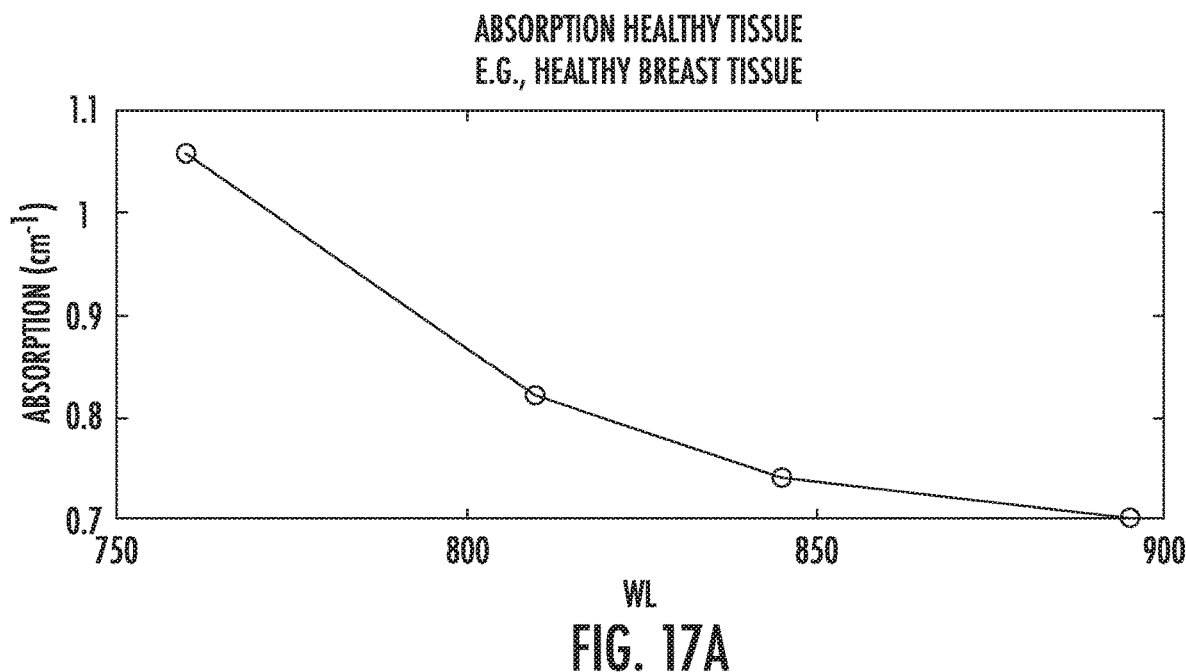
FIG. 17A shows an example curve of the absorption coefficients for the second target tissue (e.g., breast being reconstructed). The example curve has a negative slope along the entire length of the curve.
Figure 17B:
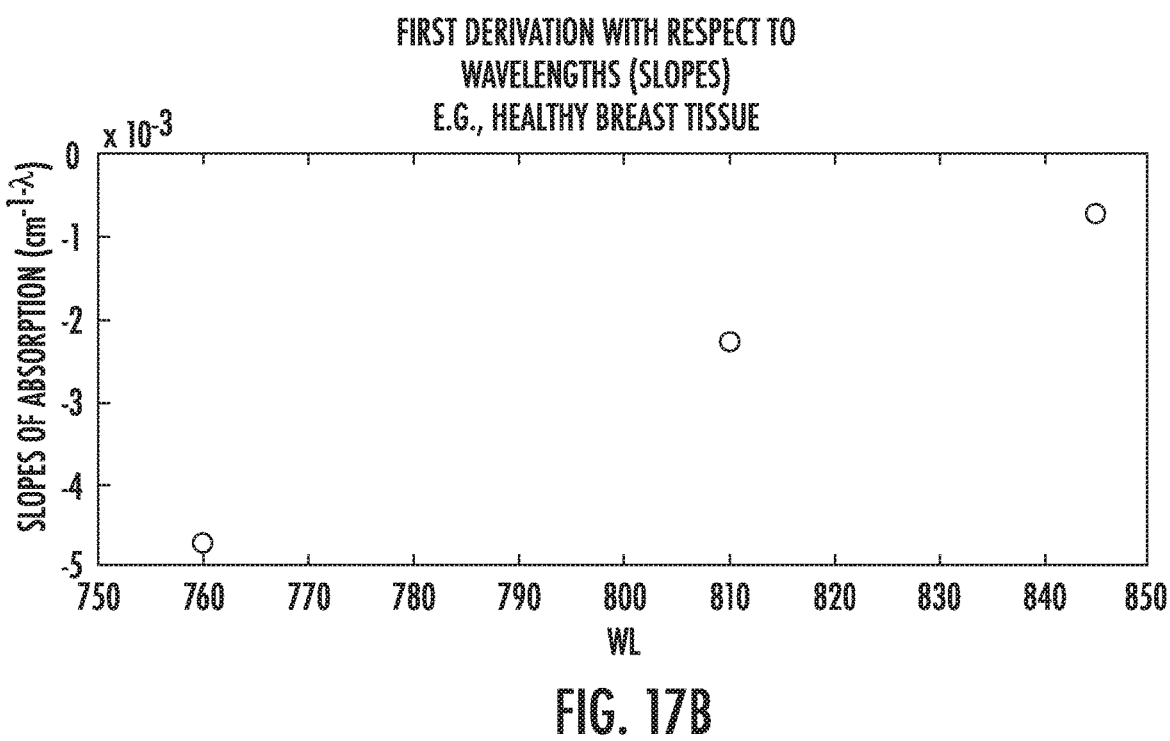
FIG. 17B shows an example curve of the first derivative of the absorption coefficients with respect to wavelength for the first target site.
Figure 17C:
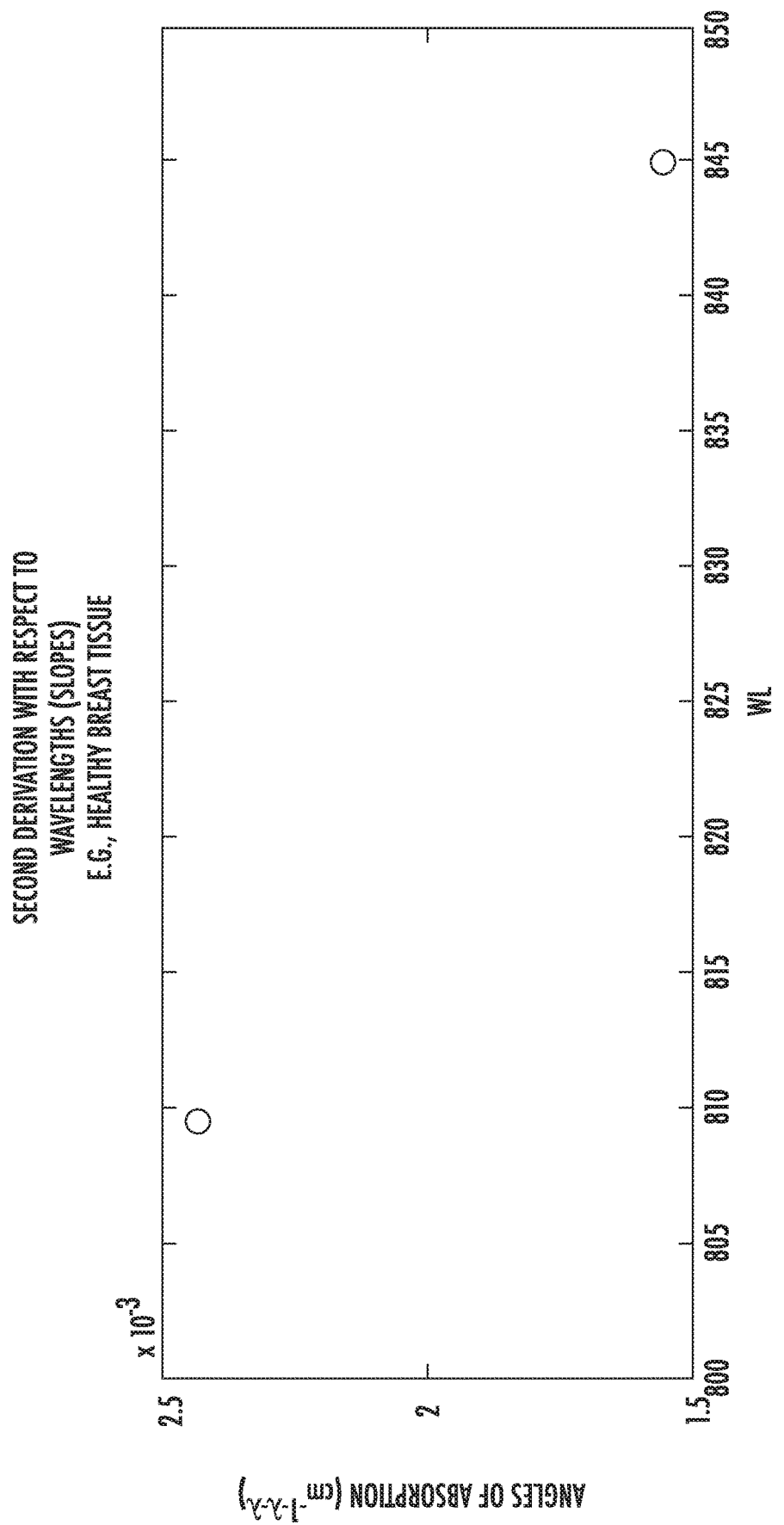
FIG. 17C shows an example curve of the second derivative of the absorption coefficients with respect to wavelength for the first target site.

FIG. 17A shows an example curve (e.g., first spectrum) of the absorption coefficients for the first target tissue (e.g., healthy breast tissue). The example curve has a negative slope along the entire length of the curve. FIG. 17B shows an example curve of the first derivative of the absorption coefficients with respect to wavelength for the first target tissue. The plot in FIG. 17B is for wavelengths of between 750 and 850. The negative values of the example curve of FIG. 17B match the negative slope shown in FIG. 17A, and the example curve has a positive slope along the entire length of the curve. FIG. 17C shows an example curve of the second derivative of the absorption coefficients with respect to wavelength for the first target site. The plot in FIG. 17C is for wavelengths of between 800 and 850 nanometers (e.g., specifically for 810 nanometers and 845 nanometers). The positive values of the example curve shown in FIG. 17C match the positive slope of the curve in FIG. 17B.

Figure 17D:
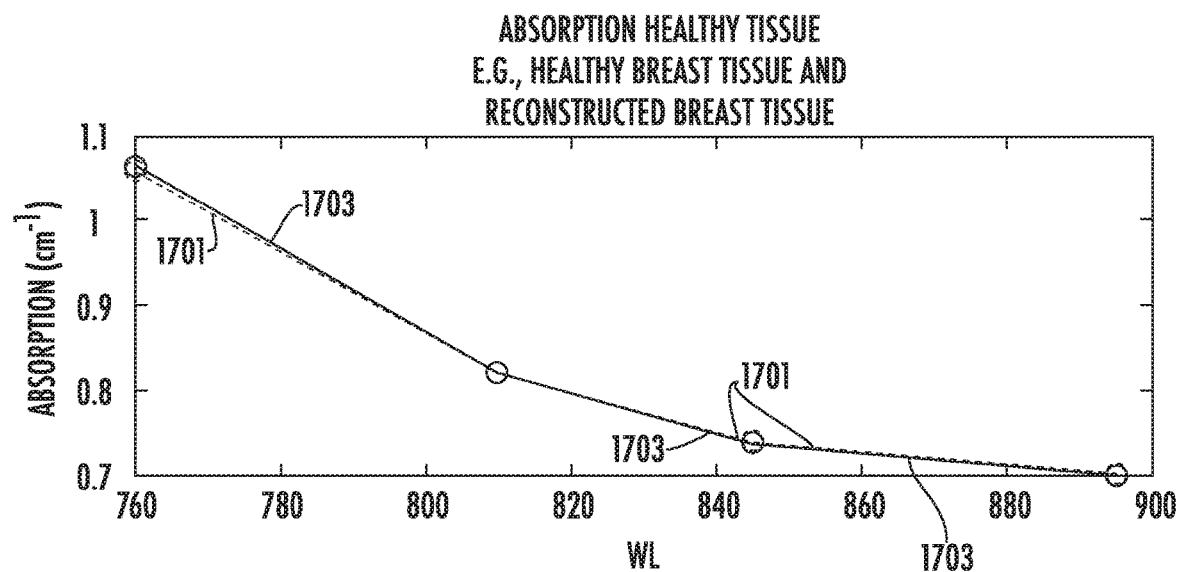
FIG. 17D shows an example first curve (e.g., first spectrum) and an example second curve (e.g., second spectrum) of the absorption coefficients for the first target tissue (e.g., healthy breast tissue) and the second target tissue (e.g., reconstructed breast tissue).

FIG. 17D shows an example first curve (e.g., first spectrum) 1701 and an example second curve (e.g., second spectrum) 1703 of the absorption coefficients for the first target tissue (e.g., healthy breast tissue) and the second target tissue (e.g., reconstructed breast tissue). The relatively small displacement of the curves indicates the relatively small change in the absorption coefficients between a first target tissue and a second target tissue. The example curves each has a negative slope along the entire length of the curve.

Figure 17E:
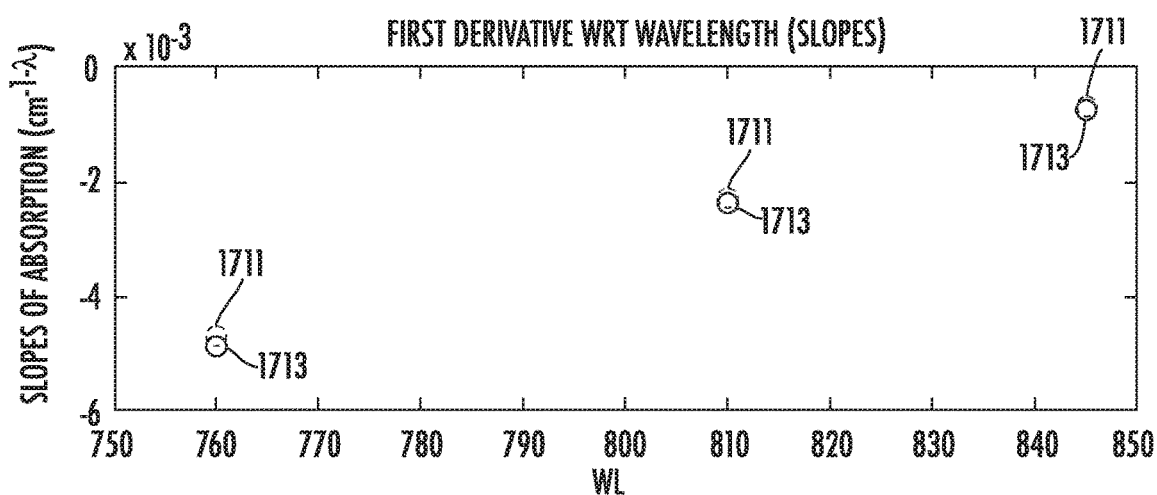
FIG. 17E shows a first example plot (e.g., three top points) of the first derivative of the absorption coefficients with respect to wavelength for the first target tissue and shows a second plot (e.g., three bottom points) of the first derivative of the absorption coefficients with respect to wavelength for the second target tissue.

FIG. 17E shows a first example plot 1711 (e.g., three top points) of the first derivative of the absorption coefficients with respect to wavelength for the first target tissue and shows a second plot 1713 (e.g., three bottom points) of the first derivative of the absorption coefficients with respect to wavelength for the second target tissue. The plot in FIG. 17E is for wavelengths of between 750 and 850. The negative values of the example plots of FIG. 17E match the negative slopes shown in FIG. 17D, and the example curves have positive slopes along the entire lengths of the curves.

Figure 17F:
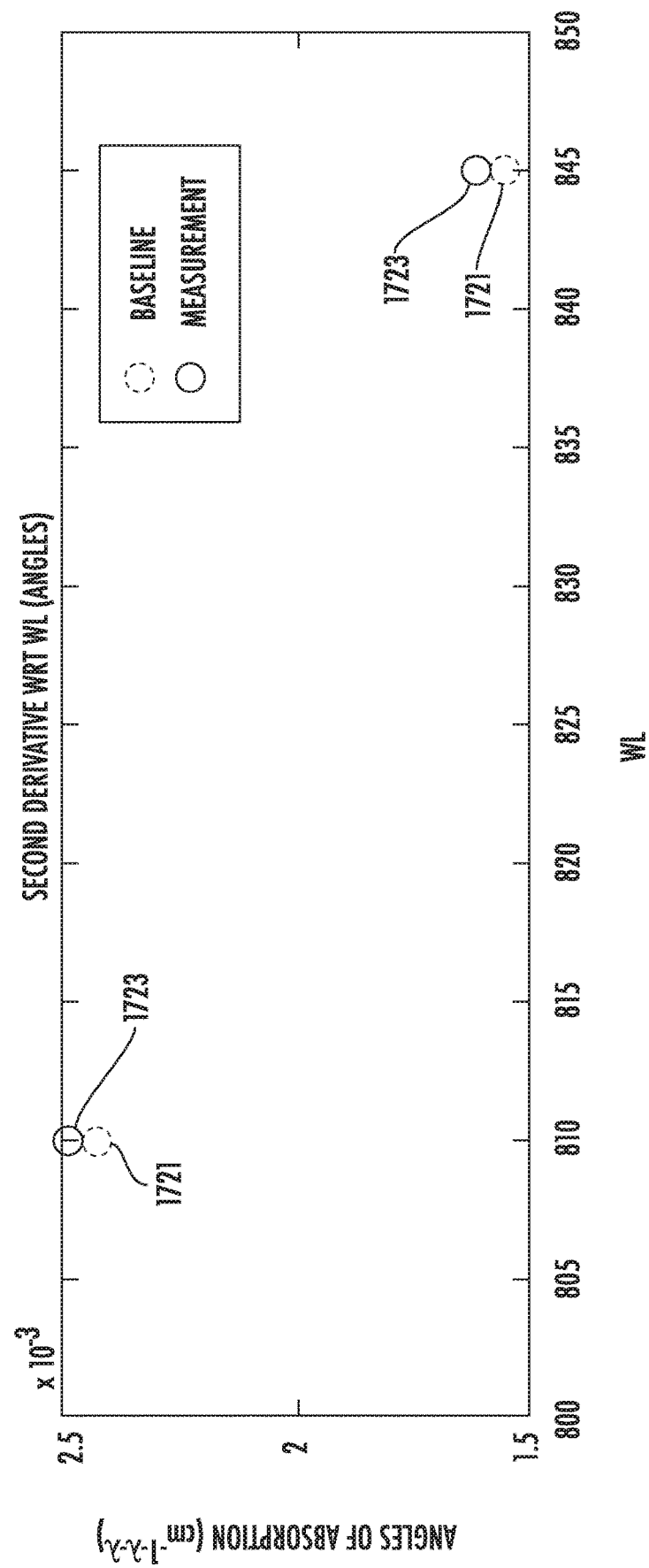
FIG. 17F shows a first example plot (e.g., two bottom points) of the second derivative of the absorption coefficients with respect to wavelength for the first target site and shows a second example plot (e.g., two top points) of the second derivative of the absorption coefficients with respect to wavelength for the second target site.

FIG. 17F shows a first example plot 1721 (e.g., to bottom points) of the second derivative of the absorption coefficients with respect to wavelength for the first target site and shows a second example plot 1723 (e.g., to top points) of the second derivative of the absorption coefficients with respect to wavelength for the second target site. The plots in FIG. 17D are for wavelengths of between 800 and 850 nanometers (e.g., specifically for 810 nanometers and 845 nanometers). The positive values of the example plots shown in FIG. 17F match the positive slope of the curve in FIG. 17E.

Figure 18:
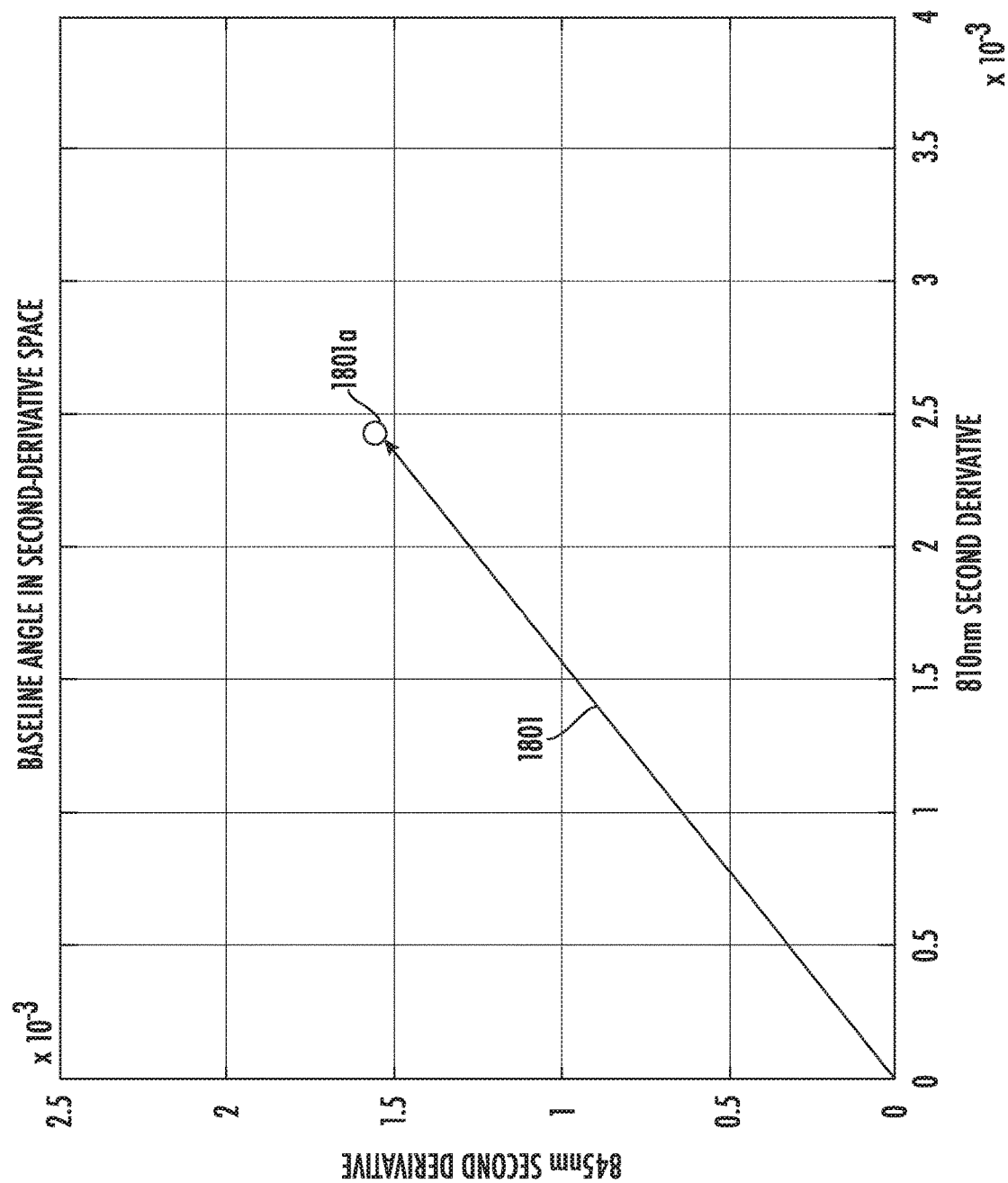
FIG. 18 shows a vector in "angle" space for the values of the second derivatives and plotted against each other.

FIG. 18 shows a vector ($\theta_1$, $\Phi_1$) in "angle" space for the values of the second derivatives $\theta_1$ and $\Phi_1$ plotted against each other. In angle space, the vertical and horizontal axes are for values $\theta_1$ and $\Phi_1$ of the second derivatives for two wavelengths of light. In the particular example, the vertical and horizontal axes are for values for the second derivative for 810 nanometers and 845 nanometers. Other wavelength values from the second derivatives can be chosen is the tissue is illuminated by other wavelengths of light. That is, the end point 1801a of the vector 1801 in angle space represents two values for the second derivative for the first tissue (e.g., healthy breast tissue) plotted against each other.

Figure 19:
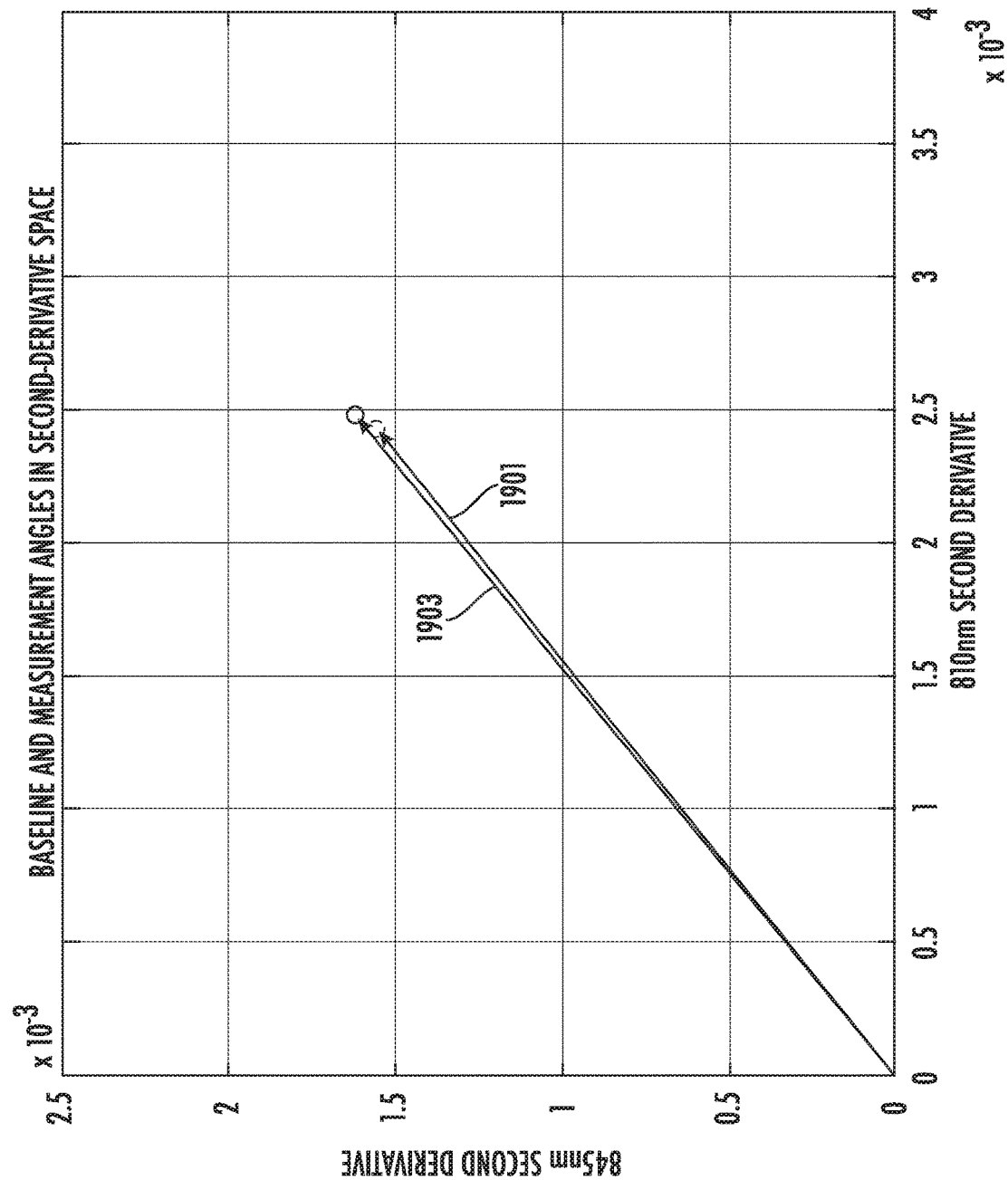
FIG. 19 shows the first vector ($\theta_1$, $\Phi_1$) and a second vector 1903 ($\theta_2$, $\Phi_2$) in "angle" space.

FIG. 19 shows the first vector 1901 ($\theta_1$, $\Phi_1$) and a second vector 1903 ($\theta_2$, $\Phi_2$) in "angle" space. That is, $\theta_1$, and $\Phi_1$ are plotted against each other and $\theta_2$ and $\Phi_2$ are plotted against each other. The difference between the two vector are the delta angles $\Delta\theta=\theta_1-\theta_2$ and $\Delta\Phi=\Phi_1-\Phi_2$ and represents the changes in the curvature of the curves (also sometimes referred to as spectra) for absorption coefficients for the first and second target tissues for wavelengths 810 and 845. The delta angles $\Delta\theta$ and $\Delta\Phi$ can be determined by the processor by projecting vector 1903 onto vector 1901. See FIG. 15 at 1535 and 1540.

Figure 20:
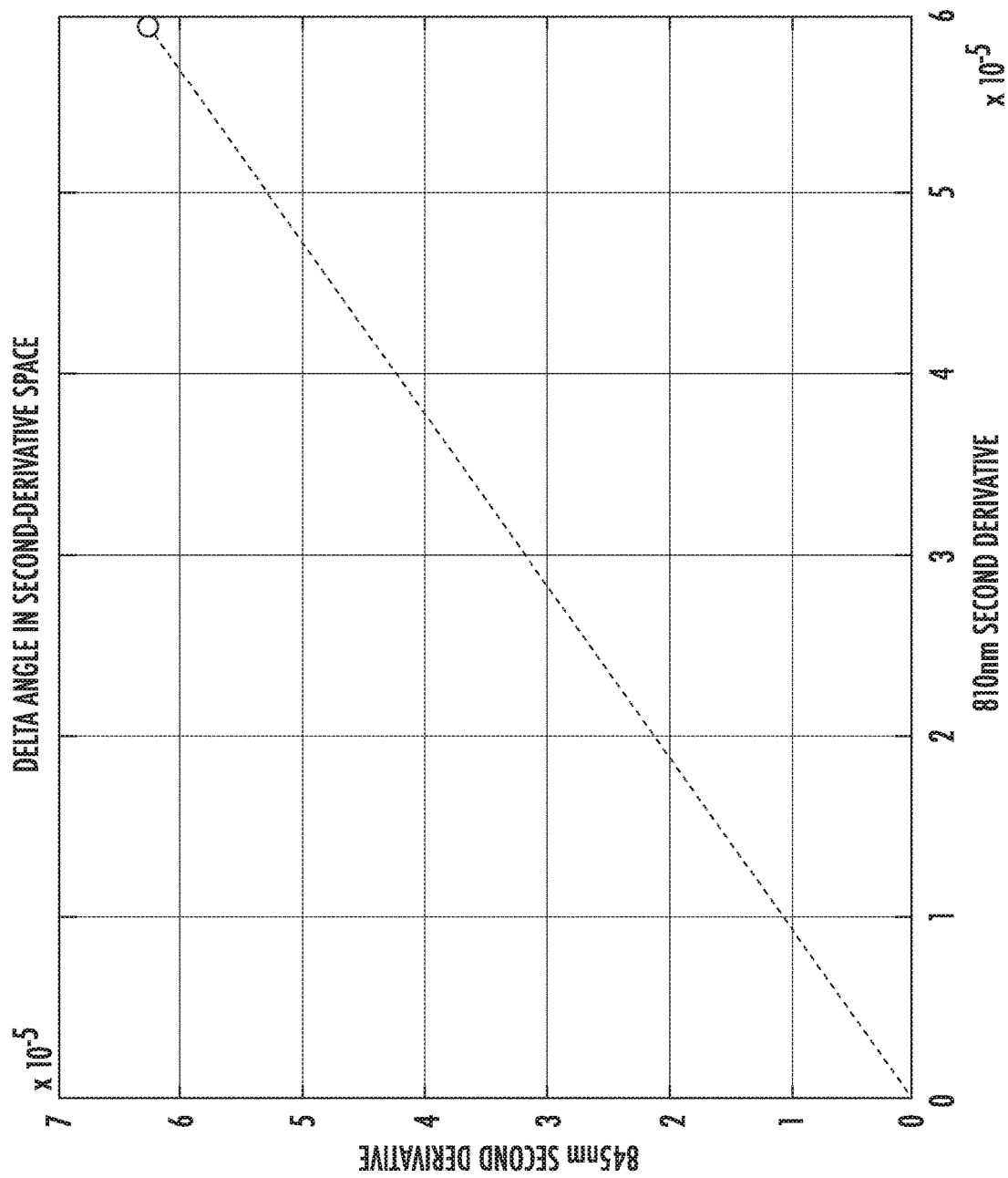
FIG. 20 shows one of the delta angles $\Delta\theta$ and $\Delta\Phi$ in vector space.

FIG. 20 shows one of the delta angles $\Delta\theta$ and $\Delta\Phi$ in vector space. The changes of curvature of the absorption coefficients are attributable to relative changes in the oxygen saturation between the first and second target tissue sites. Because the curvatures for the absorption coefficients of melanin are fixed or approximately fixed for the first and second target tissue (e.g., melanin concentrations are the same or similar for the first and second target tissue, single patient with contralateral measurements), the changes of curvature of the absorption coefficients $\Delta\theta$ and $\Delta\Phi$ are not attributable to melanin in the tissue sites. That is, any contribution to the second derivatives from melanin go to zero.

The relative change in oxygen saturation between the first and second target tissues is calculated from the delta angles $\Delta\theta$ and $\Delta\Phi$ and a value (e.g., percentage difference) for the relative change in oxygen saturation is displayed on the display of the oximeter probe. See FIG. 15 at 1545 and 1550. The processor of the oximeter probe performs this calculation. Specifically, the angle changes $\Delta\theta$ and $\Delta\Phi$ have an arbitrary scaling that is corrected so that the scaling is for blood. The correction can be based on a scaling factor, a correction vector, or both. The scaling factor, the correction vector, or both can be stored in the nonvolatile memory and remain resident in the memory when the oximeter probe is detached from a power source (e.g., the batteries are removed from the probe). These values may be generated when the oximeter is first manufactured and tested for use. The values are retrieved from the memory and loaded into the processor for use. The correction vector can be vector in angle space used by the processor to correct the vectors in angle space or correct the angle changes $\Delta\theta$ and $\Delta\Phi$ in angle space.

The correction vector is determined using a tissue phantom. The tissue phantom can be a liquid tissue phantom, one or more rigid tissue phantoms, or a combination of liquid and rigid tissue phantoms. The oximeter probe makes oxygen saturation measurements on the tissue phantom during a period of time when the tissue phantom has an initial blood oxygenation saturation of 100 percent (e.g., fully oxygenated) and lowers to 0 percent (e.g., fully deoxygenated).

The reflectance data (e.g., for 2, 3, 4, or more wavelengths of light, such as IR) that is generated by the oximeter probe for the tissue phantom is fit to the simulated reflectance curves to determine one or more simulated reflectance curves that best fits the reflectance data. The absorption coefficients associated with the one or more simulated reflectance curves are determined. First and second derivatives of the curves (e.g., spectrum) for the absorption coefficient are determined.

Figure 21A:
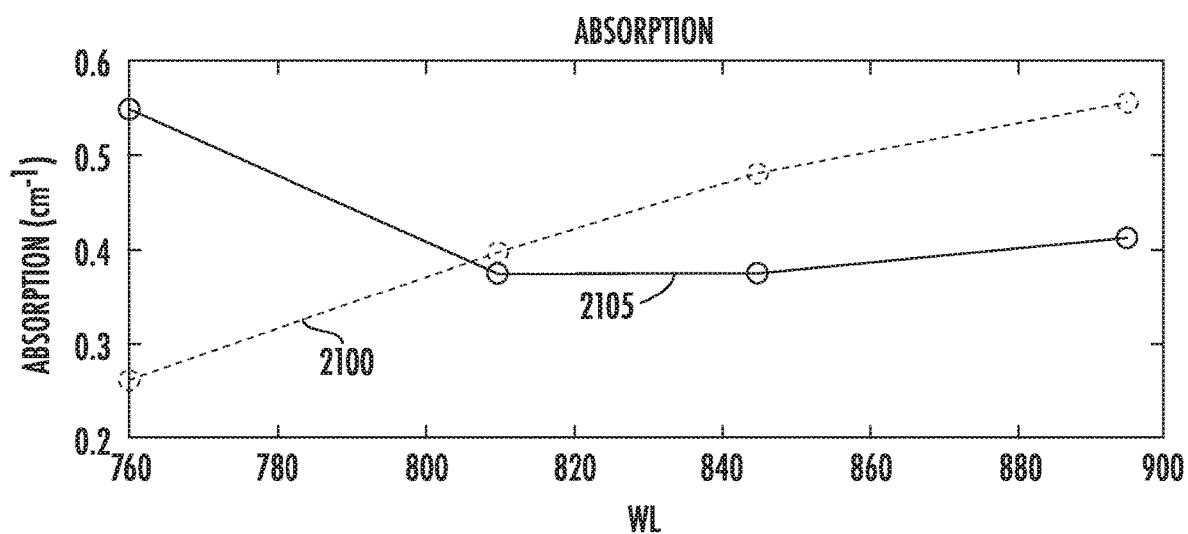
FIG. 21A shows a graph for the absorption coefficients (e.g., spectrum) for the fully oxygenated measurements and a graph 21 for the absorption coefficients for the fully deoxygenated measurements.
Figure 21B:
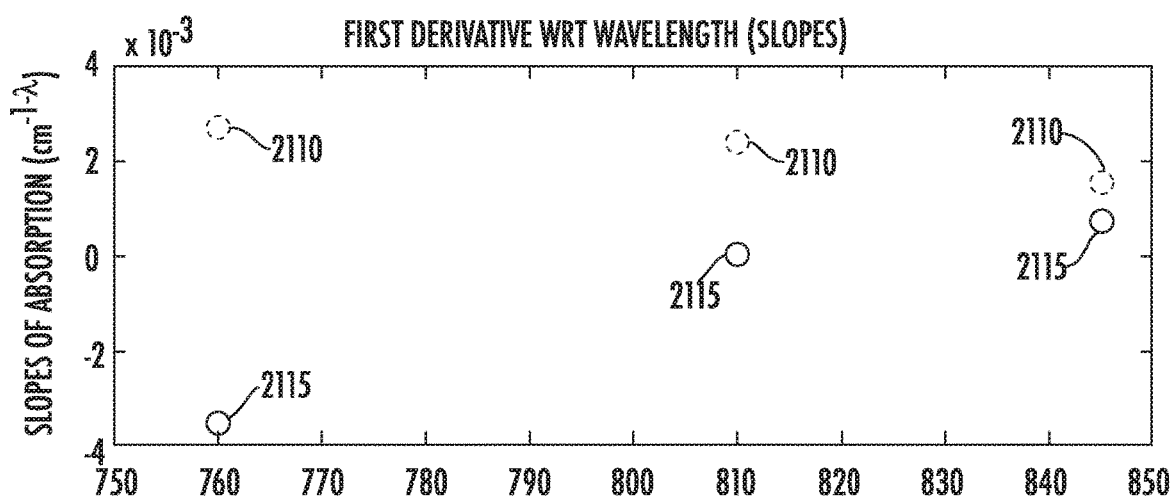
FIG. 21B shows a graph for the first derivative of the fully oxygenated spectrum with respect to wavelength and a graph for the first derivative with respect to wavelength of the fully deoxygenated spectrum.
Figure 21C:
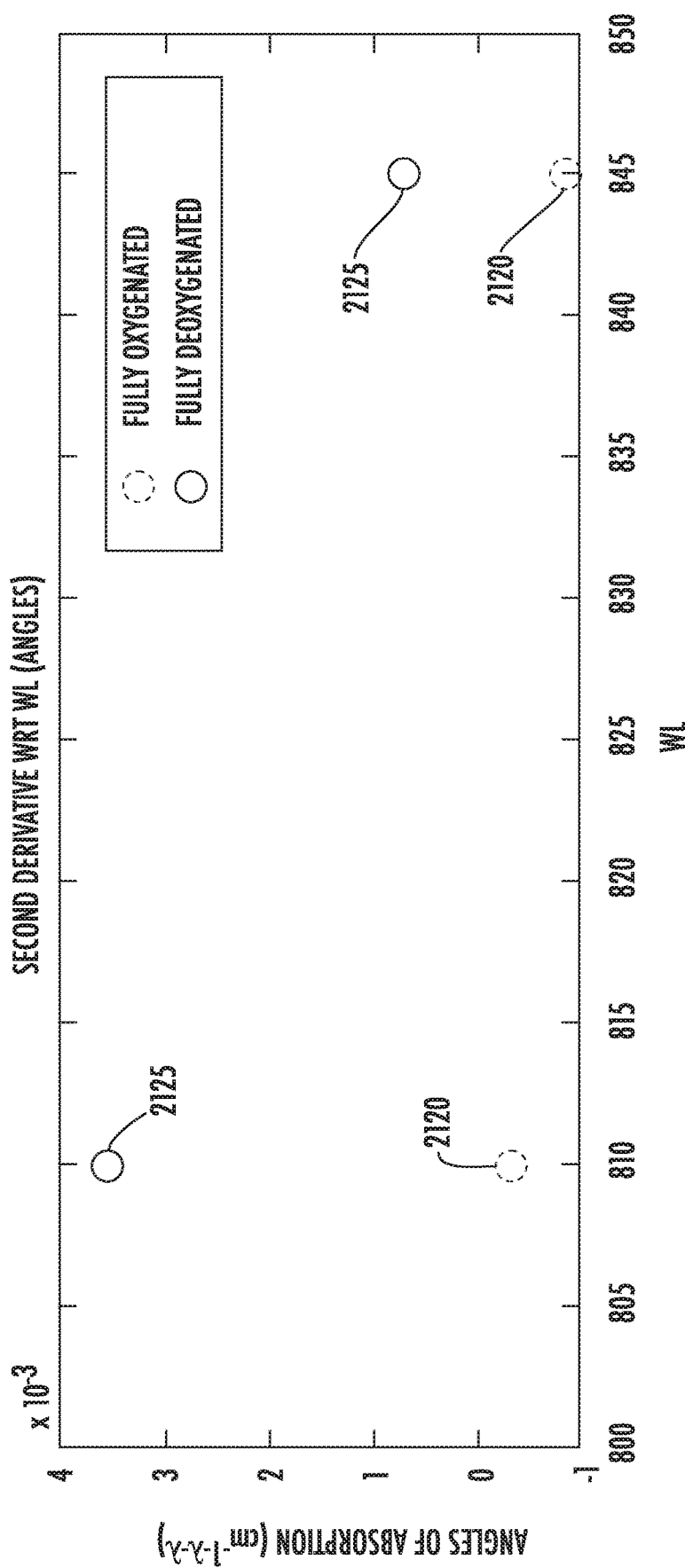
FIG. 21C shows a graph for the second derivative with respect to wavelength of the fully oxygenated spectrum and a graph for the second derivative with respect to wavelength of the fully deoxygenated spectrum.

FIG. 21A shows a graph 2100 for the absorption coefficients (e.g., spectrum) for the fully oxygenated measurements and a graph 2105 for the absorption coefficients for the fully deoxygenated measurements. FIG. 21B shows a first plot 2110 on graph for the first derivatives of the fully oxygenated spectrum with respect to wavelength and a second plot 2115 on the graph for the first derivative with respect to wavelength of the fully deoxygenated spectrum. FIG. 21C shows a first plot 2120 on a graph for the second derivative with respect to wavelength of the fully oxygenated spectrum and a second plot 1225 on the graph for the second derivative with respect to wavelength of the fully deoxygenated spectrum.

Thereafter, the angular deviations (e.g., $\theta_1$ onto $\Phi_1$) for the curves for the fully oxygenated measurements are determined for the same wavelengths (e.g., $\theta_1$ angular deviation between line from 760 nanometers to 810 nanometers and line from 810 nanometers to 845 nanometers, and $\Phi_1$ angular deviation between line from 810 nanometers to 845 nanometers and line from 845 nanometers and 890 nanometers) as the first and second target tissue measurements described above.

The angular deviations (e.g., $\theta_2$ onto $\Phi_2$) for the curves for the fully deoxygenated measurement are determined for the same wavelengths (e.g., $\theta_2$ angular deviation between line from 760 nanometers to 810 nanometers and line from 810 nanometers to 845 nanometers, and $\Phi_2$ angular deviation between line from 810 nanometers to 845 nanometers and line from 845 nanometers and 890 nanometers) as the first and second target tissue measurements described above.

Figure 22:
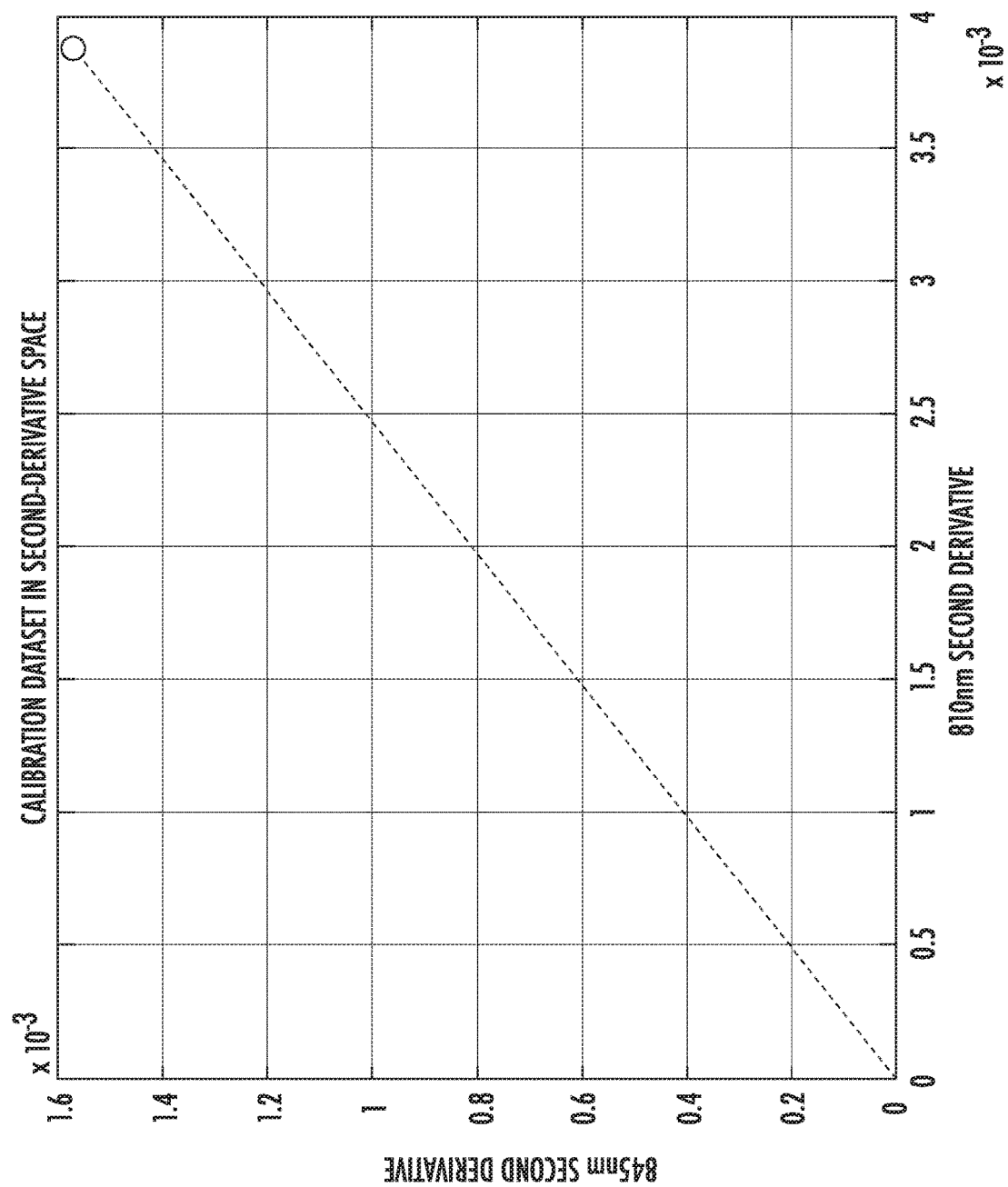
FIG. 22 shows the vector ($\Delta\theta$, $\Delta\Phi$) in angle space where $\Delta\theta$ and $\Delta\Phi$ are plotted against each other.

FIG. 22 shows the vector ($\Delta\theta$, $\Delta\Phi$) in angle space where $\Delta\theta$ and $\Delta\Phi$ are plotted against each other. The delta angles can be used for scaling (or calibrating) tissue measurements for first and second target tissue (e.g., contralateral breast tissue measurements).

These angular changes $\Delta\theta=\theta_1-\theta_2$ and $\Delta\Phi=\Phi_1-\Phi_2$ are determined by the processor. The delta angle represents the change in the curvature of the absorption spectra between the fully deoxygenated measurement and the fully deoxygenated measurements. The delta angles $\Delta\theta$ and $\Delta\Phi$ indicate what a 100 percent change in oxygenation for tissue is expected to look like and provides a reference that other smaller changes in delta angles $\Delta\theta$ and $\Delta\Phi$ (e.g., for contralateral breast tissue) can be corrected by to scale arbitrary scaled $\Delta\theta$ and $\Delta\Phi$ (e.g., for contralateral breast tissue).

The calculated vector ($\Delta\theta$, $\Delta\Phi$) for the tissue phantom is multiplied by a correction factor to correct for the difference in blood volume in the phantom and blood volume in patient tissue. The correction factor can be 10 or other factor to account for a different between blood volume 10 percent in the particular phantom used and 1 percent blood volume (or other percentage of blood volume 1.25 percent, 1.2 percent, 1.15 percent, 1.1 percent, 1.05 percent, 0.95 percent, 0.9 percent, 0.85 percent, 0.8 percent, or other values) for patient tissue. Alternatively, the correction factor can be applied to the measurements for the patient tissue as compared to the measurements for the phantom.

Figure 23:
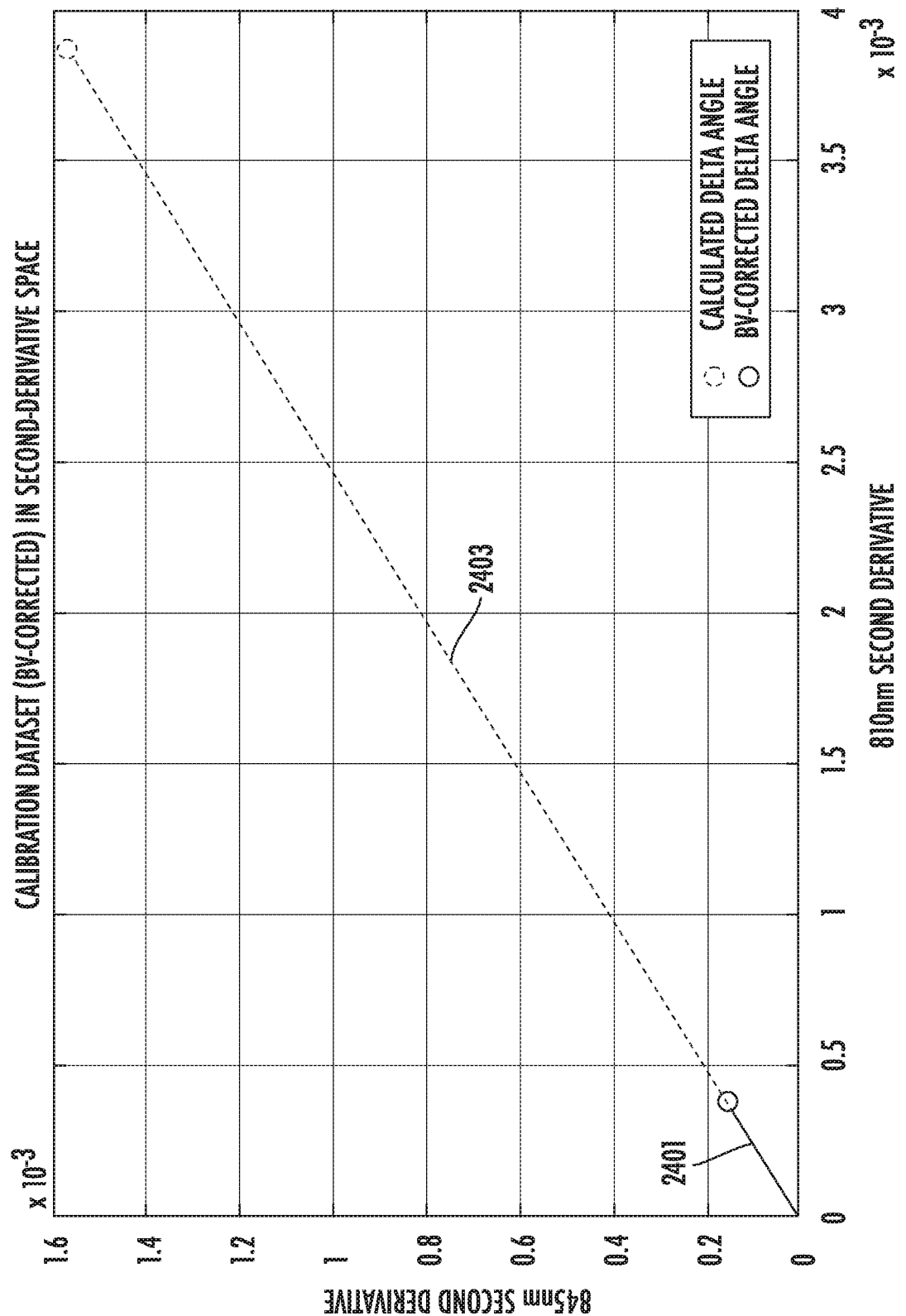
FIG. 23 shows the baseline corrected vector and the calculated vector corrected for the phantom corrected by the scaling factor for the difference in blood volume between the blood volume for the phantom and patient tissue.

FIG. 23 shows the baseline corrected vector 2401 and the calculated vector corrected 2403 for the phantom corrected by the scaling factor for the difference in blood volume between the blood volume for the phantom and patient tissue. The delta angles $\Delta\theta$ and $\Delta\Phi$ corrected for blood volume difference indicate what a 100 percent change in oxygenation for tissue is expected to look like and provides a reference that other smaller changes in delta angles $\Delta\theta$ and $\Delta\Phi$ for patient tissue (e.g., for contralateral breast tissue) can be corrected by to scale the arbitrary scaled $\Delta\theta$ and $\Delta\Phi$ for patient tissue.

Figure 24:
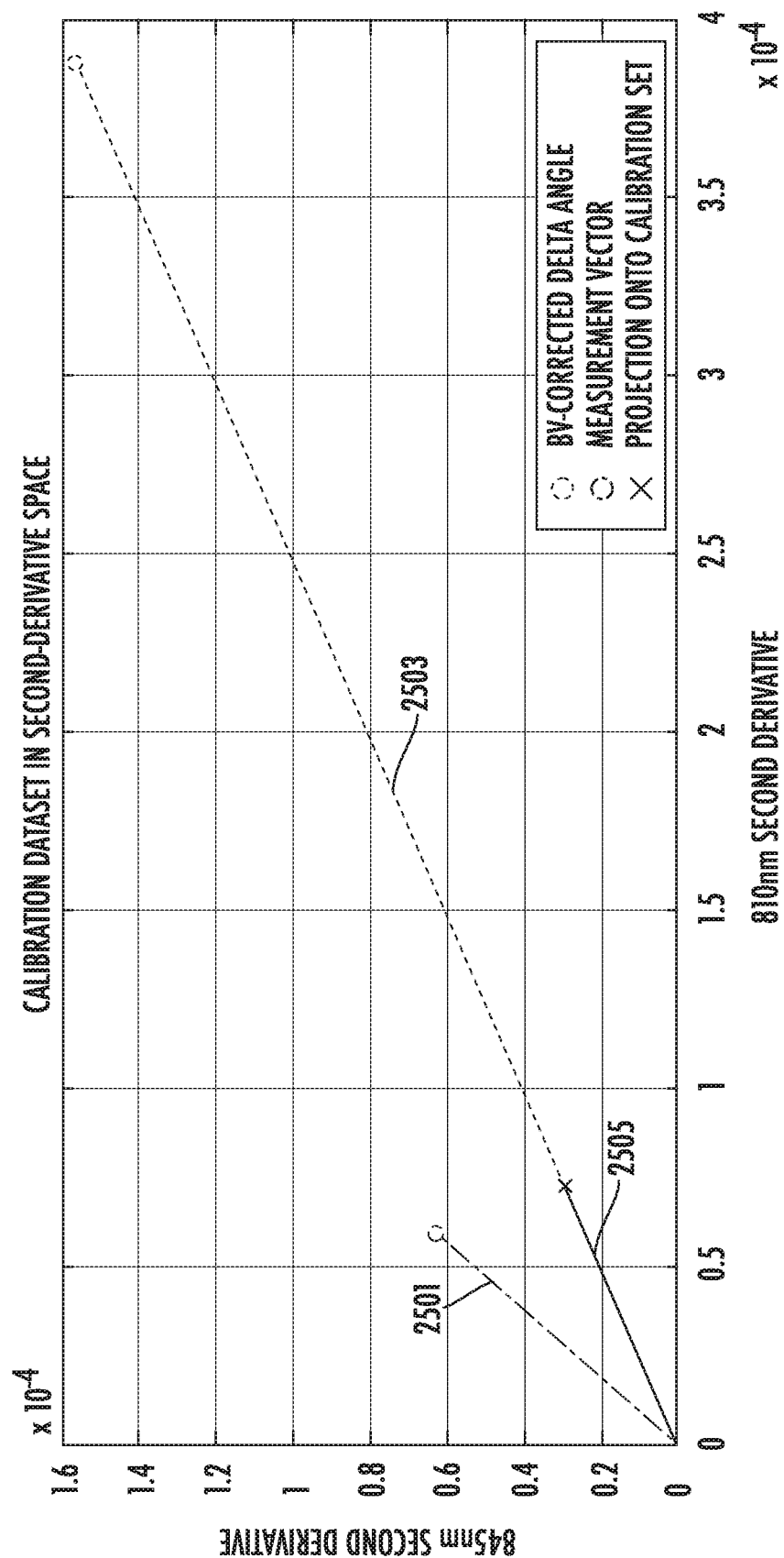
FIG. 24 shows the shows the vector for patient tissue projected onto the vector for the phantom.

In an implementation, the vector for patient tissue is scaled by the vector for the phantom by projecting the vector for the patient tissue onto the vector for the phantom vector. FIG. 24 shows the shows the vector 2501 for patient tissue projected onto the vector 2503 for the phantom. The result of the projection is labeled with reference number 2505.

In an implementation, the vector for patient tissue is scaled by the vector for the phantom (1550 of FIG. 15) dividing the normalized vector for the patient tissue by the normalized vector for the phantom (e.g., determining a percentage difference) and multiplying by 100 percent and −1.

$$\Delta SO_2 = (-1) * \frac{norm(projectedVector)}{norm(BVcorrectedCalibrationVector)} * 100\%$$

The factor −1 represents a measurement for a decrease in oxygen saturation of the patient tissue measured by the oximeter probe. In the example of FIG. 24, the relative increase in deoxygenation (e.g., decrease in oxygenation) between the contralateral target tissue of the patient is approximately 18 percent.

In an implementation, nonlinear transforms are used by the oximeter probe for scaling the vector ($\Delta\theta$, $\Delta\Phi$) for the patient tissue by the vector ($\Delta\theta$, $\Delta\Phi$) for the phantom.

In an implementation, the oximeter probe transmits light from at least one of the light source (e.g., source structures) of the oximeter probe into a first tissue (first breast tissue) at a first location to be measured.

The first tissue comprises a first melanin component, such as a first melanin content. The first melanin component includes eumelanin, pheomelanin, or both eumelanin, pheomelanin. A number of the detector structures receives the light subsequent to transmission through or reflectance from the first tissue.

The received light comprises a first melanin absorption component due to the first melanin component. That is the received light includes information for the melanin in the first tissue as the melanin absorbs a portion of the light transmitted into the first tissue.

The oximeter probe there after determines a melanin compensation component (e.g., an angle correction (such as $\theta_1$, $\theta_2$, $\Phi_1$, $\Phi_2$, $\Delta\theta$, $\Delta\Phi$, or any combination of these), an absorption coefficient determined from fitting reflectance data to the simulated reflectance curves, any preliminary, any intermediary, any final calculation result, or any combination of these) for a melanin absorption component due to a melanin component of tissue.

The melanin absorption component includes the first melanin component. The melanin component includes the first melanin component. The oximeter probe uses the melanin compensation component to obtain a melanin-corrected oxygen saturation value for the first tissue. The melanin-corrected oxygen saturation value accounts for the melanin absorption component.

In an implementation, a method includes contacting a probe tip of an oximeter probe to a first target tissue of a patient, where the first target tissue is healthy tissue; using the oximeter probe, making a first oximetry measurement on the first target tissue; determining, by a processor of the oximeter probe a first plurality of absorption coefficients that are dependent on a plurality of wavelengths of light emitted from the oximeter probe into the first target tissue when the measurement on the first target tissue is performed; contacting the probe tip to a second target tissue of the patient, where the second target tissue is tissue for which an oximetry saturation value is to be determined; using the oximeter probe, making a second oximetry measurement on the second target tissue; determining, by the processor of the oximeter probe a second plurality of absorption coefficients that are dependent on the first plurality of wavelengths of light emitted from the oximeter probe into the second target tissue when the measurement on the second target tissue is performed; calculating, by the processor, a first angular deviation and a second angular deviation of a curve for the first plurality of absorption coefficients for the first target tissue; calculating, by the processor, a third angular deviation and a fourth angular deviation of a curve for the second plurality of absorption coefficients for the second target tissue; calculating, by the processor, a first angular difference between the first and second angular deviations and a second angular difference between the third and fourth angular deviations; calculating, by the processor, a relative change in oxygen saturation between the first and second target tissues based on the first and second angular differences; and displaying, by a display of the oximeter probe, a value for the relative oxygen saturation.

The method can include transmitting first light from a source structure of the oximeter probe into the first target tissue; detecting first reflected light that is reflected from the first target tissue by a plurality of detector structures of the oximeter probe; generating by the detector structures first reflectance data for the first reflected light detected by the detector structures; fitting the reflectance data to a plurality of simulated reflectance curves; determining one or more best fitting ones of the simulated reflectance curves from the fit of the first reflectance data to the plurality of simulated reflectance curves, where each of the simulated reflectance curves is associated with a value for an absorption coefficient; and determining the first plurality of absorption coefficients for the one or more best fitting ones of the simulated reflectance curves to the first reflectance data.

The method can include transmitting second light from the source structure of the oximeter probe into the second target tissue; detecting second reflected light that is reflected from the second target tissue by the plurality of detector structures of the oximeter probe; generating by the detector structures second reflectance data for the second reflected light detected by the detector structures; fitting the second reflectance data to the plurality of simulated reflectance curves; determining one or more best fitting ones of the simulated reflectance curves from the fit of the second reflectance data to the plurality of simulated reflectance curves; and determining the second plurality of absorption coefficients for the one or more best fitting ones of the simulated reflectance curves to the second reflectance data.

The method can include scaling, by the processor, the first and second angular differences with a scaling vector, where the scaling vector representing a 100 percent difference in oxygenation of a tissue phantom. The scaling includes projecting a first vector comprising data points for the first and second angular differences in angle space onto the scaling vector in angle space. The scaling alternatively includes dividing a normalization of the first vector, that comprises data points for the first and second angular differences in angle space, by a normalization of the scaling vector.

The method can includes calculating, by the processor, a percentage difference of a quotient of the normalization of the first vector divided by the normalization of the scaling vector; and the quotient by negative one to include a decreasing in oxygenation between the first target tissue and the second target tissue. The value displayed on the display is the product of the quotient multiplied by negative one.

In an implementation, a system implements the method where the system includes an oximeter probe that includes a handheld housing; a processor housed in the handheld housing; a memory, housed in the handheld housing, electronically coupled to the processor and storing first code for controlling the processor; a display, accessible from an exterior of the handheld housing, electronically coupled to the processor; and a battery, housed in the handheld housing, coupled to and supplies power to the processor, the memory, and the display, where the code includes instruction executable by the processor executes steps for the method including making a first oximetry measurement on a first target tissue of a patient; determining a first plurality of absorption coefficients that are dependent on a plurality of wavelengths of light emitted from the oximeter probe into the first target tissue when the measurement on the first target tissue is performed; making a second oximetry measurement on a second target tissue of the patient; determining a second plurality of absorption coefficients that are dependent on the first plurality of wavelengths of light emitted from the oximeter probe into the second target tissue when the measurement on the second target tissue is performed; calculating a first angular deviation and a second angular deviation of a curve for the first plurality of absorption coefficients for the first target tissue; calculating a third angular deviation and a fourth angular deviation of a curve for the second plurality of absorption coefficients for the second target tissue; calculating a first angular difference between the first and second angular deviations and a second angular difference between the third and fourth angular deviations; calculating a relative change in oxygen saturation between the first and second target tissues based on the first and second angular differences; and displaying on the value for the relative oxygen saturation.

In an implementation a method includes contacting a probe tip to a first target tissue of a patient, where the first target tissue is healthy tissue; using the oximeter probe, making a first oximetry measurement on the first target tissue; determining, by a processor of the oximeter probe, a first absorption coefficient based on the first oximetry measurement for the first target tissue; contacting the probe tip to a second target tissue of the patient, where the second target tissue is tissue for which an oximetry saturation value is to be determined; using the oximeter probe, making a second oximetry measurement on the second target tissue; determining, by the processor of the oximeter probe a second absorption coefficient that is based on the second oximetry measurement for the second target tissue; generating, by the processor, a third absorption coefficient by adjusting the second absorption coefficient using first absorption coefficient; determining a value for oxygen saturation for the second target tissue from the third absorption coefficient; and displaying the value for the oxygen saturation for the second target tissue. The method can includes fitting first reflectance data for the first oximetry measurement to a plurality of simulated reflectance curves for determining by the processor the first absorption coefficient based on the first oximetry measurement for the first target tissue, where the simulated reflectance curves include modeling for melanin in simulated tissue; and determining, by the processor, the first absorption coefficient from one or more best fitting one of the simulated reflectance curves.

This description of the invention has been presented for the purposes of illustration and description. It is not intended to be exhaustive or to limit the invention to the precise form described, and many modifications and variations are possible in light of the teaching above. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

The invention claimed is:

1. A method comprising:
transmitting first light from a light source of an oximeter probe into a first tissue at a first location to be measured, wherein the first tissue comprises a first melanin component, and the first melanin component comprises at least one of eumelanin or pheomelanin;
receiving the first light at a detector of the oximeter probe that is reflected by the first tissue in response to the transmitted first light, wherein the received first light comprises a first melanin absorption component due to the first melanin component;
transmitting second light from the light source of the oximeter probe into a second tissue at a second location to be measured, wherein the second location is different from the first location, and second tissue comprises a second melanin component, and the second melanin component comprises at least one of eumelanin or pheomelanin;
receiving the second light at the detector of the oximeter probe that is reflected by the second tissue in response to the transmitted light, wherein the received second light comprises a second melanin absorption component due to the second melanin component;
determining a melanin compensation component for a melanin absorption component due to a melanin component of tissue, wherein the melanin absorption component comprises the first and second melanin components; and
using the melanin compensation component, obtaining a melanin-corrected oxygen saturation value for the first tissue, wherein the melanin-corrected oxygen saturation value accounts for the melanin absorption component.

2. The method of claim 1 comprising:
determining a first plurality of absorption coefficients that are dependent on a plurality of wavelengths of the first light emitted from the oximeter probe into the first tissue when the measurement on the first tissue is performed;
determining a second plurality of absorption coefficients that are dependent on the plurality of wavelengths of the second light emitted from the oximeter probe into the second tissue when the measurement on the second tissue is performed;

generating a third absorption coefficient by adjusting at least one of the absorption coefficients of the first plurality of absorption coefficients using at least one of the absorption coefficients of the second plurality of absorption coefficients; and generating the melanin-corrected oxygen saturation value for the first tissue using the third absorption coefficient.

3. The method of claim 2 comprising:

fitting first reflectance data, for the first light received at the detector of the oximeter probe for the first tissue, to a plurality of simulated reflectance curves for determining the at least one of the absorption coefficients of the first plurality of absorption coefficients, wherein the simulated reflectance curves include modeling for melanin in simulated tissue; and determining, by the processor, the at least one of the absorption coefficients of the first plurality of absorption coefficients from one or more best fitting ones of the simulated reflectance curves.

4. The method of claim 3 comprising:

fitting second reflectance data, for the second light received at the detector of the oximeter probe for the second tissue, to the plurality of simulated reflectance curves for determining the at least one of the absorption coefficients of the second plurality of absorption coefficients; and determining, by the processor, the at least one of the absorption coefficients of the second plurality of absorption coefficients from one or more best fitting one of the simulated reflectance curves.

5. The method of claim 1 wherein the first location and second location are contralateral locations on a body.

6. The method of claim 1 comprising:

calculating a first angular deviation and a second angular deviation of a curve for the first plurality of absorption coefficients for the first tissue;

calculating a third angular deviation and a fourth angular deviation of a curve for the second plurality of absorption coefficients for the second tissue;

calculating a first angular difference between the first and second angular deviations and a second angular difference between the third and fourth angular deviations; and calculating a relative change in oxygen saturation between the first and second tissues based on the first and second angular differences.

7. The method of claim 6 comprising calculating a relative difference in oxygen saturation between the first and second tissues based on the first and second angular differences.

8. A method comprising:

transmitting first light from a light source of an oximeter probe into a first tissue at a first location to be measured, wherein the first tissue comprises a first melanin component, and the first melanin component comprises at least one of eumelanin or pheomelanin;

receiving the first light at a detector of the oximeter probe that is reflected by the first tissue in response to the transmitted first light, wherein the received first light comprises a first melanin absorption component due to the first melanin component;

determining a melanin compensation component for a melanin absorption component due to a melanin component of tissue, wherein the melanin absorption component comprises the first and second melanin components, wherein the determining the melanin compensation component for the melanin absorption component due to the melanin component comprises:

transmitting second light from the light source of the oximeter probe into a second tissue at a second location to be measured, wherein the second location is different from the first location, and the second tissue comprises a second melanin component, and the second melanin component comprises at least one of eumelanin or pheomelanin;

receiving the second light at the detector of the oximeter probe that is reflected by the first tissue in response to the transmitted light, wherein the received second light comprises a second melanin absorption component due to the second melanin component;

determining a first plurality of absorption coefficients that are dependent on a plurality of wavelengths of the first light emitted from the oximeter probe into the first tissue when the measurement on the first tissue is performed; and determining a second plurality of absorption coefficients that are dependent on the first plurality of wavelengths of the second light emitted from the oximeter probe into the second tissue when the measurement on the second tissue is performed; and using the melanin compensation component, obtaining a melanin-corrected oxygen saturation value for the first tissue, wherein the melanin-corrected oxygen saturation value accounts for the melanin absorption component.

9. The method of claim 8 wherein the determining the melanin compensation component for the melanin absorption component due to the melanin component comprises:

calculating a first angular deviation and a second angular deviation of a curve for the first plurality of absorption coefficients for the first tissue;

calculating a third angular deviation and a fourth angular deviation of a curve for the second plurality of absorption coefficients for the second tissue;

calculating a first angular difference between the first and second angular deviations and a second angular difference between the third and fourth angular deviations; and calculating a relative change in oxygen saturation between the first and second tissues based on the first and second angular differences.

10. The method of claim 8 comprising:

adjusting the absorption coefficients of the second plurality of absorption coefficients for each wavelength of the first light using the reflectance data for the first tissue, wherein the melanin compensation component comprises the adjusted absorption coefficients; and determining an oxygen saturation value for the second tissue using the adjusted absorption coefficients.

11. The method of claim 9 comprising displaying, on a display of the oximeter probe, the melanin-corrected oxygen saturation value, wherein the melanin-corrected oxygen saturation value is a value for the relative change in oxygen saturation between the first and second tissues.

12. The method of claim 11 wherein the determining the melanin compensation component for the melanin absorption component due to the melanin component comprises scaling the first and second angular differences with a scaling vector, wherein the scaling vector representing a 100 percent difference in oxygenation of a tissue phantom.

13. The method of claim 8 wherein the determining the melanin compensation component for the melanin absorption component due to the melanin component comprises:

generating a third absorption coefficient by adjusting at least one of the coefficients of the first plurality of absorption coefficients using at least one of the absorption coefficients of the second plurality of absorption coefficients; and generating the melanin-corrected oxygen saturation value for the first tissue using the third absorption coefficient.

14. The method of claim 13 wherein the determining the melanin compensation component for the melanin absorption component due to the melanin component comprises:

fitting first reflectance data for the first light received at the detector of the oximeter probe for the first tissue to a plurality of simulated reflectance curves for determining the at least one of the absorption coefficients of the first plurality of absorption coefficients, wherein the simulated reflectance curves include modeling for melanin in simulated tissue; and determining, by a processor, the at least one of the absorption coefficients of the first plurality of absorption coefficients from one or more best fitting one of the simulated reflectance curves.

15. The method of claim 14 wherein the determining the melanin compensation component for the melanin absorption component due to the melanin component comprises:

fitting second reflectance data for the second light received at the detector of the oximeter probe for the second tissue to the plurality of simulated reflectance curves for determining the at least one of the absorption coefficients of the second plurality of absorption coefficients; and determining, by the processor, the at least one of the absorption coefficients of the second plurality of absorption coefficients from one or more best fitting one of the simulated reflectance curves.

16. A system comprising:

an oximeter device comprising a probe tip comprises source structures and detector structures on a distal end of the device, a processor, and a display proximal to the probe tip and coupled to the processor, wherein the processor of the oximeter device calculates a melanin-corrected oxygen saturation value, and displays the melanin-corrected oxygen saturation value on the display, and the processor of the oximeter device is specially configured to:

use the probe tip to make a first measurement and a second measurement to determine the melanin-corrected oxygen saturation value;

receive first information based on the first measurement of a first tissue at a first location when the probe tip is positioned on the first tissue, wherein the melanin-corrected oxygen saturation value is unavailable for display after the first measurement is made and before the second measurement is made;

receive second information based on the second measurement of a second tissue at a second location when the probe tip is positioned on the second tissue, wherein the second location is different from the first location; and use the first information and second information to determine the melanin-corrected oxygen saturation value, wherein the melanin-corrected oxygen saturation value takes into account melanin components of the first tissue and second tissue, and the melanin components comprise eumelanin and pheomelanin.

17. The system of claim 16 wherein the first location is at a first position of the body, the second location is at a second position of the body, and the first position and second position are contralateral with respect to each other.

18. The system of claim 16 wherein the oximeter device is a handheld oximeter comprising a power source and an electronic processor housed within an enclosure that also houses the source structures and detector structures of the probe tip.

19. The system of claim 16 wherein the oximeter device comprises a memory, and the memory stores first simulated reflectance curves for a first melanin content value, second simulated reflectance curves for a second melanin content value, and the first melanin content value is different from the second melanin content value.

20. The system of claim 19 wherein the oximeter device is specially configured to:

based on the first and second information, determine a melanin content value for the first tissue and second tissue; and use the determined melanin content value to select one of the first simulated reflectance curves or the second simulated reflectance curves stored in the memory by comparing the determined melanin content value against the melanin content value associated with each of the simulated reflectance curves.

\* \* \* \* \*